United States Patent
Webster et al.

(10) Patent No.: US 8,795,691 B2
(45) Date of Patent: Aug. 5, 2014

(54) NANOTUBES AND COMPOSITIONS THEREOF

(75) Inventors: Thomas J. Webster, Barrington, RI (US); Hicham Fenniri, Edmonton (CA); Usha Devi Hemraz, Edmonton (CA)

(73) Assignees: Brown University, Providence, RI (US); National Research Council of Canada (CA); The Governors of the University of Alberta (CA)

( * ) Notice: Subject to any disclaimer, the term of this patent is extended or adjusted under 35 U.S.C. 154(b) by 0 days.

(21) Appl. No.: 13/634,340

(22) PCT Filed: Mar. 16, 2011

(86) PCT No.: PCT/US2011/028654
§ 371 (c)(1),
(2), (4) Date: Dec. 19, 2012

(87) PCT Pub. No.: WO2011/116085
PCT Pub. Date: Sep. 22, 2011

(65) Prior Publication Data
US 2013/0129788 A1 May 23, 2013

Related U.S. Application Data

(60) Provisional application No. 61/314,243, filed on Mar. 16, 2010.

(51) Int. Cl.
*A61K 39/35* (2006.01)
*A61K 9/14* (2006.01)
*C07D 239/00* (2006.01)
*C07D 403/00* (2006.01)

(52) U.S. Cl.
USPC ............ 424/400; 424/489; 544/245; 544/296

(58) Field of Classification Search
USPC ........................................................ 424/400
See application file for complete search history.

(56) References Cited

U.S. PATENT DOCUMENTS

| | | | |
|---|---|---|---|
| 4,103,002 A | 7/1978 | Hench et al. | |
| 4,775,646 A | 10/1988 | Hench et al. | |
| 4,851,046 A | 7/1989 | Low et al. | |
| 6,136,029 A * | 10/2000 | Johnson et al. | 623/16.11 |
| 6,696,565 B2 | 2/2004 | Fenniri | |
| 2002/0192636 A1* | 12/2002 | Guarino et al. | 435/4 |
| 2005/0131230 A1 | 6/2005 | Fenniri | |

OTHER PUBLICATIONS

Webster, T.J. "Nanophase Ceramics: The Future Orthopedic and Dental Implant Material" Advances in Chemical Engineering, 2001, 27, 125-166.*
Montalbetti et al. "Amide bond formation and peptide coupling" Tetrahedrom, 2005, 61, 10827-10852.*
Mei et al. "Improved Biological Characteristics of Poly(L-Lactic Acid) Electrospun Membrane by Incorporation of Multiwalled Carbon Nanotubes/Hydroxyapatite Nanoparticles" Biomacromolecules 2007, 8, 3729-3735.*
Chun et al. "Helical rosette nanotubes: a more effective orthopaedic implant material" Nanotechnology 2004, 15, S234-S239.*
Danumah et al. "Synthesis of Porous Silica Nanotubes using Rosette Nanotubes as Templates" Mater. Res. Soc. Symp. Proc., 2008, vol. 1057.*
International Search Report and Written Opinion issued from corresponding PCT/US2011/028654, dated May 13, 2011.
Atherton, E., et al.,"A Mild Procedure for Solid Phase Peptide Synthesis: Use of Fluorenylmethoxycarbonylamino-acids," Journal of the Chemical Society: Chemical Communications, Jul. 5, 1978, pp. 537-539, No. 13, The Chemical Society.
Carping, Louis A., et al.,"The 9-Fluorenylmethoxycarbonyl Amino-Protecting Group," J. Org. Chem., Apr. 10, 1972, pp. 3404-3409, vol. 37, No. 22.
Chun, Al Lin, et al.,"Helical rosette nanotubes: a more effective orthopaedic implant material," Nanotechnology, Feb. 20, 2004, pp. S234-S239, vol. 15, IOP Publishing Ltd.
Chun, Al Lin, et al.,"Helical rosette nanotubes: A biomimetic coating for orthopedics?" Biomaterials, Jul. 15, 2005, pp. 7304-7309, vol. 26, Elsevier Ltd.
Dee, Kay C., et al.,"Design and function of novel osteoblast-adhesive peptides for chemical modification of biomaterials," J. Biomed. Mater. Res., 1998, pp. 371-377, vol. 40, John Wiley & Sons, Inc.
Faraji, Amir H., et al.,"Nanoparticles in cellular drug delivery," Bioorganic & Medicinal Chemistry, Feb. 26, 2009, pp. 2950-2962, vol. 17, Elsevier Ltd.
Fenniri, Hicham, et al.,"Helical Rosette Nanotubes: Design, Self-Assembly, and Characterization," J. Am. Chem. Soc., Mar. 31, 2001, pp. 3854-3855, vol. 123, American Chemical Society.
Fine, Eli, et al.,"Enhanced endothelial cell functions on rosette nanotube-coated titanium vascular stents," International Journal of Nanomedicine, 2009, pp. 91-97, vol. 4, Dove Medical Press Ltd.
Mei, Fang, et al.,"Improved Biological Characteristics of Poly(L-Lactic Acid) Electrospun Membrane by Incorporation of Multiwalled Carbon Nanotubes/Hydroxyapatite Nanoparticles," Biomacromolecules, Nov. 19, 2007, pp. 3729-3735, vol. 8, American Chemical Society.
Merrifield, R. B.,"Solid Phase Peptide Synthesis. I. The Synthesis of a Tetrapeptide," J. Am. Chem. Soc., Jul. 20, 1963, pp. 2149-2154, vol. 85, No. 14.
Moralez, Jesus G., et al.,"Helical Rosette Nanotubes with Tunable Stability and Hierarchy," J. Am. Chem. Soc., Mar. 9, 2005, pp. 8307-8309, vol. 127, American Chemical Society.
Zhang, Lijie, et al.,"Biomimetic helical rosette nanotubes and nanocrystalline hydroxyapatite coatings on titanium for improving orthopedic implants," International Journal of Nanomedicine, 2008, pp. 323-333, vol. 3, No. 3, Dove Medical Press Ltd.
Zhang, Lijie, et al.,"Arginine-glycine-aspartic acid modified rosette nanotube-hydrogel composites for bone tissue engineering," Biomaterials, 2009, pp. 1309-1320, vol. 30, Elsevier Ltd.

* cited by examiner

*Primary Examiner* — Brian-Yong Kwon
*Assistant Examiner* — Andrew S Rosenthal
(74) *Attorney, Agent, or Firm* — Banner & Witcoff, Ltd.

(57) ABSTRACT

The present invention is directed to implants and the modification of the surface of implants using amino acid or polypeptide functionalized rosette nanotubes.

41 Claims, 22 Drawing Sheets

RGD-G$_A$C & K-G$_A$C    Rosettes from RGD-G$_A$C & K-G$_A$C    K$^{95}$/RGD$^5$-RNT$^m$ K-G$_A$C    Rosette    K-RNT$^m$

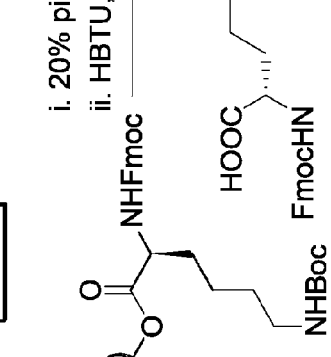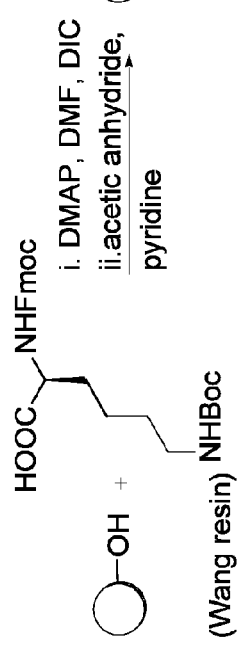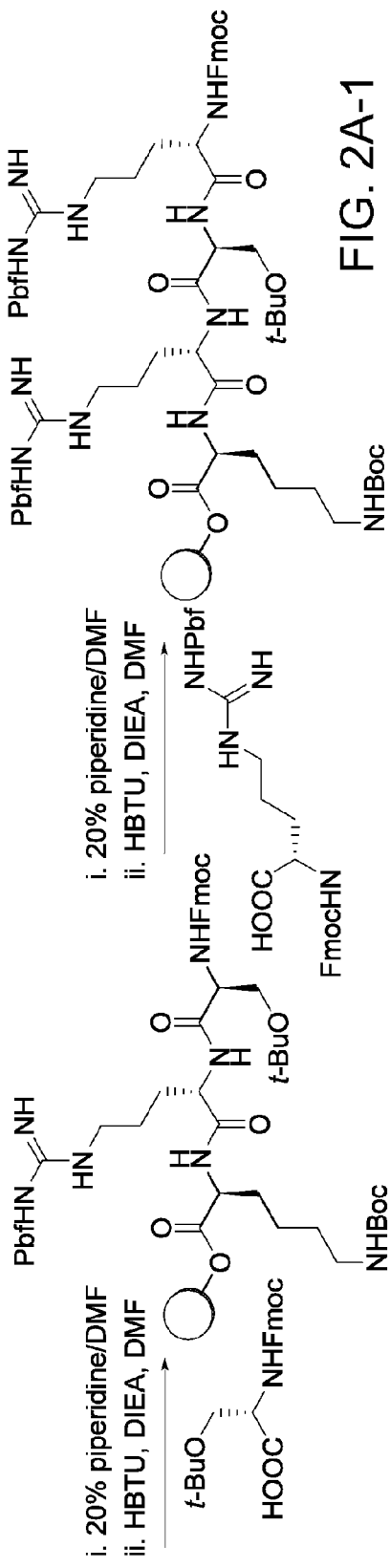
FIG. 2A
FIG. 2A-1

NANOTUBES AND COMPOSITIONS THEREOF

RELATED APPLICATION DATA

This application is a National Stage Application under 35 U.S.C. 371 of PCT application PCT/US2011/028654 designating the United States and filed Mar. 16, 2011; which claims the benefit of U.S. application 61/314,243 and filed Mar. 16, 2010 each of which are hereby incorporated by reference in their entireties.

STATEMENT OF GOVERNMENT INTERESTS

This invention was made with government support under R21_AG027521 awarded by National Institutes of Health. The Government has certain rights in the invention.

FIELD

The present invention relates to the field of implants, and more particularly to the modification of the surface of implants using polypeptide-functionalized nanotubes. The present invention further relates to the modification of the surface of an implant device using certain polypeptide-functionalized nanotubes to selectively promote adhesion of certain cells to the surface of the implant device. According to one aspect, the surface of an implant modified to include polypeptide-functionalized nanotubes promotes the adhesion of osteoblasts to the implant. The present invention also relates to methods, compositions and composites including nanotubes for tissue repair and regeneration.

BACKGROUND

The use of G∧C motifs to self-assemble into helical rosette nanotubes is known. See U.S. Pat. No. 6,696,565, Fenniri et al, *J. Am. Chem. Soc.* 2001, 123, 3854-3855 and Moralez et al., *J. Am. Chem. Soc.,* 2005, 127, 8307-8309. It is desirable to modify the surface of implants so as to increase the ability of cells to adhere to the implant surface and form tissue thereon. It is also desirable to provide compositions useful in making implants which promote the growth of tissue on and into the implant.

It is therefore an object of the present invention to create functionalized modules that can assemble into substructures, which themselves can assemble into more complex structures on a nanometer scale, such as a nanotube. It is a further object of the present invention to create functionalized modules which can self-assemble into ring structures for use in creating nanotubes that can be used as a coating for implants. It is a still further object to functionalize the modules with one or more moieties that enhance or improve the adhesion of selected cells to the implant. It is also an object of the present invention to modify the surface of an implant with nanotubes having moieties that increase the adhesion of cells to the surface of the implant. It is a still additional object of the present invention to tailor the polypeptides on the nanotubes to selectively promote adhesion of certain cells that are desirable to the formation of tissue on the implant. It is a further still additional object of the present invention to provide compositions or composites including nanotubes, nanoparticles and matrix materials for tissue repair and regeneration which can placed at a site within the body and on or into which growth of tissue can be promoted. These and other objects, features, and advantages of the invention or certain embodiments of the invention will be apparent to those skilled in the art from the following disclosure and description of exemplary embodiments.

SUMMARY

Embodiments of the present invention are directed to methods of altering the surface of a substrate to improve cell adhesion, proliferation and/or differentiation on the surface of the substrate. Substrates within the scope of the present invention include implant surfaces where cell adhesion is desired and/or cellular growth and/or cellular differentiation on the substrate itself or at the location of the implant within the body. Examples of such implants are those associated with orthopedic applications. According to this aspect of the invention, the surface of the implant is modified to include a nanostructured outer surface. An implant with such a surface according to the present invention provides greater cell adhesion as compared to an implant without the nanostructured outer surface.

Certain embodiments of the present invention are directed to coatings on the surface of implants that selectively promote adhesion of certain cell types to the surface of the implant. According to certain aspects, the coatings provide a desirable surface chemistry or condition which promotes selective cell adhesion, proliferation and/or differentiation. According to certain other aspects, the coating is biomimetic. Coatings according to certain embodiments of the present invention include nanometer scale molecular architectures, such as nanotubes, that include moieties or sidechains that selectively promote adhesion of certain cell types to the surface of the implant. Further embodiments allow for the selective adhesion of certain cell types compared to other certain cell types. The nanometer scale molecular architectures can be used alone or in combination with components suitable for creating a coating on the surface of a substrate and for proliferating and/or differentiating cells. According to certain other embodiments, the coatings that include the nanometer scale molecular architectures promote the adhesion of selected cells and growth of tissue on the surface of the implant. According to still other embodiments, the coatings that include the nanometer scale molecular architectures are osteogenic insofar as they promote the adhesion of osteoblasts and the growth of the osteoblasts into bone tissue.

Certain embodiments of the present invention are directed to a composition or composite for tissue repair and regeneration. The terms composition and composite can be used interchangeably herein. The compositions can be in the form of injectable liquids, moldable putties or hardened structures. The hardened structures may be rigid, semi-rigid, or flexible. The hardened structures may be porous or nonporous. According to one aspect, the injectable liquids and moldable putties may harden when placed within the environment of the body. For example, composites within the present disclosure can be injected as a liquid and solidify in situ simply through exposure to body temperatures. It is to be understood that the injectable liquids, moldable putties or hardened structures can be referred to as implants.

According to one embodiment, the composition includes the nanometer scale molecular architectures, a compound providing mechanical strength and a matrix material. The composition can be placed at a site within the body where structural support is desired. The composition can be placed within the body where tissue growth or regeneration is desired. The composition can be placed within the body where a combination of structural support and tissue growth or regeneration is desired. The composition can be permanent or biodegradable or bioresorbable. The composition can also be fashioned into various implant shapes to occupy a site where tissue has been removed such as a bone chip or fracture. The composition can also be fashioned into devices useful in rebuilding damaged tissue sites such as plates, rods, screws, cages, scaffolds, films, and coatings. The size, shape and manufacture of such devices including the compositions described herein and their use is well known to those of skill in the art and will be readily apparent based on the present disclosure.

The composition or composite selectively promotes the adhesion of certain cell types to the surface of the composition or composite. According to certain aspects, the composition provides a desirable surface chemistry or nanometer scale surface geometry or condition which promotes selective cell adhesion, proliferation and/or differentiation. According to certain other aspects, the composition is biomimetic. The composition of the present disclosure includes nanometer scale molecular architectures, such as nanotubes, that in some embodiments include moieties or sidechains that selectively promote adhesion of certain cell types to the surface of the implant. Further embodiments include nanoparticles in addition to the nanotubes to provide a nanometer scale surface geometry intended to promote cell adhesion, proliferation and/or differentiation. Further embodiments allow for the selective adhesion of certain cell types compared to other certain cell types.

Embodiments of the present invention are also directed to modules, including functionalized modules that self-assemble into more complex structures on a nanometer scale, such as a nanotube. The functionalized modules include one or more moieties that promote the adhesion of cells when present in a coating on the surface of a substrate, such as the surface of an implant. According to certain embodiments of the present invention, the nanometer scale structure can include several different moieties, i.e. two or more moieties or a plurality of moieties, that selectively promote adhesion of certain cell types. According to certain other embodiments, the certain cell types include those useful in promoting the expansion and growth of cells into tissue. According to a particular embodiment, the certain cell types include osteoblasts, fibroblasts, endothelial cells, keratinocytes, cardiac myocytes, chondrocytes, synoviocytes, mesenchymal stem cells, neural stem cells, islet cells, hepatocytes, smooth muscle cells, urothelial cells, neurons, Schwann cells and the like.

Embodiments of the present invention are also directed to methods of selectively tailoring cell adhesion to the surface of an implant. According to this aspect of the present invention, a moiety is selected that will promote the adhesion of a particular cell type. The adhesion can be in vitro, i.e. before the implant is implanted, or in vivo, i.e. after the implant is implanted. The moiety is included into a module which is then assembled into a substructure. The substructure is then assembled into a nanometer scale molecular architecture, such as a nanotube. According to one embodiment, the assembly is a self-assembly insofar as the modules are placed into an aqueous medium where they self assemble into a substructure such as a ring structure, such as a rosette, and the ring structures then self-assemble by stacking one on top of another to form a tubular structure, commonly referred to as a nanotube. Such modules, substructures and nanometer scale molecular structures and their self-assembly is described in U.S. Pat. No. 6,696,565, Fenniri et al, *J. Am. Chem. Soc.* 2001, 123, 3854-3855, Moralez et al., *J. Am. Chem. Soc.*, 2005, 127, 8307-8309, and Fine et al., *International Journal of Nanomedicine* 2009:4 91-97 each of which are hereby incorporated by reference in their entireties for all purposes.

According to certain aspects of the present invention, one example of a nanometer scale molecular architecture is a nanotube having nanometer scale dimensions. The nanotubes range in lengths between about 1 nm and about 999 microns, 10 nm and about 10,000 nm, 1 nm to about 500 nm, about 10 nm to about 300 nm, or about 20 nm to about 100 nm. The nanotubes range in diameters between about 1 angstrom and about 100 nm or about 3 nm to about 20 nm. The openings through the nanotubes range in diameters between about 1 angstrom and about 100 nm or about 3 nm to about 20 nm. According to particular embodiments, the nanotubes are monodispersed in diameter for a given functionality attached to a nanotube. By varying the functionalities attached to the nanotube, the diameter can vary between about 1 nm to about 30 nm, or from about 3 nm to about 15 nm. The opening through the nanotube can range in diameter between about 1 nm to about 30 nm, or from about 3 nm to about 15 nm. According to certain embodiments, the opening through the nanotube has a diameter of about 1 nm.

According to one aspect of the present invention, if different cell types are useful in promoting the growth of particular tissue, then a moiety can be selected and included into a substructure for each cell type desired to be adhered to the surface of an implant. In this aspect of the present invention, the nanometer scale molecular architecture can include two or more moieties each selective for a different cell type. The nanometer scale molecular architecture can then be coated on the surface of an implant whether partly or entirely or fashioned into an implant, whether in liquid, putty or solid form. The implant can then be implanted at the desired site within a patient, human or animal, in need of such an implant. Desired cells adhere to the surface of the implant and the desired tissue will grow. In the alternative, the desired cells can be applied and adhered to the surface of the implant before implantation. Such embodiments are useful to promote the growth of tissue on the implant or at the site of implantation. According to aspects of the present invention, the terms adhesion and adherence are used interchangeably and refer to the ability of the cells to remain on the surface of a substrate when subjected to rinsing with saline as known in the art.

Embodiments of the present invention are still further directed to compositions including nanometer scale molecular architectures having functional moieties attached thereto. The functional moieties can have therapeutic or diagnostic applications. The nanometer scale molecular architectures can be used as vehicles for the delivery of functional moieties to a particular site for therapeutic or diagnostic application. According to certain embodiments, the functionalized nanometer scale molecular architectures are mixed with a pharmaceutically acceptable excipient or delivery vehicle and then delivered to the desired location. The nanometer scale molecular architectures of the present invention, such as nanotubes, can mimic the mechanical properties of cartilage when mixed with ceramics and can self-assemble into a material that can mimic the properties of bone. According to one aspect, the nanometer scale molecular architectures are nonfunctionalized or functionalized with moieties useful in orthopedic, cartilage, vascular and wound healing applications, in addition to therapeutic and diagnostic applications.

According to another aspect, modules as described herein which are nonfunctionalized or functionalized for a particular purpose are delivered to a desired site within the body, such as by injection or physical placement as with a putty, where conditions within the body such as temperature and aqueous environment cause the modules to self-assemble into nanotubular structures, preferably solidify, and promote the growth of tissue in the particular environment. According to one aspect, the modules are a component of a composition including a strengthening compound for providing mechanical strength and a matrix material. The composition is placed within the body where conditions within the body such as temperature and aqueous environment causes the modules to self-assemble into nanotubular structures and the composition to cure or polymerize or otherwise solidify into a hardened implant. In one embodiment, the modules are already self-assembled into nanotube structures before delivery to a site within the body. For example, the modules or self-assembled nanotube structures are injected into a fractured bone, cartilage, vascular tissue, heart tissue, nervous system tissue, etc. where the self-assembled nanotubes promote the growth of useful tissue. In addition, the self-assembled nanotubes can be applied to the surface of skin to serve as a wound healing device.

According to certain aspects, methods and compositions are provided for promoting osteoblast differentiation and proliferation, for example at the site of a bone injury or defect or surgical site, including providing an implant with a composition including nanotubes formed from modules according to formula I and/or formula II described herein, nanoparticles, such as nanoparticles of a calcium phosphate and a matrix material, and placing the implant within the body at a site where osteoblast differentiation and proliferation is desired. According to this aspect of the disclosure, the nanometer scale surface geometry of the composition resulting from the nanotubes and the nanoparticles within the matrix promotes the differentiation and proliferation of osteoblasts and the growth of bone tissue.

According to certain aspects, methods and compositions are provided for promoting osteoblast differentiation and proliferation while inhibiting fibroblast proliferation including providing an implant with a composition including nanotubes formed from modules according to formula I and/or formula II described herein, nanoparticles, such as nanoparticles of a calcium phosphate and a matrix material, and placing the implant within the body at a site where osteoblast differentiation and proliferation is desired. According to this aspect of the disclosure, the nanometer scale surface geometry of the composition resulting from the nanotubes and the nanoparticles within the matrix promotes the differentiation and proliferation of osteoblasts and inhibits fibroblast proliferation.

According to certain aspects, methods and compositions are provided for treating bone defects providing an implant with a composition including nanotubes formed from modules according to formula I and/or formula II described herein, nanoparticles, such as nanoparticles of a calcium phosphate and a matrix material, and placing the implant within the body at a site of a bone defect, such as a fracture, or where bone is missing. According to this aspect of the disclosure, the hardened composition with nanometer scale surface geometries resulting from the nanotubes and the nanoparticles within the matrix provides sufficient mechanical support and promotes the differentiation and proliferation of osteoblasts and the deposition of calcium to treat the bone defect. According to certain aspects, the hardened composition with nanometer scale surface geometries resulting from the nanotubes and the nanoparticles within the matrix provides sufficient mechanical support and promotes the differentiation of stem cells into osteoblasts and further promotes proliferation of the osteoblasts and the deposition of calcium to treat the bone defect. According to one aspect, the composition can be in the form of an injectable liquid or shapeable putty and can include stem cells or osteoblasts. Alternatively, stem cells or osteoblasts can be applied to a tissue defect site before application of the composition to the tissue defect site or simultaneously along with the composition to the tissue defect site.

DETAILED DESCRIPTION OF CERTAIN EXEMPLARY EMBODIMENTS

Figure 1A:
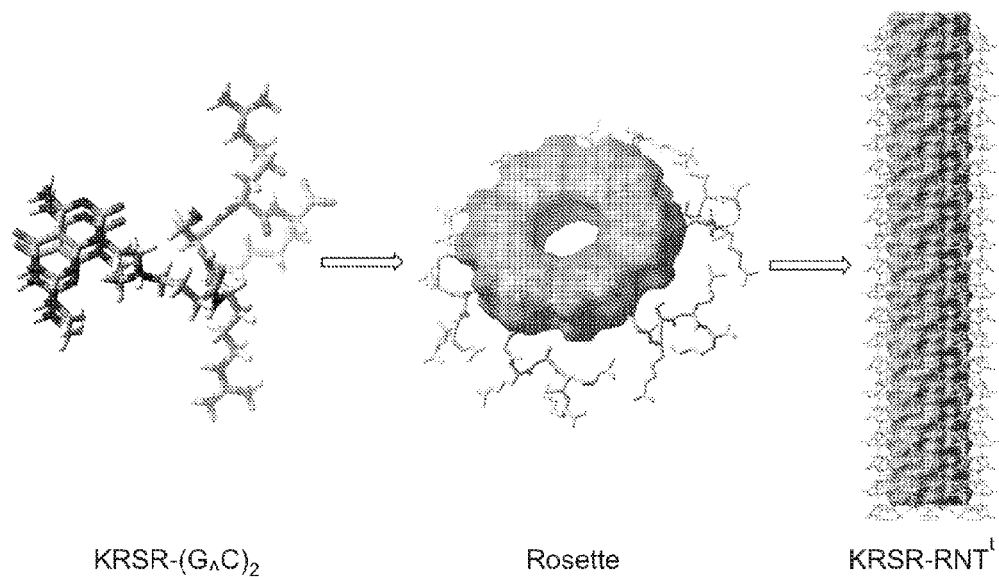
FIG. 1A-1D. Depiction of the self-assembly process of various modules into rosette nanotubes.
Figure 1B:
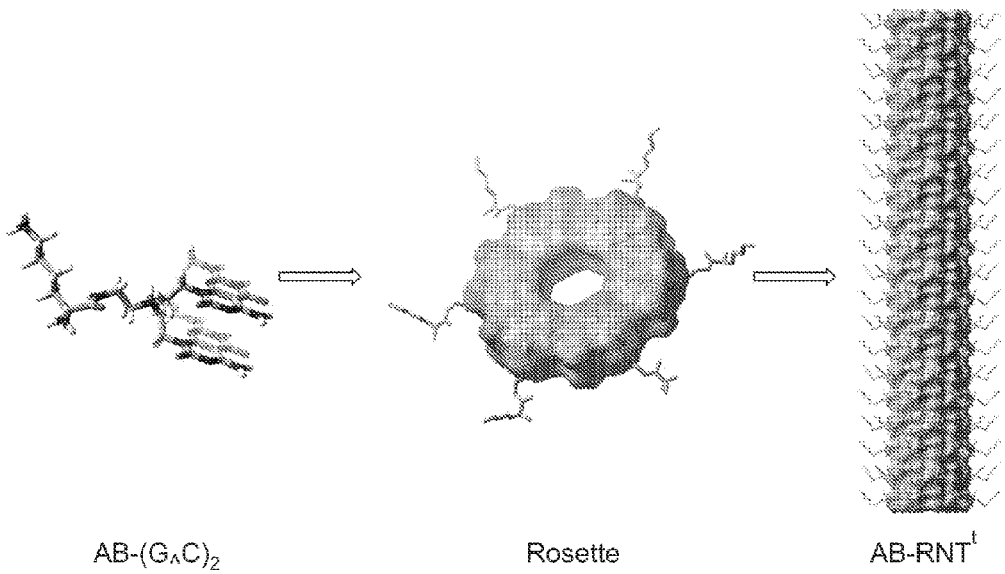
Figure 1C:
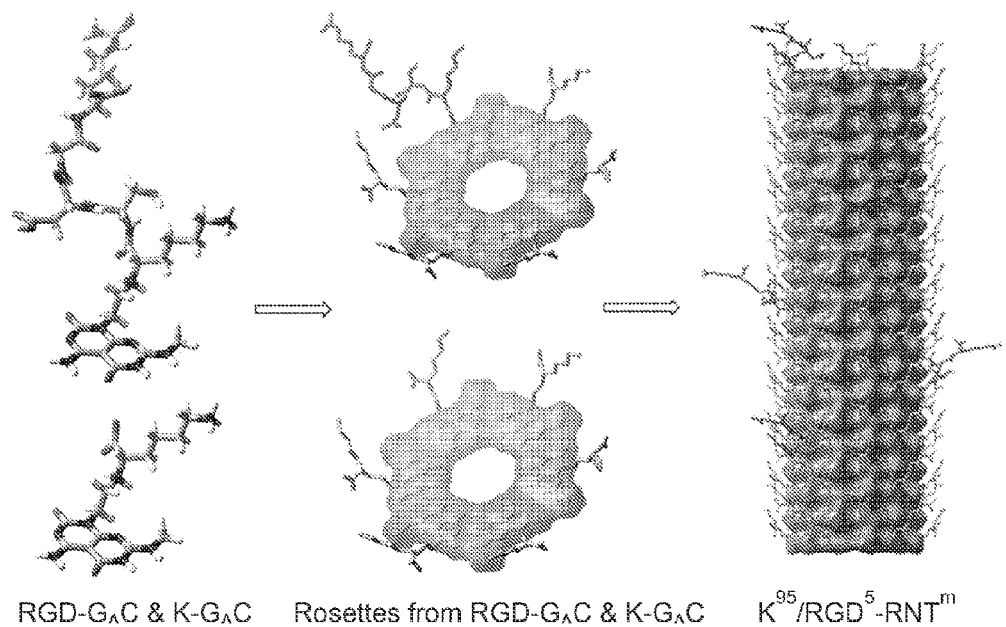
Figure 1D:
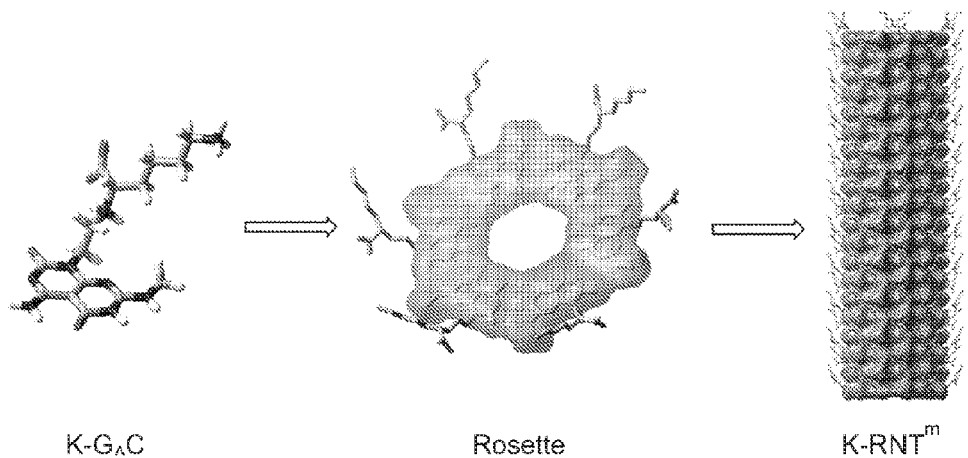

Embodiments of the present invention are based on the discovery that implant surfaces may be tailored to enhance or promote the adhesion of selective cell types using nanometer scale architectures or structures that can preferably be biomimetic, namely having structural similarity to structures found in nature. The nanometer scale structures are formed from modules that preferably self-assemble into substructures, which themselves self-assemble into the nanometer scale architectures or structures, when placed in an aqueous environment such as body fluids. Embodiments of the present invention are further directed to compositions including the nanometer scale structures, such as self assembled nanotubes, a strengthening compound providing mechanical strength, an optional nanoparticle and a matrix material. The compositions can be flowable or moldable such that they can be placed in or occupy or form-fit into a desired site, space or location with the body, such as by syringe, trocar or by hand, and then cured into a hardened structure to provide a nanometer scale surface geometry, to mechanical strength and/or to promote tissue growth or regeneration.

In some embodiments, the viscosity of the composition can be altered to between a flowable liquid and a less flowable putty. As a composition becomes more viscous, it may be more putty-like. Similarly, as a composition becomes less viscous, it may be described as a flowable or liquid material. However, as a person of ordinary skill in the art would be aware, the states of being "flowable" or "putty-like" exist along a continuum.

Modules according to the present invention include compounds of Formula I below:

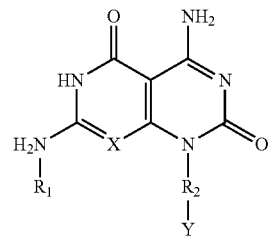

wherein X is CH or nitrogen; Y is absent or an amino acid or polypeptide; $R_2$ is absent or a linker and $R_1$ is aliphatic. According to one aspect, Y is an amino acid or polypeptide having an amino group covalently bound to an α-carbon of the amino acid and the amino group is covalently bound to a linker group $R_2$ for example $(CH_2)_n$; n is an integer of, 1, 2, 3, or 4, and $R_1$ is aliphatic, such as alkyl, straight or branched chain, saturated or unsaturated; and salts thereof. Preferably $R_1$ is $C_1$ to $C_{10}$ alkyl, $C_1$ to $C_5$ alkyl, $C_1$ to $C_3$ alkyl, or methyl. Compounds within the scope of the invention include those where the Y group can be connected to the linker group either by the amino group or the carboxyl group of the amino acid or polypeptide. An exemplary linker group is shown in the formula below.

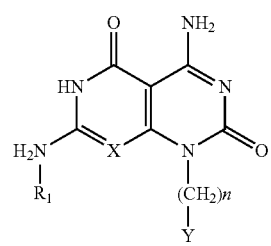

Alternative linker groups $R_2$ can join the Y group to the carbon of the $(CH_2)_n$ group or the N atom either by the amino group or the carboxyl group of the amino acid or polypeptide.

Alternative Linker moieties within the scope of the invention include $NH_3^+$ and the following:

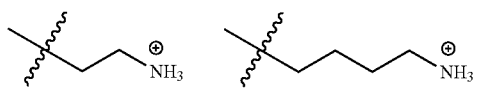

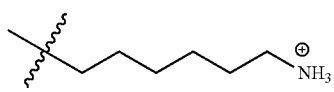

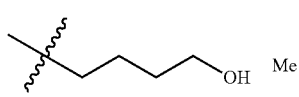

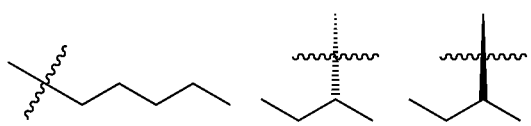

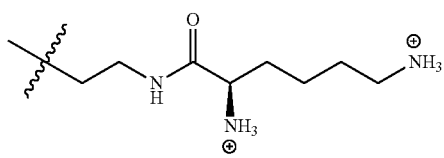

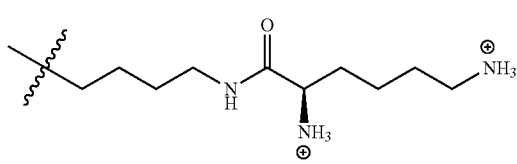

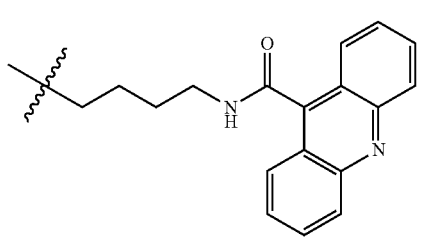

Compounds of Formula I can be prepared by the methods described in U.S. Pat. No. 6,696,565 hereby incorporated by reference herein in its entirety alone or combined with methods known to those of skill in the art.

Modules according to the invention also include compounds of Formula II below:

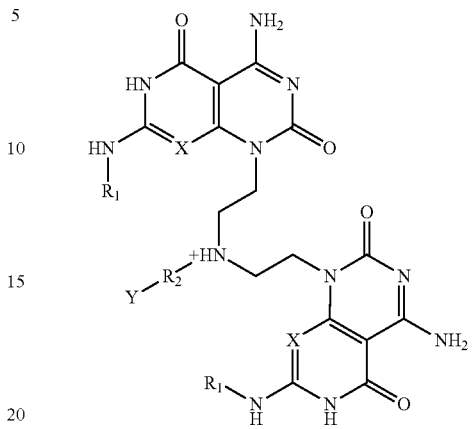

wherein X is CH or nitrogen; Y is absent or an amino acid or polypeptide; $R_2$ is absent or a linker and $R_1$ is aliphatic. According to one aspect, Y is an amino acid or polypeptide having an amino group covalently bound to an α-carbon of the amino acid and the amino group is covalently bound to a linker group $R_2$, such as $(CH_2)_3CO$; and $R_1$ is aliphatic, such alkyl, straight or branched chain, saturated or unsaturated; and salts thereof. Preferably $R_1$ is $C_1$ to $C_{10}$ alkyl, $C_1$ to $C_5$ alkyl, $C_1$ to $C_3$ alkyl, or methyl. An exemplary linker group is shown in the formula below.

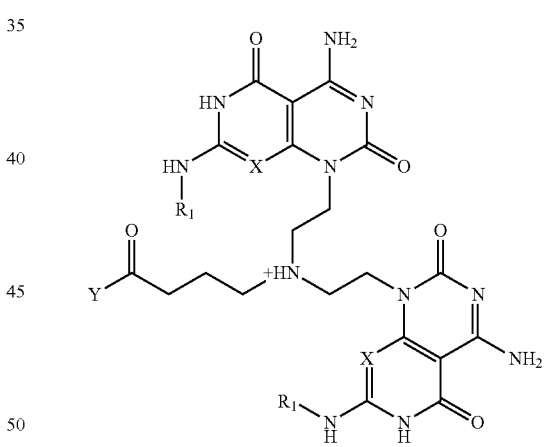

Compounds within the scope of the invention include those where the Y group can be connected to the linker group either by the amino group or the carboxyl group of the amino acid or polypeptide. Alternative linker groups $R_2$ connecting the $NH^+$ group and the Y group include

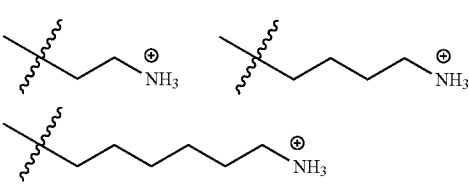

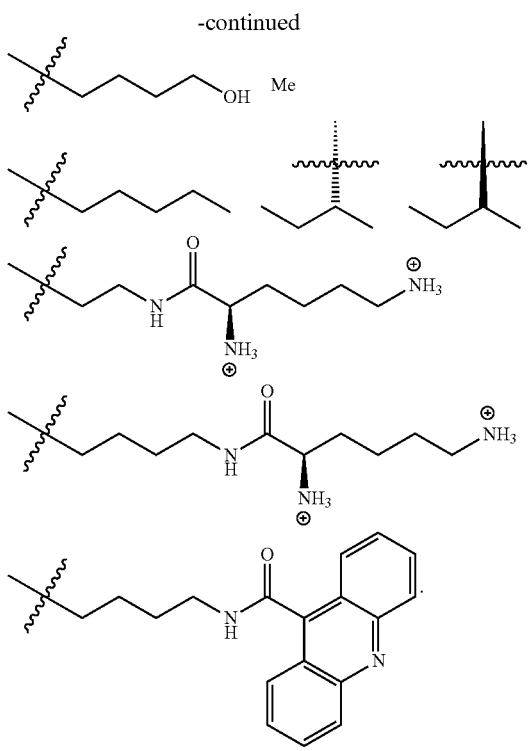

According to certain aspects of the present invention, the structure of Formula II may be referred to as a twin base with a linker (TBL) or twin base linkers insofar as two similar double ring structures are present as shown in Formula II and are linked and further may include an amino acid or polypeptide. However, it is to be understood that the two double ring structures need not be identical insofar as they may have different X and R₁ groups.

Amino acids according to the present invention include the commonly known amino acids such as glycine (Gly, G), alanine (Ala, A), valine (Val, V), leucine (Leu, L), isoleucine (Ile, I), proline (Pro, P), hydroxyproline, phenylalanine (Phe, F), tyrosine (Tyr, Y), tryptophan (Trp, W) cysteine (Cys, C), methionine (Met, M) serine (Ser, S), o-phosphoserine, threonine (Thr, T), lysine (Lys, K), arginine (Arg, R), histidine (His, H), aspartate (Asp, D), glutamate (Glu, E), γ-carboxyglutamate, asparagine (Asn, N), glutamine (Gln, Q) and the like. Amino acids also include stereoisomers thereof and compounds structurally similar to the amino acids or modifications or derivatives thereof. Exemplary amino acids within the scope of the present invention include those that improve adhesion of cells to the surface of a substrate. Accordingly, these amino acids are referred to as cell adhesion promoting amino acids. Specific cell adhesion promoting amino acids include lysine, arginine, serine, glycine, aspartate and the like.

Polypeptides according to the present invention include two or more amino acids covalently linked together. According to one aspect, the two or more amino acids are covalently linked together at least in part by one or more peptide bonds. Exemplary polypeptides within the scope of the present invention include those that improve adhesion of cells to the surface of a substrate. Accordingly, these polypeptides are referred to as cell adhesion promoting polypeptides. Specific cell adhesion promoting polypeptides include lysine-arginine-serine-argine (KRSR), arginine-glycine-aspartate (RGD), isoleucine-lysine-valine-alanine-valine (IKVAV), tyrosine-isoleucine-glycine-serine-arginine (YIGSR) and the like. It is to be understood that other polypeptides having cell adhesion promoting characteristics are within the scope of the present invention which will be recognized by those of skill in the art having the benefit of this disclosure. Without wishing to be bound by scientific theory, adhesion between osteoblasts and the KRSR polypeptide is believed to operate via heparin sulphate proteoglycan mediated mechanisms. See Dee et al., J. Biomed. Mater. Res., 1998; 40:371-377 incorporated herein by reference.

According to aspects of the present invention, modules (compounds) according to Formula I and Formula II self-assemble into substructures also called supermacrocycles which themselves will self-assemble into nanometer scale architectures or structures such as discrete nanotubular assemblies in water or aqueous solutions. Supermacrocycles are defined herein as being a number of organic molecules covalently or noncovalently bound together so as to form a ring structure. For example, compounds of Formula I will self-assemble into a 6-mer ring structure, sometimes referred to as a rosette. The process of forming nanotubes with the modules of the present invention is hierarchical. In particular, the modules of the present invention first self-assemble into supermacrocycles, and then the supermacrocycles self-assembly into nanotubes. Such self-assembly is described in U.S. Pat. No. 6,696,565. For the compounds of Formula II which include twin base linkers, the compounds will also assemble into a 6-mer ring structure. However, a single supermacrocycle formed will include two base layers owing to the presence of the two bases in each of the compound of Formula II.

According to preferred aspects of the present invention, the compounds of Formula I and Formula II include low molecular weight synthetic DNA base analogues referred to by the nomenclature C∧ G. See Fenniri et al, J. Am. Chem. Soc. 2001, 123, 3854-3855. The C∧ G moiety, referred to as a single C∧ G motif, possess the Watson-Crick donor-donor-acceptor of guanine and the acceptor-acceptor-donor of cytosine and undergoes a self-assembly process, fueled by an array of hydrogen bonds, to produce a six-membered supermacrocycle or rosette. Stacking of these rosettes produced a nanotube of very high aspect ratio. Compounds within the scope of the present invention include a twin G^C motif denoted as (C∧ G)₂. Like the single C∧ G motif, the twin C ∧ G motif (C∧ G)₂ also possesses the Watson-Crick donor-donor-acceptor of guanine and the acceptor-acceptor-donor of cytosine and undergoes a self assembly process, fueled by an array of hydrogen bonds, to produce a six-membered supermacrocycle or ring structure (rosette) of twin configuration. Stacking of these twin rosettes produces a nanotube of very high aspect ratio and higher stability.

It should be understood that the above described Formula I and Formula II demonstrate that electrostatic, stacking and hydrophobic interactions can be effectively orchestrated by hydrogen bonds to direct the hierarchical assembly and organization of helical nanotubular architectures in an aqueous milieu. Helical nanotubular architectures within the scope of the present invention include those formed entirely from compounds of Formula I. Helical nanotubular architectures within the scope of the present invention include those formed entirely from compounds of Formula II. Further, helical nanotubular architectures within the scope of the present invention include those formed from one or more of the compounds of Formula I and one or more of the compounds of Formula II. For example, a supermacrocycle ring substructure having particular amino acid or polypeptide side chains formed from the compounds of Formula I can be stacked with a supermacrocycle ring substructure having particular amino acid or polypeptide side chains formed from compounds of Formula II. The rosette substructures formed from the compounds of Formula I and Formula II can be stacked in any desired sequence to form nanotubular structures of the present invention. In this manner, the nanotubular structures possess the amino acids or polypeptides that promote adhesion of selected cells to the nanotubular structures. Utilizing this aspect of the present invention, a wide variety of structurally different modules (i.e. molecules) specific to promote adhesion of certain cells can be synthesized and self-assembled into supermacrocycles and then nanotubular structures according to methods of the present invention.

According to certain preferred aspects of the present invention, a nanotube is prepared that includes K, RGD and KRSR sidechains. The nanotube can be formed from single base ring structures and twin base ring structures in any desired order. The nanotube can have one or more single base ring structures and one or more twin base ring structures. Likewise, a nanotube within the scope of the present invention can include a plurality of single base ring structures formed from compounds of Formula I and a plurality of twin base ring structures formed from compounds of Formula II stacked together, i.e. one next to the other via hydrogen bonding, to form the nanotube.

According to certain aspects, implant surfaces are modified to include the nanotubular structures according to the present invention. Implants within the scope of the present invention have particular uses and applications with orthopedics, cartilage, vascular, neural, skin, bladder, cardiovascular, and the like. Implants according to the present invention can be fashioned from one or more materials known to those skilled in the art including metals, ceramics, polymers and copolymers, Specific implant materials include titanium, stainless steel, Co—Cr—Mo, Ti6Al4V, nitinol, poly-lactic-co-glycolic acid, poly glycolic acid, poly lactic acid, polyurethane, polycaprolactone, silicone, poly vinyl chloride, alumina, titania, hydroxyapatite, calcium phosphates, zirconia, zinc oxide, silver oxide, and the like.

According to certain aspects, the nanotubular structures are directly applied to the surface of an implant as a coating. The coating can include the nanotubular structures themselves and may further include components known to those skilled in the art to form coatings, such as hydrogels (such as poly-HEMA), hydroxyapatite, calcium phosphates, alumina, titania, polymers (such as poly-lactic, polyurethane, polycaprolactone, silicone, poly vinyl chloride) and the like. The coating may also include cell growth promoting components such as proteins (vitronectin, fibronectin, herparin, etc.) and growth factor/cytokines (TGF-β, IGF, NGF, VEGF, BMPs, etc.). The coating may also include therapeutically beneficial ingredients such a drugs, hormones, and antibiotics such as penicillin, streptomycin, gentamycin, dexamethasone, estrogen, bisphosphanates, etc. and the like. The coating may be applied to the implant surface using methods known to those of skill in the art such as direct application, dipping, spraying, painting, electrospinning, cast-mold, heat or thermal processes, spin coating and the like. According to one aspect, the coating is dried to retain the coating on the surface prior to application of cells. In other respects, coatings within the scope of the present invention may be curable onto the surface of an implant using coating compositions and methods known to those of skill in the art.

According to certain aspects, a composition for repair or regeneration of tissue, such as bone tissue, includes one or more nanotubes formed from a plurality of single base ring structures formed from compounds of Formula I. It is to be understood that the compound of formula I need not include a linker or an amino acid or polypeptide and so nanotubes formed from formula I according to the present disclosure need not include a linker or amino acid or a polypeptide. According to an additional embodiment, a composition according to certain aspects can include one or more nanotubes formed from a plurality of twin base ring structures formed from compounds of Formula II. It is to be understood that the compound of formula II need not include a linker or an amino acid or polypeptide and so nanotubes formed from formula II according to the present disclosure need not include a linker or amino acid or a polypeptide. According to a still further embodiment, a composition according to certain aspects can include one or more nanotubes formed from a plurality of single base ring structures formed from compounds of Formula I and a plurality of twin base ring structures formed from compounds of Formula II stacked together, i.e. one next to the other via hydrogen bonding, to form the nanotube. Accordingly, the composition includes compounds of formula I or compounds of formula II which can assemble into nanotubes entirely of compounds of formula I or nanotubes entirely of compounds of formula II or nanotubes formed from a mixture of compounds of formula I and formula II. Modules according to the present disclosure can be present in the composition in an amount between about 1 picogram/ml and about 1 kg/ml, about 1 nanogram/ml and about 1 decigram/ml, about 1 microgram/ml and about 1 centigram/ml, about 1 milligram/ml and about 1 gram/ml, about 0.001 mg/ml to about 1 milligram/ml, about 0.005 milligram/ml to about 0.05 milligram/ml and about 0.01 milligram/ml. Nanotubes according to the present disclosure can be present in the composition in an amount between about 1 picogram/ml and about 1 kg/ml, about 1 nanogram/ml and about 1 decigram/ml, about 1 microgram/ml and about 1 centigram/ml, about 1 milligram/ml and about 1 gram/ml, about 0.001 mg/ml to about 1 milligram/ml, about 0.005 milligram/ml to about 0.05 milligram/ml and about 0.01 milligram/ml, and all ranges and values in between whether overlapping or not.

The composition according to the present disclosure may also include a strengthening compound for providing mechanical strength. The strengthening compound includes phosphates, such as calcium phosphates in the form of granules or powders. Certain calcium phosphates include hydroxyapatite, apatite, oxyapatite, octacalcium phosphate, monocalcium phosphate, dicalcium phosphate, tricalcium phosphate, β-tricalcium phosphate, α-tricalcium phosphate, tetracalcium phosphate, calcium hydrogen phosphate and calcium dihydrogen phosphate and the like and mixtures thereof including all crystalline and amorphous forms of calcium phosphates. The compound for providing mechanical strength can be present in the composition between about 1 picogram/ml and about 1 kg/ml, about 1 nanogram/ml and about 1 decigram/ml, about 1 microgram/ml and about 1 centigram/ml, about 1 milligram/ml and about 1 gram/ml, about 0.001 mg/ml to about 1 milligram/ml, about 0.005 milligram/ml to about 0.05 milligram/ml and about 0.01 milligram/ml, and all ranges and values in between whether overlapping or not.

The composition according to the present disclosure may also include a compound for improving the surface roughness. Such surface roughness is present on the surface of an implant or other structure fashioned from the composition. Compounds for improving surface roughness include compounds having nanometer scale dimensions, such as nanoparticles. Such nanoparticles include calcium phosphate nanoparticles, such as nanoparticles of hydroxyapatite, apatite, oxyapatite, octacalcium phosphate, monocalcium phosphate, dicalcium phosphate, tricalcium phosphate, β-tricalcium phosphate, α-tricalcium phosphate, tetracalcium phosphate, calcium hydrogen phosphate and calcium dihydrogen phosphate and the like and mixtures thereof including all crystalline and amorphous forms of calcium phosphates. The compound for improving surface roughness can be present in the composition between about 0.0001% to about 99.9999%, about 0.01% to about 75%, about 0.1% to about 50%, about 1% to about 40%, about 2% to about 30%, about 5% to about 25%, and about 10% to about 20% and all ranges and values in between whether overlapping or not. The diameter size of the nanoparticles can be between about 1 angstrom and about 999 nm, about 10 angstrom and about 500 nm, about 1 nm and about 100 nm, about 10 nm and about 50 nm, and about 20 nm and about 40 nm and all ranges and values in between whether overlapping or not. According to one aspect, a compound can provide both properties of both mechanical strength and surface roughness. An exemplary compound providing both mechanical strength and surface roughness are nanoparticles of hydroxyapatite. According to one aspect, the amount of hydroxyapatite nanoparticles in the composition can be varied to impart different mechanical strength properties to the implant fashioned from the composition.

The composition according to the present disclosure further includes a matrix material. Suitable matrix materials include polymers and hydrogels. The polymers may be non-degradable or nonerodable or resist degradation or erosion. The polymers may be biodegradable or bioerodable. Exemplary polymers include one or more of polylactic acid, polylactide-coglycolide, polyglycolic acid, polymethylmethacrylate, polyurethane, polycaprolactone, polyethylene, polystyrene polypropylene, polypyrrole, poly(2-hydroxyethyl methacrylate) and the like used as matrix materials and combinations thereof. According to one aspect, the composition is prepared by combining one or more types of polymerizable components such as monomers of the above polymers, such as hydroxyethyl methacrylate (HEMA) monomers, and/or polymers further capable of polymerizing in combination with nanotubes and the compound for providing mechanical strength and/or surface roughness. The polymerizable components are polymerized into a polymer matrix incorporating the nanotubes and the compound for improving mechanical strength and/or surface roughness. Polymerizable components according to the present disclosure can be present in the composition in an amount between about 0.0001% to about 99.9999%, about 0.01% to about 75%, about 0.1% to about 50%, about 1% to about 40%, about 2% to about 30%, about 5% to about 25%, about 10% to about 20%, about 20% to about 90%, about 30% to about 90%, about 40% to about 90%, about 50% to about 90%, about 60% to about 90%, and about 70% to about 90% and all ranges and values in between whether overlapping or not. In this aspect, one embodiment of the composition includes a curable matrix material which cures into a hardened substance. The curable matrix material is cured to form a cured matrix with, for example, nanotubes and nanoparticles of hydroxyapatite embedded therein and present at the surface of the cured matrix. The cured matrix can take any desired shape, such as the shape of a desired mold, for example resembling a tissue defect, such as a bone defect or area of loss of bone or an implant used to reconstruct tissue damage such as a plate or screw. Curable matrix materials include curable resins such as energy curable resins. Curable matrix materials include those that can be cured by exposure to light, such as ultraviolet light, heat, condensation or crosslinking. Curable matrix materials include silicone-based curable materials.

The compositions can further include components typical for polymerization such as an initiator, a crosslinker, a dispersing agent, a rheology modifier, a filler, and other components useful in producing a polymerizable matrix which can be combined, if desired, with biological components such as proteins, cytokines and growth factors. Initiators according to the present disclosure include those known to one of skill in the art, such as azobisisobutyronitrile (AIBN), halogen molecules, azo compounds, organic peroxides and the like, can be present in the composition in an amount between about 0.0001% to about 20%, about 0.001% to about 10%, about 0.01% to about 5%, about 0.1% to about 3%, about 0.1 mg/ml and about 10 mg/ml, about 1 mg/ml and about 5 mg/ml and about 2 mg/ml and about 3 mg/ml and all ranges and values in between whether overlapping or not. Crosslinkers according to the present disclosure include those known to one of skill in the art, such as formalin, formaldehyde, calcium, glutaraldehyde and the like, can be present in the composition in an amount between about 0.0001% to about 99.9999%, about 0.01% to about 75%, about 0.1% to about 50%, about 1% to about 40%, about 2% to about 30%, about 5% to about 25%, about 10% to about 20%, about 20% to about 90%, about 30% to about 90%, about 40% to about 90%, about 50% to about 90%, about 60% to about 90%, and about 70% to about 90% and all ranges and values in between whether overlapping or not.

The compositions can further include excipients, such as saccharide excipients like monosaccharides, disaccharides, water dispersible oligosaccharides and polysaccharides.

The compositions can further include binders known to those of skill in the art such as calcium sulfates and calcium silicates. Exemplary binders include calcium sulfate hemihydrate ($CaSO_4 \cdot \frac{1}{2}H_2O$), which reacts with water to form calcium sulfate dihydrate ($CaSO_4 \cdot 2H_2O$) upon mixing, and tricalcium silicate $(CaO)_3 \cdot SiO_2$ (or $Ca_3SiO_5$).

According to one aspect of the present disclosure, an exemplary solidified composition includes pHEMA, about 20% HA, about 3 mg/ml AIBN and about 0.01 mg/ml of a compound of formula II. Exemplary flowable formulations include pHEMA, about 20%-30% water $H_2O$, about 2-3 mg/ml AIBN and about 0.01 mg/ml of a compound of formula II. HA may optionally be present in the flowable formulation.

According to certain aspects, cells can be adhered onto the surface of the implants that have been modified with the nanotubular structures of the present invention. Cells within the scope of the present invention include osteoblasts, fibroblasts, endothelial cells, stem cells, keratinocytes, cardiac myocytes, chondrocytes, synoviocytes, mesenchymal stem cells, neural stem cells, islet cells, hepatocytes, smooth muscle cells, urothelial cells, neurons, Schwann cells, etc. and the like. Preferred cells include osteoblasts insofar as the coatings of the present invention convert conventional implant surfaces to biomimetic nanostructured interfaces that enhance cell adhesion and osseointegration.

In certain other embodiments, the modules or self-assembled nanotubular structures can be combined with components or suitable medium to produce a composition for an injectable formulation or putty. The composition may also include cell growth promoting components such as proteins (vitronectin, fibronectin, herparin, etc.) and growth factor/cytokines (TGF-β, IGF, NGF, VEGF, BMPs, etc.). The composition may also include therapeutically beneficial ingredients such a drugs, hormones, antibiotics, such as penicillin, streptomycin, gentamycin, dexamethasone, estrogen, bisphosphanates, etc. and the like. The composition may also include diagnostically beneficial ingredients such a radiolabels, magnetic particles, fluorescent labels, and radio-opaque labels.

The bioactive agent, when present, may for example be a growth factor such as bone morphogenetic protein (e.g., BMP-1, BMP-2, BMP-3, BMP-4, BMP-5, BMP-6, BMP-7, BMP-8, BMP-9, BMP-10, BMP-11, BMP-12, BMP-13, BMP-14, BMP-15), and one or more different growth factors may be included in the implant. When including a growth factor, one may first manually mix the composition and then soak the composition in a solution that comprises the growth factor. This resulting composition may be delivered to an end user as a pre-mixed formulation.

In some embodiments, the composition that will form the implant comprises collagen, such as Type I bovine collagen. In other embodiments there is an absence of collagen. Further, in some embodiments, the composition that will form the implant contains one or more non-collagenous fibrous components, such as hydroxybutyrate and/or a cross-linked alginate. These non-collagenous fibrous components may enhance osteoconductivity. In some embodiments the composition contains both crosslinked and non-crosslinked alginates. In other embodiments, the composition contains no alginates, only crosslinked alginates or only non-crosslinked alginates.

In some embodiments, the composition may include one or more bioactive glasses. A bioactive glass, is generally composed of the elements silicon, calcium, phosphorus, sodium, and oxygen, although other elements such as boron, potassium, magnesium and fluorine for example, may be added to modify various characteristics, as disclosed in U.S. Pat. Nos. 4,103,002, 4,775,646 and 4,851,046, the disclosure of which is incorporated herein by reference. A representative bioactive glass composition may comprise for example 40 to 52 wt. % $SiO_2$, 10 to 50 wt. % CaO, 10 to 35 wt. % $Na_2O$, 2 to 8 wt. % $P_2O_5$, 0 to 25 wt. % $CaF_2$, 0 to 10 wt. % $B_2O_3$, 0 to 8 wt. % $K_2O$, and 0 to 5 wt. % MgO. As a preferred example, one specific bioactive glass composition, marketed under the brand name BIOGLASS®, has a composition of approximately 21% silicon, 18% calcium, 18% sodium, 3% phosphorus, and 40% oxygen (by weight percent).

Additionally, in some embodiments, the compositions that will form the implants contain neither human nor animal tissue derived components. By omitting these types of components, the risk of disease transmission can be reduced, and particularly in embodiments that contain no collagen, the implants will be particularly advantageous for use in applications in which collagen containing products are prohibited.

In some embodiments, the compositions that will form the implants will also contain a liquid component such as water. As a practical matter, the composition that is to be shaped and implanted may be supplied to a provider in a ready to use formulation. For example, a composition that is to be molded to a desired implant shape may be prehydrated and supplied with a syringe or preloaded in a syringe. In some embodiments, hydration is accomplished with sterile water.

In some embodiments, the implant is designed to be flowable through a syringe as well as to be malleable and cohesive such that it may be intraoperatively shaped and molded to conform to a surgical site. Because these characteristics are present, a health care provider will have a longer time span in which to shape the implant for use in each application. Thus, the composition can be dispensed from the syringe, molded and then inserted by hand into a desired site.

The implant may be combined at an operative site with one or more of bone marrow aspirate, autograft tissue, allograft tissue and synthetic grafting agents. It also may be of use in a number of different locations, including but not limited to the spine, orthopedic sites, and COMF. In some embodiments, the implant of the present invention is particularly useful for filling of periodontal defects, filling of dental extraction sockets, filling of cystic defects, sinus lifts, alveolar ridge augmentation, oral or maxillofacial augmentation or reconstruction, interbody or posterior-lateral applications, non-loaded bearing defects, and voids caused by trauma. In these and other applications, the implant may be used with or without internal fixation.

In some embodiments, the components of the composition of the implant are such that there is no setting time. Thus, in some embodiments there may be no stabilizers (also known as stabilizing agents). In other embodiments the implant may further contain a stabilizing agent, which may be a material that will allow a calcium phosphate mineral to set when reacted after the calcium phosphate has been stored for a predetermined amount of time. In some embodiments, this time period is at least one month, at least two months, at least three months, at least four months, at least five months, at least six months. In some embodiments, this time period is less than seven months, less than six months, less than five months, less than four months, less than three months, or less than two months.

Examples of the stabilizing agents that can be used in accordance with the present invention, include but are not limited to MgO, MgO2, Mg(OH)2, MgHPO4, MgHPO4.3H2O, MgHPO4.7H2O, Mg3(PO4)2, Mg3(PO4)2.4H2O, Mg3(PO4)2.8H2O, Mg3(PO4)2.22H2O, MgCO3, MgCO3.3H2O, MgCO3.5H2O, 3MgCO3Mg(OH)23H2O, MgCO3Mg(OH)2.3H2O, Mg(C3H5O3)2.3H2O, MgC2O42H2O, Mg(C4H4O6)2.4H2O, MgCO3CaCO3, Mg2P2O7, Mg(C12H23O2)22H.2O, Mg(C14H27O2)2, Mg(C18H33O2)2, or Mg(C18H35O2)2 and/or a mixture thereof. In some embodiments the preferred stabilizing agent is magnesium oxide.

In some embodiments the stabilizing agent is present in an amount of from about 10 ppm to about 60 ppm or from about 30 pm to about 50 ppm or from about 35 ppm to about 45 ppm relative to the total weight of the calcium phosphate.

In some embodiments one or more of the following additives is included in addition to the growth factor referenced above or instead of the growth factor referenced above: proteins, X-ray opacifying agents, medicaments, supporting or strengthening filler materials, crystal growth adjusters, viscosity modifiers, pore forming agents and mixtures thereof.

The implant may also contain one or more antibiotics. Examples of antibiotics that may be used, include but are not limited to nitroimidazole antibiotics, tetracyclines, penicillins, cephalosporins, carbopenems, aminoglycosides, macrolide antibiotics, lincosamide antibiotics, 4-quinolones, rifamycins and nitrofurantoin. Suitable specific compounds include, without limitation, ampicillin, amoxicillin, benzylpenicillin, phenoxymethylpenicillin, bacampicillin, pivampicillin, carbenicillin, cloxacillin, cyclacillin, dicloxacillin, methicillin, oxacillin, piperacillin, ticarcillin, flucloxacillin, cefuroxime, cefetamet, cefetrame, cefixine, cefoxitin, ceftazidime, ceftizoxime, latamoxef, cefoperazone, ceftriaxone, cefsulodin, cefotaxime, cephalexin, cefaclor, cefadroxil, cefalothin, cefazolin, cefpodoxime, ceftibuten, aztreonam, tigemonam, erythromycin, dirithromycin, roxithromycin, azithromycin, clarithromycin, clindamycin, paldimycin, lincomycirl, vancomycin, spectinomycin, tobramycin, paromomycin, metronidazole, tinidazole, ornidazole, amifloxacin, cinoxacin, ciprofloxacin, difloxacin, enoxacin, fleroxacin, norfloxacin, ofloxacin, temafloxacin, teromycin, doxycycline, minocycline, tetracycline, chlortetracycline, oxytetracycline, methacycline, rolitetracyclin, nitrofurantoin, nalidixic acid, gentamicin, rifampicin, amikacin, netilmicin, imipenem, cilastatin, chloramphenicol, furazolidone, nifuroxazide, sulfadiazin, sulfametoxazol, bismuth subsalicylate, colloidal bismuth subcitrate, gramicidin, mecillinam, cloxiquine, chlorhexidine, dichlorobenzylalcohol, methyl-2-pentylphenol and any combination thereof.

The antibiotics may be integrated into the composition in the same way that, the growth factor is integrated into it. Further, an antibiotic may be included instead of or in addition to a growth factor.

Suitable anti-inflammatory compounds include both steroidal and non-steroidal structures. Suitable non-limiting examples of steroidal anti-inflammatory compounds are corticosteroids such as hydrocortisone, cortisol, hydroxyltriamcinolone, alpha-methyl dexamethasone, dexamethasonephosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, difluorosone diacetate, fluocinolone, fluradrenolone acetonide, medrysone, amcinafel, amcinafide, betamethasone and the balance of its esters, chloroprednisone, chloroprednisone acetate, clocortolone, clescinolone, dichlorisone, difluprednate, fluclorinide, flunisolide, fluorometholone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone. Mixtures of the above steroidal anti-inflammatory compounds may also be used.

Non-limiting examples of non-steroidal anti-inflammatory compounds include nabumetone, celecoxib, etodolac, nimesulide, apasone, gold, oxicams, such as piroxicam, isoxicam, meloxicam, tenoxicam, sudoxicam, and CP-14,304; the salicylates, such as aspirin, disalcid, benorylate, trilisate, safapryn, solprin, diflunisal, and fendosal; the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; the fenamates, such as mefenamic, meclofenamic, flufenamic, niflumic, and tolfenamic acids; the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and the pyrazoles, such as phenylbutazone, oxyphenbutazone, feprazone, azapropazone, and trimethazone.

The various compounds encompassed by anti-inflammatories are well-known to those skilled in the art. For detailed disclosure of the chemical structure, synthesis, side effects, etc. of non-steroidal anti-inflammatory compounds, reference may be had to standard texts, including Anti-inflammatory and Anti-Rheumatic Drugs, K. D. Rainsford, Vol. I-III, CRC Press, Boca Raton, (1985), and Anti-inflammatory Agents, Chemistry and Pharmacology 1, R. A. Scherrer, et al., Academic Press, New York (1974), each incorporated herein by reference.

Mixtures of these non-steroidal anti-inflammatory compounds may also be employed, as well as the pharmacologically acceptable salts and esters of these compounds.

In addition, so-called "natural" anti-inflammatory compounds may be useful. Such compounds may suitably be obtained as an extract by suitable physical and/or chemical isolation from natural sources (e.g., plants, fungi, by-products of microorganisms). Suitable non-limiting examples of such compounds include candelilla wax, alpha bisabolol, aloe vera, Manjistha (extracted from plants in the genus *Rubia*, particularly *Rubia Cordifolia*), and Guggal (extracted from plants in the genus *Commiphora*, particularly *Commiphora Mukul*), kola extract, chamomile, sea whip extract, compounds of the Licorice (the plant genus/species *Glycyrrhiza glabra*) family, including glycyrrhetic acid, glycyrrhizic acid, and derivatives thereof (e.g., salts and esters). Suitable salts of the foregoing compounds include metal and ammonium salts. Suitable esters include $C_2$-$C_2$4 saturated or unsaturated esters of the acids, preferably $C_{10}$-$C_2$4, more preferably $C_{16}$-$C_2$4. Specific examples of the foregoing include oil soluble licorice extract, the glycyrrhizic and glycyrrhetic acids themselves, monoammonium glycyrrhizinate, monopotassium glycyrrhizinate, dipotassium glycyrrhizinate, 1-beta-glycyrrhetic acid, stearyl glycyrrhetinate, and 3-stearyloxy-glycyrrhetinic acid, and disodium 3-succinyloxy-beta-glycyrrhetinate.

Generally, anti-inflammatory non-steroidal drugs are included in the definition of pain-reducing agents because they provide pain relief. In addition, suitable pain-reducing agents include other types of compounds, such as, for example, opioids (such as, for example, morphine and naloxone), local anaesthetics (such as, for example, lidocaine), glutamate receptor antagonists, α-adrenoreceptor agonists, adenosine, canabinoids, cholinergic and GABA receptors agonists, and different neuropeptides. A detailed discussion of different analgesics is provided in Sawynok et al., (2003) Pharmacological Reviews, 55:1-20, the contents of which are incorporated herein by reference.

Compositions of the present disclosure may also include cells. Suitable cells include, without limitations, stem cells, e.g., embryonic or adult stem cells, which can conveniently be derived from the blood or bone marrow of the patient or from an allogeneic source, which preferably is immunologically compatible with the patient. Other suitable cells may include chondrogenic or osteogenic precursor cells. A person of the ordinary skill in the art will appreciate that the cells may be genetically modified (e.g., overexpressing certain proteins, or having expression of certain proteins inhibited). Methods of creating such genetically modified cells are within knowledge and expertise of the person of ordinary skill in the art.

Compositions of the present disclosure may also include nucleic acid sequences. Suitable nucleic acid sequences include, without limitation, cDNA sequences encoding the at least one bioactive factor of a proteinaceous nature. These cDNAs may be included within respective vectors (e.g., AAV). In another embodiment, the nucleic acid sequences may be siRNAs or shRNAs or nucleic acid sequences encoding for such siRNAs or shRNAs. These siRNAs and shRNAs may be used in embodiments wherein it is desirable to inhibit expression of certain genes, such as, for example inflammatory protein genes such as TNF, IL-1, IL-6, and BMP inhibitor proteins such Noggin and Chordin, and intracellular BMP inhibitors SMADS. A person of ordinary skill in the art will appreciate that the nucleotide sequences for such genes are available in publicly-accessible databases, including, without limitation, Genbank. Further, the criteria for the siRNA selection have been also described in the art. Accordingly, a person of ordinary skill in the art will have sufficient knowledge and expertise in preparing such siRNAs or shRNAs.

The methods of incorporating the at least one bioactive factor are also known in the art. In one embodiment, the composition may be soaked in a solution of the at least one bioactive factor before implantation. In some embodiments, depending on the properties of the at least one bioactive factor, the composition may be soaked in the solution for 1-60 minutes before the implantation. The at least one bioactive factor may also be dripped, brushed, or sprayed onto the composition of the present disclosure or implants including the composition of the present disclosure.

If the at least one bioactive factor includes cells, the cells may be re-suspended in a volume of media (e.g., Dulbecco's Modified Eagle's Medium) and cultured with the compositions described herein. Due to the properties of the surface of the composition and, in certain instances, the porosity of the composition, the cells will populate the external surfaces of the composition and its internal voids. Optimal loading conditions (e.g., medium composition, shaking, if necessary) may be easily determined by the person of ordinary skill in the art. Further, the composition may be wetted with an aspirate from the patient's bone marrow, thus allowing the bone marrow cells to populate the voids and pores within the composition.

EXAMPLES

The following examples are specific embodiments of the present invention but are not intended to limit it.

Example 1

Synthesis of Polypeptide-Functionalized Twin Base Compound of Formula II

Figure 1E:
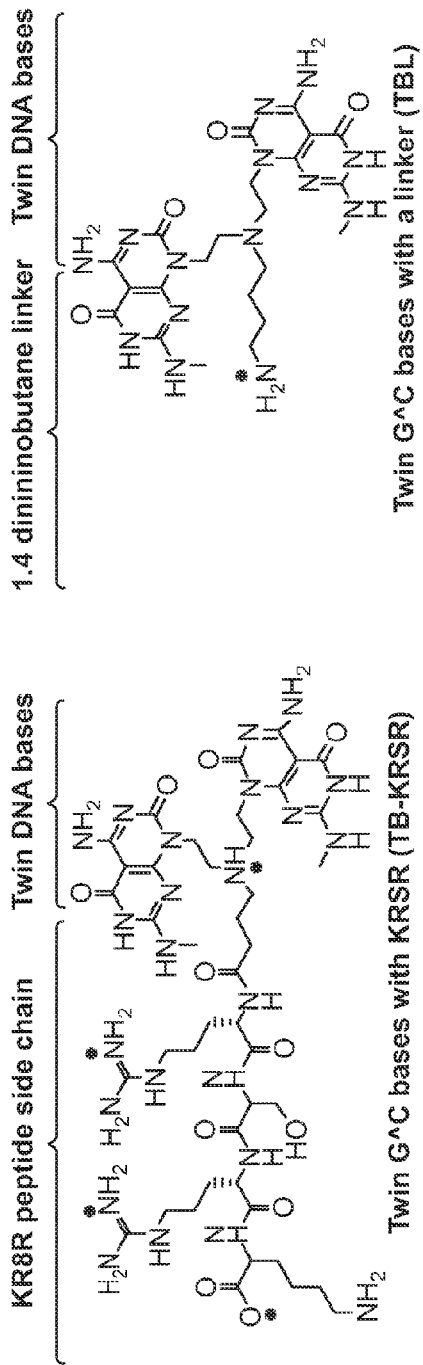
FIG. 1E-1G. Twin base RNTs. (E) TB-KRSR; (F) TBL; (G) The self-assembly process of twin C∧G bases into a rosette nanotube.
Figure 1F:
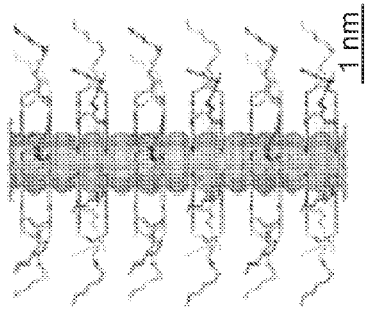
Figure 1G:
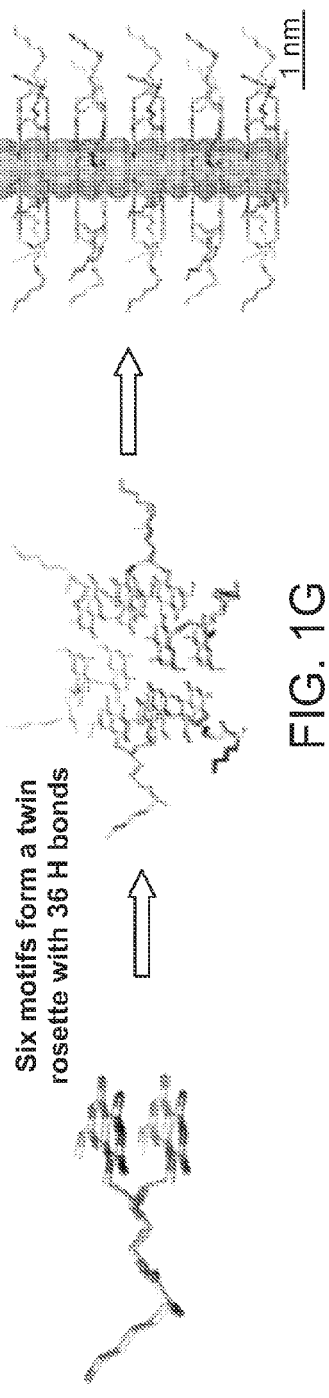

All the reagents and solvents used in the following synthesis were obtained from Aldrich, Novabiochem, BaChem, Fluka, Fisher Scientific of Advanced ChemTech, and were used without further purification. Reagent grade dichloromethane, methanol and ether were purified on an MBraun solvent purification system. Modules of twin base pairs functionalized with the polypeptide KRSR, i.e. KRSR-(C∧G)$_2$ and modules of twin base pairs functionalized with aminobutane, i.e. AB-(C∧G)$_2$ are shown in FIG. 1A-1D and were synthesized according to the procedures illustrated in FIG. 2A and FIG. 2B, respectively. FIG. 1E-1G depicts twin base RNTs TB-KRSR (E); TBL (F); the self-assembly process of twin C∧G bases into a rosette nanotube (G).

Standard Fmoc [see Carpino et al., *J. Org. Chem.* 1972; 37(22):3404-3409 and Atherton et al., *J. Chem. Soc., Chem. Commun.*, 1978:537-539 each hereby incorporated by reference in their entireties] solid-phase peptide synthesis was used to prepare the Wang resin-supported KRSR peptide. SPPS [see Merrifield, *J. Am. Chem. Soc.* 1963; 85(14):2149-2154 hereby incorporated by reference in its entirety] is a simple procedure, which allows rapid synthesis of peptides in good yields. This method eliminates solubility, purification and racemization issues, common with solution phase peptide synthesis. In general, the carboxyl groups of the protected amino acid Fmoc-Lys(Boc)-OH was first coupled to the hydroxyl groups on the Wang resin. The Fmoc group of the lysine anchored to the resin was removed under basis conditions, after which it was reacted with the second amino acid Fmoc-Arg(PBf)-OH. The same procedure was repeated for subsequent amino acid couplings with Fmoc-Ser(tBu)-OH, Fmoc-Arg(PBf)-OH and Fmoc-γ-Abu-OH. The terminal Fmoc group on the Wang resin-supported peptide was removed and the resulting free amine was reductively coupled to C∧G aldehyde. The desired motif KRSR-(C∧G)$_2$ was obtained upon deprotection and cleavage from the resin under strongly acidic conditions.

Figures 2, 2A:
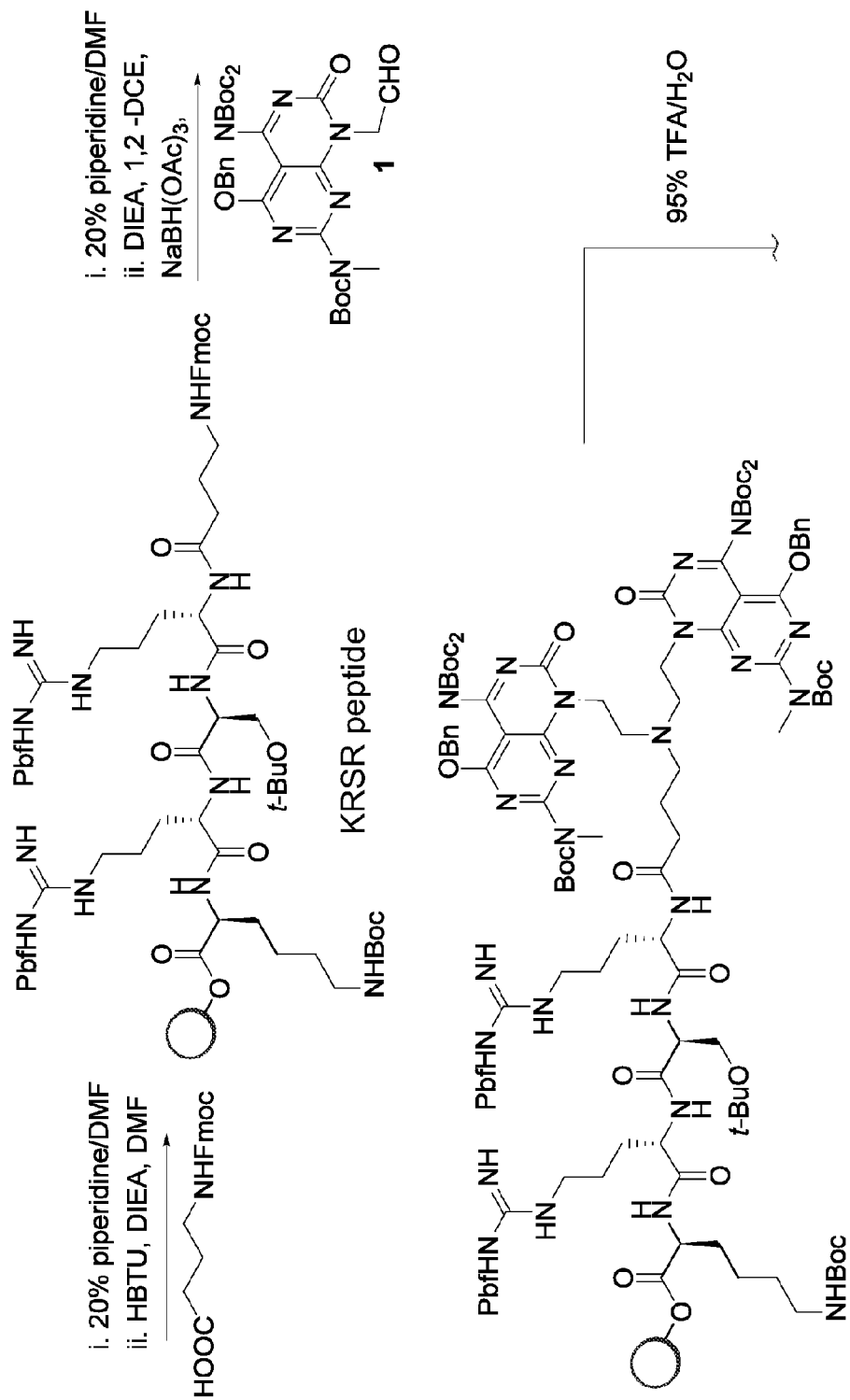
FIG. 2. A synthetic scheme of (A) Wang resin protected KRSR peptide coupling onto the twin C∧G bases (TB-KRSR) and (B) twin C∧G bases with a 1,4-diaminobutane linker (TBL).

More specifically and with reference to FIG. 2A, to anchor the first amino acid to the resin, Fmoc-amino acid (4 eq), p-dimethylaminopyridine (DMAP) (1 eq) in N,N-dimethylformamide (DMF, 8 mL) were poured into a disposable plastic syringe containing the Wang resin (1 eq). After activating the resin for 20 min, N,N'-diisopropylcarbodiimide (DIC, 4 eq) was added to the vessel and the reaction mixture was shaken for 6 hours (hr). The resin was then filtered under vacuum, washed with 10 mL each of CH$_2$Cl$_2$, MeOH, DMF and then treated with 50:50 acetic anhydride/pyridine (5 mL, 1×10 min and 2×20 min) to cap the unreactive hydroxyl groups. The resin was then filtered and washed with (3×10 mL) with DMF, CH$_2$Cl$_2$, and MeOH and dried under vacuum. The substitution degree (0.52 mmol/g) was determined by spectroscopic quantification of the fulvene-piperidine adduct at 301 nm on a resin sample.

Subsequent amino acids were coupled as follows: the Fmoc protecting group was removed by incubation of the resin in 20% piperidine/DMF (5 mL, 1×5 min, 1×30 min). The resulting peptidyl resin was washed with 10 mL each of CH$_2$Cl$_2$, MeOH, DMF. N-ethyl-N-isopropylpropan-2-amine (DIEA, 8 eq) was added to a mixture of amino acid (4 eq relative to resin loading) and 2-(1H-Benzotriazol-1-yl)-1,1,3,3-tetramethyluronium hexafluorophosphate (HBTU, 4 eq) in DMF solution, and the mixture was activated by shaking for 3 minutes (min). The resulting mixture was then added to the peptidyl resin and was shaken for 3 hours (h). The peptidyl resin was then drained and washed with 10 mL of each of CH$_2$Cl$_2$, MeOH and DMF. The absence of free amino groups was confirmed with the Kaiser test [see Kaiser et al., Anal. Biochem, 1970, 24, 595-598 hereby incorporated by reference in its entirety]. The Fmoc protecting group was removed by incubation of the resin in 20% piperidine/DMF (5 mL, 1×5 min, 1×30 min). The resulting peptidyl resin was washed with 10 mL each of CH$_2$Cl$_2$, MeOH, and DMF.

To prepare KRSR-(C∧G)$_2$, the Wang resin-supported KRSR peptide was coupled to the C∧G aldehyde 1 (FIG. 2A). The C∧G aldehyde 1 (4 eq relative to resign loading) was added to the peptidyl resin in 1,2-dichloroethane (1,2-DCE, 5 mL), and the mixture was shaken for 4 h. NaBH(OAc)$_3$ (2 eq) and DIEA (4 eq) were then added and the mixture was shaken for 36 h, after which another 2 eq NaBH(OAc)$_3$ and 4 eq of DIEA were added and shaken for an additional 36 h. The resin was drained and the resulting peptidyl-resin was washed CH$_2$Cl$_2$, MeOH and DMF (4×10 mL each), and dried under vacuum. Cleavage from the resin and deprotection was achieved by treating the resin with 95% TFA/water for 2 h. The beads were filtered over celite and the resulting filtrate was concentrated to a viscous liquid (rotavap). Cold Et$_2$O was then added to precipitate crude KRSR-(C∧G)$_2$, which was isolated by centrifugation. The supernatant liquid was removed by decantation. The residual solid was resuspended in Et$_2$O (2×15 mL), sonicated, and centrifuged. The precipitate was dried to yield the desired KRSR-(C∧G)$_2$ as an off-white powder.

The synthetic scheme (FIG. 2B) was carried out for preparation of module AB-(C∧G)$_2$ from the C∧G aldehyde and t-butyl 4-aminobutylcarbamate via two consecutive reductive amination reactions followed by removal all protecting groups. Specifically, to prepare AB-(C∧G)$_2$, commercially available amine 2 (1.00 g, 1.57 mmol) was added to a solution of C∧G aldehyde 1 (0.148 g, 0.784 mmol) in 1,2 DCE (10 mL) at room temperature under $N_2$ and stirred for 30 min. NaBH(OAc)$_3$ (0.395 g, 1.88 mmol) was added and the resulting mixture was stirred for an additional 15 h. The reaction mixture was diluted with $CH_2Cl_2$ (50 mL) and then washed with water (10 mL), brine (15 mL), dried over $Na_2SO_4$ and concentrated (rotavap) Compound 3 (1.36 g, 93%) was obtained as a white foam after silica gel flash chromatography (0-10% MeOH/EtOAc). C∧G aldehyde 1 (0.100 g, 0.155 mmol) was then added to a solution of monomer 3 (0.126 g, 0.155 mmol) in 1,2 DCE (10 mL) at room temperature under $N_2$ and stirred for 30 min. NaBH(OAc)$_3$ (0.039 g, 0.186 mmol) was added and the resulting mixture was stirred for an additional 15 h. The reaction mixture was diluted with $CH_2Cl_2$ (50 mL) and washed with water (10 mL), brine (15 mL), dried over $Na_2SO_4$ and concentrated. Compound 4 (0.204 g, 91%) was obtained as a white foam after silica gel flash chromatography (0-50% EtOAc/Hexanes). Compound 4 (0.106 g, 0.074 mmol) was stirred in 95% TFA/thioanisole (10 mL) for 72 h. $Et_2O$ (60 mL) was then added to the reaction mixture and the precipitate formed, was centrifuged down. The residual solid was resuspended in $Et_2O$, sonicated and centrifuged down. This process was repeated until no UV-active product could be detected in the $Et_2O$ wash (by spotting on a silica plate). The resulting TFA salt of AB-(C∧G)$_2$ was dried and then dissolved in 1M hydrochloric acid (10 mL), followed by removal of the solvent under reduced pressure. This process was repeated twice before the solid was dried under vacuum for 72 h to give the HCl salt of AB-(C∧G)$_2$ as an off-white powder in quantitative yield.

Example 2

Self-Assembly of Rosette Nanotubes (RNTs) in Water

Stock solutions (1 mg/mL) of RNTs assembled from functionalized twin bases AB-(C∧G)$_2$ and KRSR-(C∧G)$_2$ (referred as AB-RNT$^t$ and KRSR-RNT$^t$ respectively) were prepared by dissolving the corresponding motifs (AB-(C∧G)$_2$ isolated either as a TFA or HCl salt) in deionized water (dH$_2$O). The stock solutions were then diluted to 0.1 mg/mL and 0.01 mg/mL solutions for comparison purposes. RGD-C∧G and K-C∧G were prepared as previously reported [see Fenniri et al., *J. Am. Chem. Soc.* 2001; 123: 3854-3855 and Zhang et al., *Biomaterials* 2009; 30(7):1309-1320 each hereby incorporated by reference in its entirety]. K-RNT$^m$ refer to RNTs assembled from functionalized mono base
K-C∧G. K$^{99}$/RGD$^1$-RNT$^m$ and K$^{95}$/RGD$^5$-RNT$^m$ refer to RNTs co-assembled from mono bases K-C∧G and RGD-C∧G in a molar ratio of 99% and 95%, respectively. All the RNT solutions were filtered through a 0.22 μm syringe filter.

Example 3

Characterization of KRSR-(G^C)$_2$ and AB-(G^C)$_2$

KRSR-(C∧G)$_2$, AB-(C∧G)$_2$ and all intermediate molecules leading to them were characterized by $^1$H/$^{13}$C NMR spectroscopy, high-resolution electrospray ionization mass spectrometry (HR EI-MS), and elemental analysis. $^1$H/$^{13}$C spectra were recorded with the solvent as an internal reference on Varian Inova NMR spectrometers (500 or 600 MHz) at Canada's National Institute for Nanotechnology or Department of Chemistry, University of Alberta. The NMR data are presented as follows: chemical shift, peak assignment, multiplicity, coupling constant, and integration. The mass spectra were obtained from the Mass Spectrometry Laboratory at the Department of Chemistry, University of Alberta. These data are summarized in Tables 1 and 2 below.

TABLE 1

$^1$H NMR, $^{13}$C NMR, HRMS and elemental analysis data of TB-KRSR
TB-KRSR Characterization Data

| | |
|---|---|
| $^1$H NMR (DMSO; 600 MHz) | 12.34 (bs, 2H), 9.24 (bs, 2H), 9.06 (bs, 2H), 8.97 (m, 1H), 8.26 (m, 2H), 8.13 (m, 2H), 8.08-7.98 (m, 2H), 7.65 (bs, 3H), 7.54-7.50 (m, 2H), 7.39-7.16 (bs, 4H), 7.10-6.65 (bs, 4H), 4.43 (m, 4H), 4.35-4.27 (m, 3H), 4.12 (m, 1H), 3.62 (m, 1H), 3.59-3.47 (m, 4H), 3.33 (m, 1H), 3.08 (bs, 5H), 2.91 (d, 6H, J = 4.2 Hz), 2.74 (m, 4H), 2.34-2.23 (m, 2H), 1.90-1.86 (m, 2H), 1.77-1.64 (m, 2H), 1.60-1.43 (m, 8H), 1.34-1.27 (m, 2H) |
| $^{13}$C NMR (DMSO; 150 MHz) | 174.9, 174.1, 173.7, 172.0, 171.9, 170.4, 169.8, 162.6, 161.7, 160.3, 157.2, 156.7, 156.0, 148.6, 128.9, 128.7, 83.0, 82.2, 62.2, 55.4, 52.6, 52.5, 52.2, 52.0, 49.5, 40.9, 39.2, 39.1, 31.0, 30.7, 29.8, 29.5, 28.3, 27.1, 27.0, 25.4, 25.3, 22.9 |
| HRMS | Calculated mass $C_{43}H_{71}N_{24}O_{11}$ [M + H]$^+$ 1099.5729; found 1099.5727 |
| Elemental analysis | Calculated for $(C_{43}H_{70}N_{24}O_{11})(TFA)_5(H_2O)_3(H_2SO_4)_{1.5}(Et_2O)$ = C (35.22), H (4.82), N (17.30), S (2.47); found: C (35.20), H (4.71), N (17.25), S (2.49) |

TABLE 2

$^1$H NMR, $^{13}$C NMR, HRMS and elemental analysis data of TBL and intermediates
TBL and Intermediate Characterization Data

| | |
|---|---|
| Monomer 3 | R$_f$ = 0.25 (10% MeOH in EtOAc); $^1$H NMR (CDCl$_3$, 500 MHz) (ppm) 7.44-7.32 (m, 5H), 5.56 (s, 2H), 4.75 (bs, 1H), 4.50 (t, 2H, J = 6.3 Hz), 3.46 (s, 3H), 3.07 (app. t, 4H, J = 6.0 Hz), 2.73 (t, 2H, J = 6.9 Hz), 1.58 (s, 9H), 1.54-1.44 (m, 4H), 1.42 (s, 9H), 1.33 (s, 18H); $^{13}$C NMR (CDCl$_3$, 125 MHz) (ppm) 165.8, 161.2, 160.9, 160.5, 156.0, 155.9, 152.6, 149.3, 134.9, 128.6, 128.5, 128.3, 93.1, 83.8, 83.3, 70.1, 50.0, 47.0, 42.6, 40.2, 34.9, 28.4, 28.1, 27.8, 27.6, 26.3; HRMS calculated for $C_{40}H_{61}N_8O_{10}$ [M]$^+$ 813.4505, found 813.4507. |

TABLE 2-continued $^1$H NMR, $^{13}$C NMR, HRMS and elemental analysis data of TBL and intermediates
TBL and Intermediate Characterization Data

| | |
|---|---|
| Dimer 4 | $R_f$ = 0.26 (50% EtOAc in hexanes); $^1$H NMR (CDCl$_3$, 500 MHz) (ppm) 7.46-7.33 (m, 10H), 5.57 (s, 4H), 4.87 (bs, 1H), 4.39 (t, 4H, J = 7.2 Hz), 3.48 (s, 6H), 3.06 (m, 2H), 2.90 (t, 4H, J = 7.3 Hz), 2.67 (m, 2H), 1.56 (s, 18H), 1.41 (s, 14H), 1.31 (s, 36H); $^{13}$C NMR (CDCl$_3$, 125 MHz) (ppm) 165.7, 161.2, 161.1, 160.3, 156.1. 155.6, 152.6, 149.3, 135.0, 128.6, 128.5, 127.8, 114.0, 92.9, 83.7, 82.9, 78.8, 70.1, 53.9, 50.9, 41.3, 40.5, 35.0, 29.7, 28.5, 28.1, 27.9, 25.1; HRMS calculated for C$_{71}$H$_{100}$N$_{14}$O$_{18}$Na [M + Na]$^+$ 1459.72377, found 1459.72376. |
| TBL | mp = 296-301° C. (Decomposition); $^1$H NMR (DMSO, 600 MHz) (ppm) 12.32 (s, 2H), 9.15 (s, 2H), 8.90 (s, 2H), 8.57 (app. q, 2 H, J = 4.8 Hz), 8.11 (bs, 3H), 4.45 (bs, 2H), 3.46 (bs, 3H), 3.30 (bs, 4H), 2.95 (d, 6H, J = 4.7 Hz), 2.81-2.75 (m, 2H), 1.85-1.75 (m, 2H), 1.70-1.58 (m, 2H); $^{13}$C NMR (DMSO, 100 MHz) (ppm) 160.3, 159.6, 155.9, 155.6, 147.6, 82.4, 51.2, 48.3, 37.8, 36.0, 27.7, 23.8, 19.7; HRMS calculated for C$_{22}$H$_{33}$N$_{14}$O$_4$ [M + H]$^+$ 557.2804, found 557.2803; Elemental analysis calculated for C$_{22}$H$_{32}$N$_{14}$O$_4$(HCl)$_4$(H$_2$O)$_{1.5}$ C, 36.22, H, 5.39, N, 26.88, found C, 36.31, H, 5.35, N, 26.44. |

Transmission electron microscopy (TEM) imaging was used to characterize the various single and twin base RNT morphologies. As previously described [see Zhang et al., *J. Org. Chem.* 1972; 37(22):3404-3409 hereby incorporated by reference herein], carbon-coated 400-mesh copper grids (EM Sciences, PA) were floated on a dH$_2$O droplet of each RNT (0.1 mg/mL or 0.01 mg/mL) for 2 min to adsorb the RNTs. The grids were then placed onto a droplet of dH$_2$O for 20 s to remove excess non-adherent RNTs before they were placed on a second droplet of 2% aqueous uranyl acetate for 20 s to negatively stain the RNTs. The grids were then dried with filter paper and imaged on a Philips EM410 under an acceleration voltage of 120 kV. The KRSR peptide (not coupled to C∧G base) was also imaged as a control experiment.

Figures 2, 2A, 3:
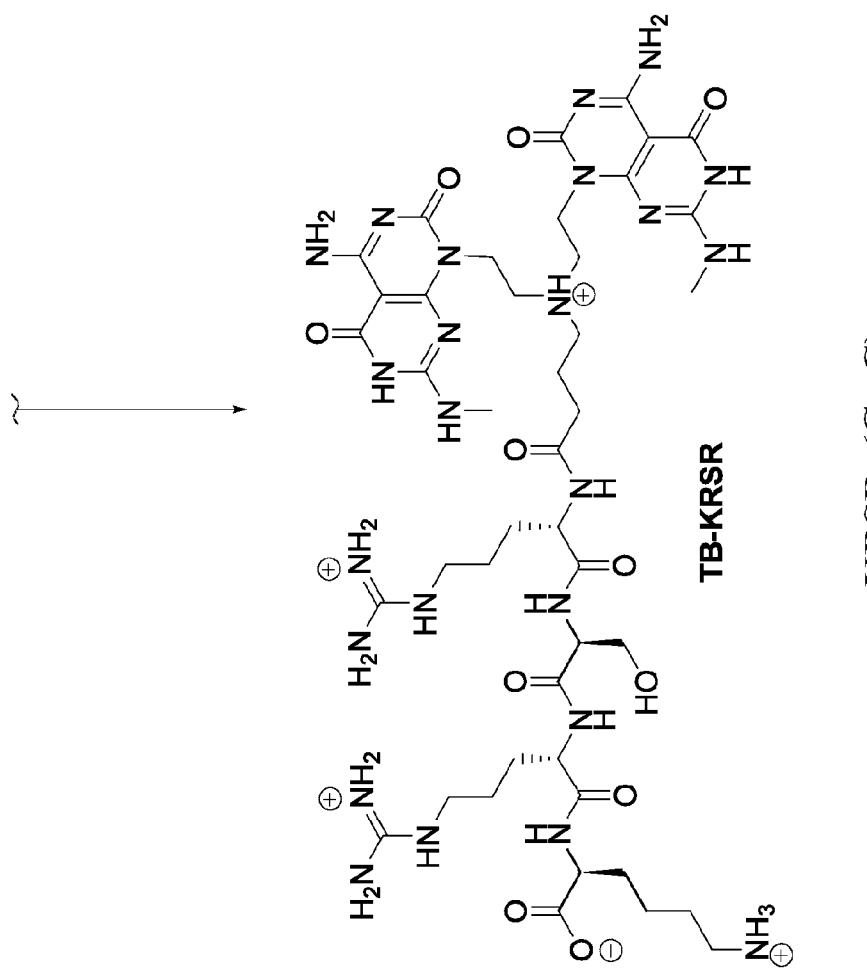
FIG. 3. TEM images of the various RNTs: (A) and (B) 0.1 mg/mL and 0.01 mg/mL TB-KRSR RNTs; (C) and (D) 0.1 mg/mL TBL RNTs (HCl and TFA, respectively); (E) 0.1 mg/mL MB-K RNTs; (F) 0.1 mg/mL 5% MB-RGD-K RNTs; and (G) 0.1 mg/mL KRSR peptide only without nanotubes. Arrows show the nanotubes.
Figure 2B:
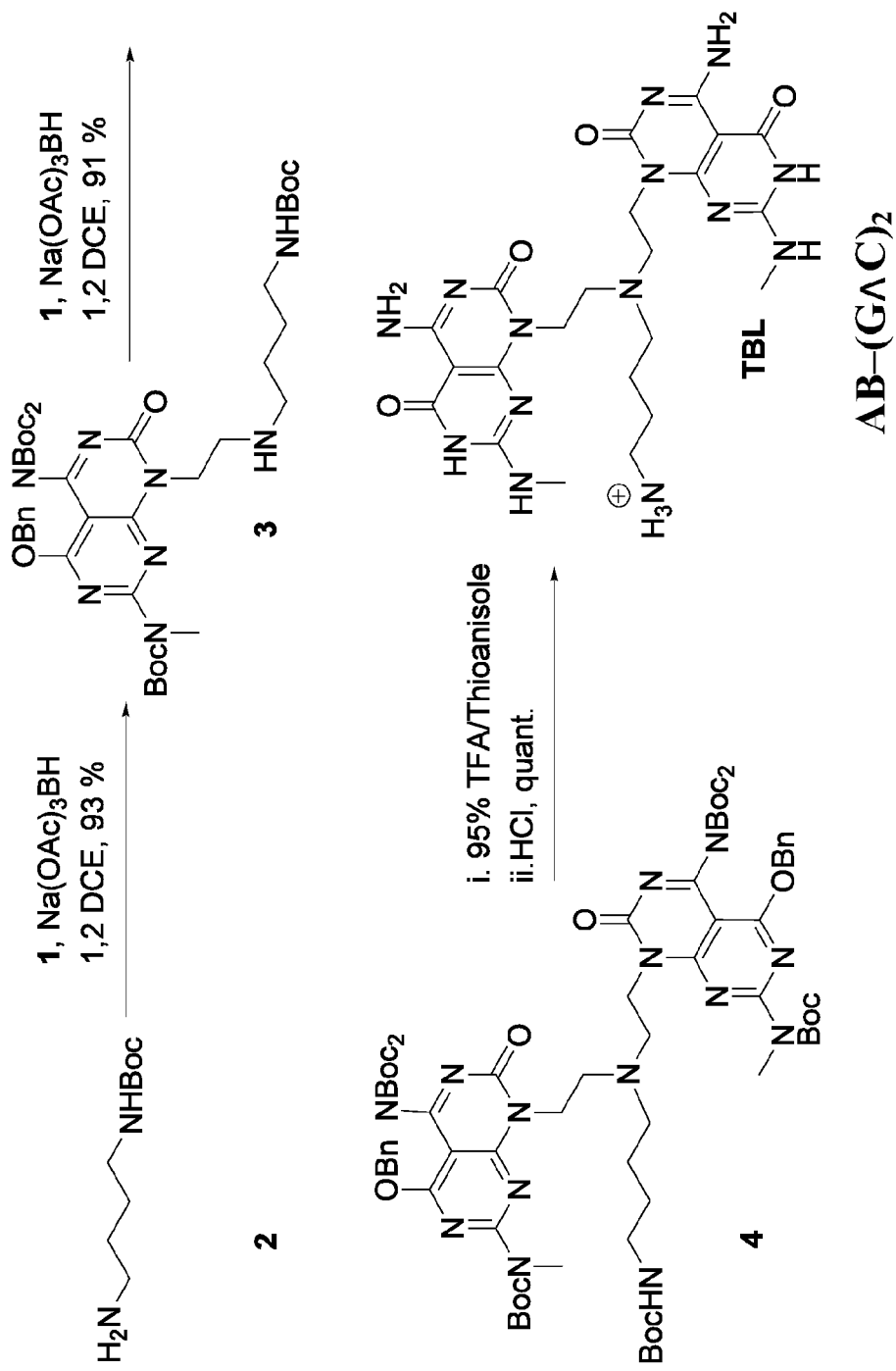
Figure 3:
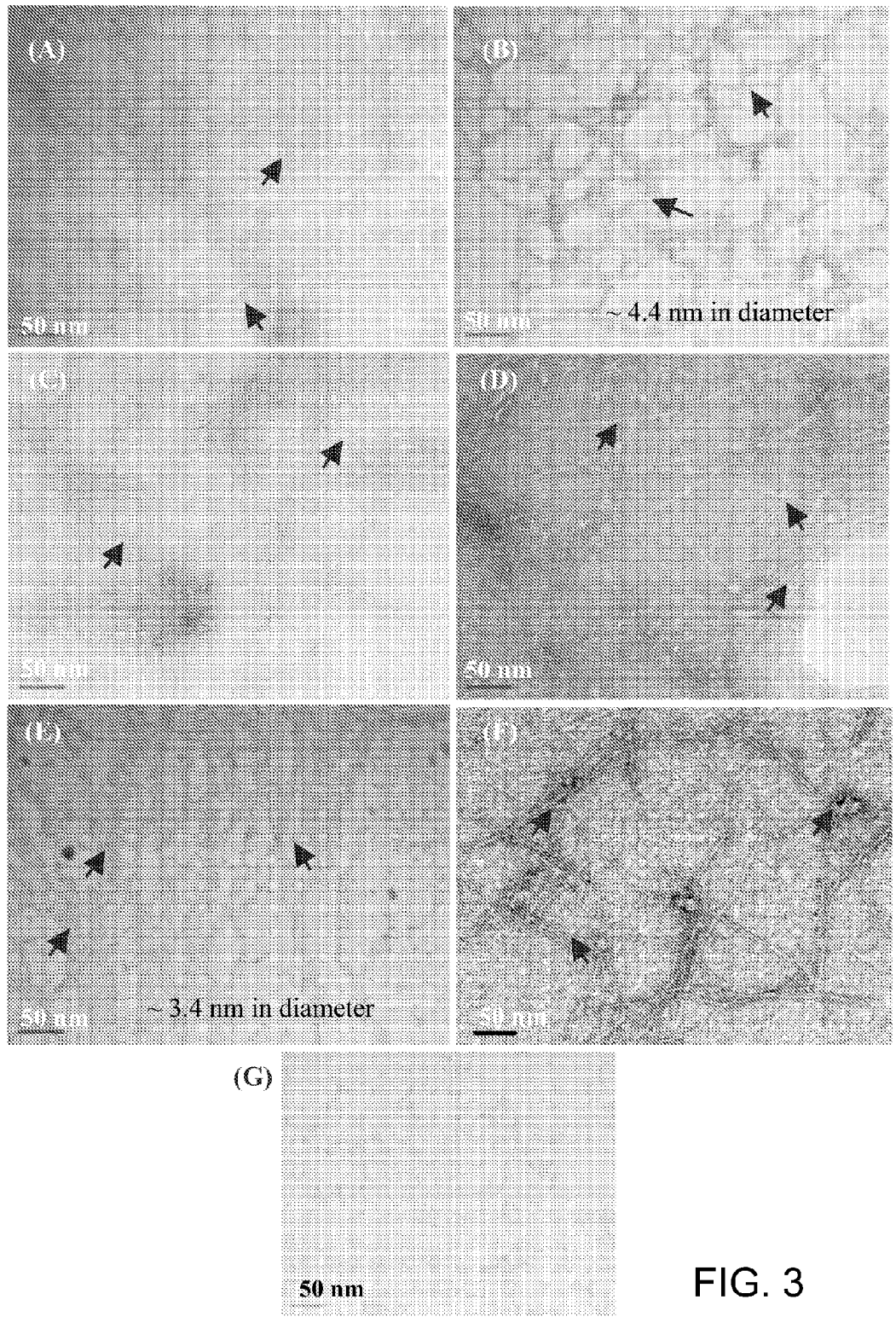

Irrespective of the side chains on the C∧G motif, all the resulting RNTs showed nanostructures of high aspect ratio (FIG. 3). TEM images revealed a larger diameter (4.4±0.2 nm) for KRSR-RNT$^r$ (FIGS. 3A-B) as compared to AB-RNT$^r$ (3.5±0.2 nm) (FIG. 3C-D) due to the bulkier KRSR moiety attached on the periphery of the twin base. K-RNT$^m$ and K$^{95}$/RGD$^5$-RNT$^m$ (FIG. 3E-F) featured a diameter of 3.4±0.3 nm. As expected the control sample with KRSR peptide did not show any 1D morphologies (FIG. 3G).

For scanning electron microscopy (SEM) imaging, twin bases (0.5 mg/mL) were dissolved in dH$_2$O by sonication at room temperature for ~2 min, The solutions were filtered on 0.25 µm Whatmann filter membrane, heated to boiling (to promote self-assembly), and aged for 1 day. The solutions were diluted to 0.025 mg/mL with dH$_2$O prior to imaging. SEM samples were prepared by floating a carbon-coated 400-mesh copper grid on a droplet of the diluted RNT solution for 10 s. The grid was blotted and floated onto a drop of 2% uranyl acetate for 10 s. The RNT-coated grid was then air-dried and heated on a hot-plate (100° C.) for 15 min before imaging on a high resolution Hitachi S-4800 SEM.

For atomic force microscopy (AFM) imaging, one drop of the diluted RNT solution (0.05 mg/mL) was deposited onto a freshly cleaved mica substrate (1 cm$^2$) for 10 s and excess solution was blotted using filter paper. The sample surface was imaged using a Digital Instruments/Veeco Instruments MultiMode Nanoscope IV AFM equipped with an E scanner in tapping mode. Silicon cantilevers (MikroMasch USA, Inc.) with low spring constants of 4.5 N/m, a scan rate of 0.5-1 Hz and amplitude setpoint of 1 V were used.

Figure 4:
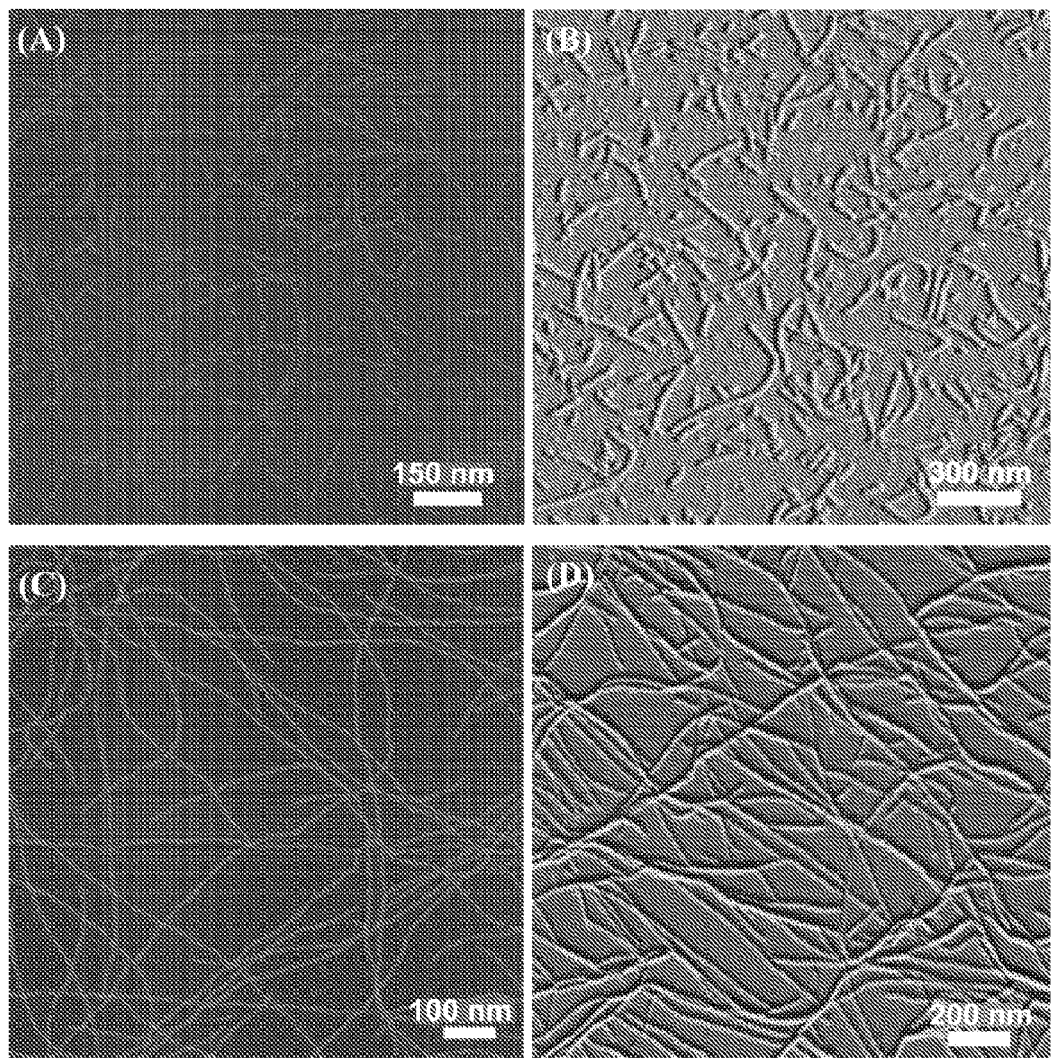
FIG. 4. SEM and AFM images of (A) and (B) TB-KRSR RNTs; and (C) and (D) TBL RNTs.

SEM and AFM images revealed dense nanotubular networks for both KRSR-RNT$^r$ and AB-RNT$^r$ (FIG. 4). The average length of KRSR-RNT$^r$ was less than that of AB-RNT$^r$, suggesting that the peptide bulkiness influences the degree of stacking and hence the length of the RNTs.

Example 4

Preparation of RNT Coatings on Titanium Substrates

Titanium (Ti) (1 cm×1 cm×0.05 cm) (Alfa Aesar Ti foil) and glass coverslips were soaked in acetone for 15 min, sonicated for 15 min in acetone, and rinsed with dH$_2$O. They were then soaked and sonicated in 70% ethanol and rinsed with dH$_2$O. Lastly, they were soaked and sonicated in dH$_2$O for another 15 min and rinsed. The glass was then etched in 1 M NaOH for 1 h and thoroughly rinsed in dH$_2$O. All of the Ti and glass coverslips were oven-dried overnight and autoclaved for sterilization. The day before cell seeding, the cleaned Ti substrates were coated with the various RNTs (0.01 mg/mL) and KRSR peptide (0.01 mg/mL) solutions for 45 min at room temperature. They were then removed from the solutions and air-dried overnight.

Example 5

Osteoblast, Fibroblast and Endothelial Cell Culture

A human fetal osteoblast cell line (ATCC, CRL-11372, VA) was cultured in Dulbecco's modified eagle's medium (DMEM, Invitrogen Corporation) supplemented with 10% fetal bovine serum (FBS, Hyclone, UT) and 1% penicillin/streptomycin (P/S, Hyclone, UT) under standard cell culture conditions (37° C., humidified, 5% CO$_2$ in air). Cells were used up to population numbers of 8-11 in the experiments without further characterization.

A rat skin fibroblast cell line (FR, ATCC, CRL-1213) was cultured in Eagle's Minimum Essential Medium (EMEM, ATCC 30-2003) supplemented with 10% FBS under standard cell culture conditions. Rat aortic endothelial cells (RAEC, VEC Technologies) were cultured in MCDB-131 complete medium (VEC Technologies) under standard cell culture conditions. The fibroblasts were used at population numbers 6-9 and the endothelial cells were used at population numbers 6-11 during culture. The cell medium was replaced every other day.

Example 6

Osteoblast, Fibroblast and Endothelial Cell Adhesion

Osteoblasts, fibroblasts and endothelial cells were seeded onto the substrates at a density of 3500 cells/cm$^2$ and were incubated in the cell culture medium (specifically, DMEM supplemented with FBS and P/S for osteoblasts, EMEM supplemented with FBS for fibroblasts and MCDB-131 complete medium for endothelial cells) for 4 h. Then, the substrates were rinsed three times with a phosphate buffered saline (PBS) to remove non-adherent cells. The remaining cells were fixed using 10% normal buffered formaldehyde (Fisher Scientific) for 10 min and 0.1% Triton X-100 (Sigma-Aldrich, MO) for 5 min. Cells were then stained with rhodamine-phalloidin (staining F-actin filaments, Molecular Probes) to examine cell spreading and were further stained with DAPI (Invitrogen). The cells were observed using a fluorescent microscope (Axiovert 200M, Zeiss) and five different areas of each sample were imaged. The cell density was then determined by counting cells using Image Pro Analyzer. All cellular experiments were run in triplicate and repeated three times for each substrate.

Data are presented as the mean value±the standard error of the mean and were analyzed with a student's t-test to make pair-wise comparisons. Statistical significance was considered at p<0.1.

Example 7

Osteoblast Adhesion Greater on Coated Substrate than on Uncoated Substrate

Figure 5:
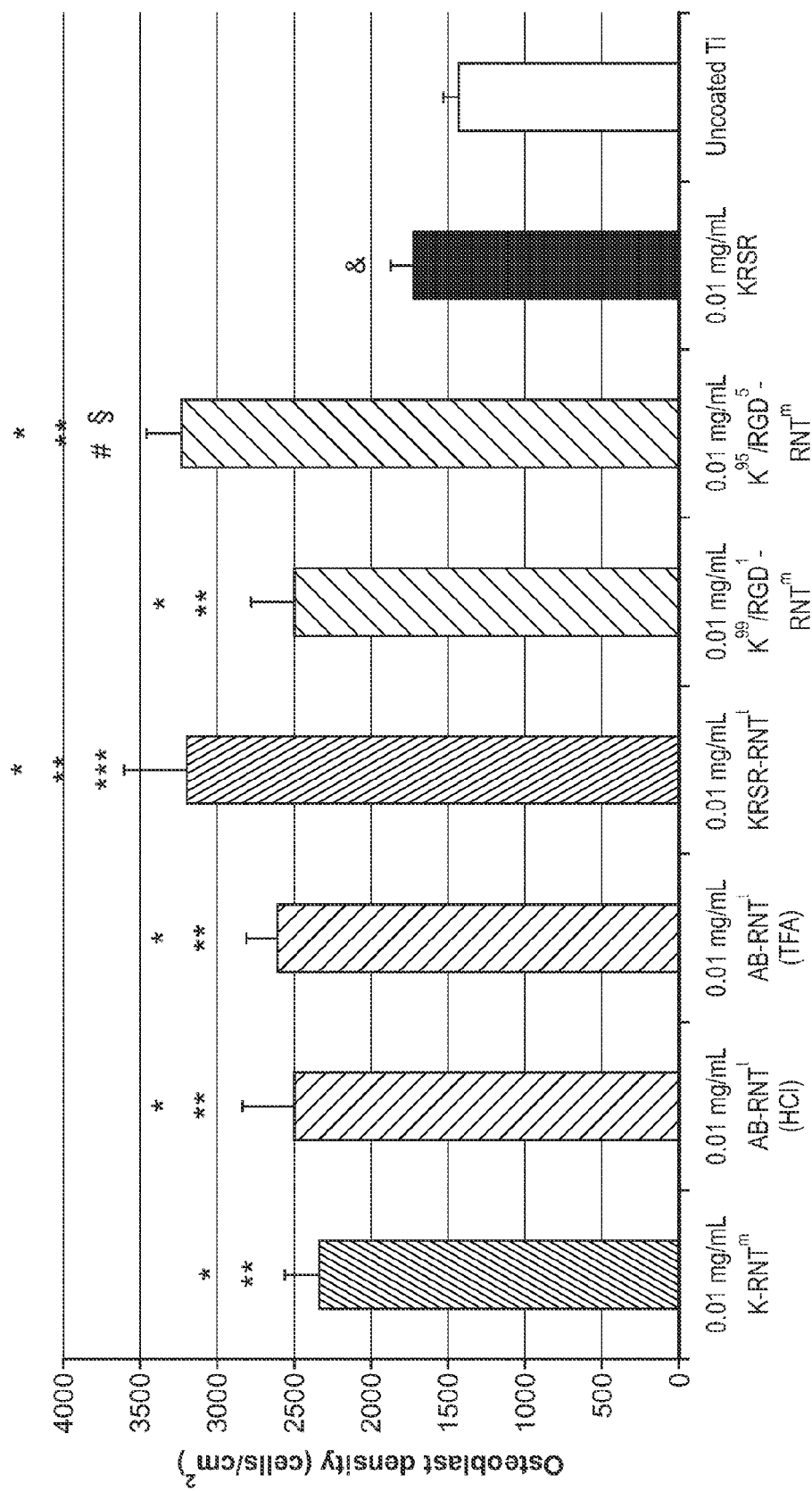
FIG. 5. Osteoblast adhesion on RNTs coated on titanium. Data are mean values±SEM, N=3. *$p<0.01$ and &$p<0.1$ compared to uncoated titanium; $p<0.05$ compared to 0.01 mg/mL KRSR coated on titanium; *$p<0.1$ compared to 0.01 mg/mL MB-K, 1% MB-RGD-K, TBL RNTs (HCl) coated on titanium; #$p<0.05$ compared to 0.01 mg/mL MB-K RNTs coated on titanium; and §$p<0.1$ compared to 1% MB-RGD-K, TBL (in HCl or in TFA) RNTs coated on titanium.

All of the RNTs coated on Ti significantly enhanced osteoblast adhesion compared to uncoated Ti after 4 h (p<0.01) (FIG. 5). The nanotube KRSR-RNT$^t$ greatly improved osteoblast adhesion relative to K-RNT$^m$, AB-RNT$^t$, and uncoated Ti. Compared to uncoated Ti, the 0.01 mg/mL KRSR-RNT$^t$ and K$^{95}$/RGD$^5$-RNT$^m$ coated Ti improved osteoblast adhesion by 122% and 124% respectively. In fact, KRSR-RNT$^t$ and K$^{95}$/RGD$^5$-RNT$^m$ promoted the greatest osteoblast densities on Ti. In addition, the KRSR peptide alone on Ti promoted more osteoblast cell adhesion relative to uncoated Ti. There was no statistically significant difference among AB-RNT$^t$, K$^{99}$/RGD$^1$-RNT$^m$, and K-RNT$^m$.

Figure 6:
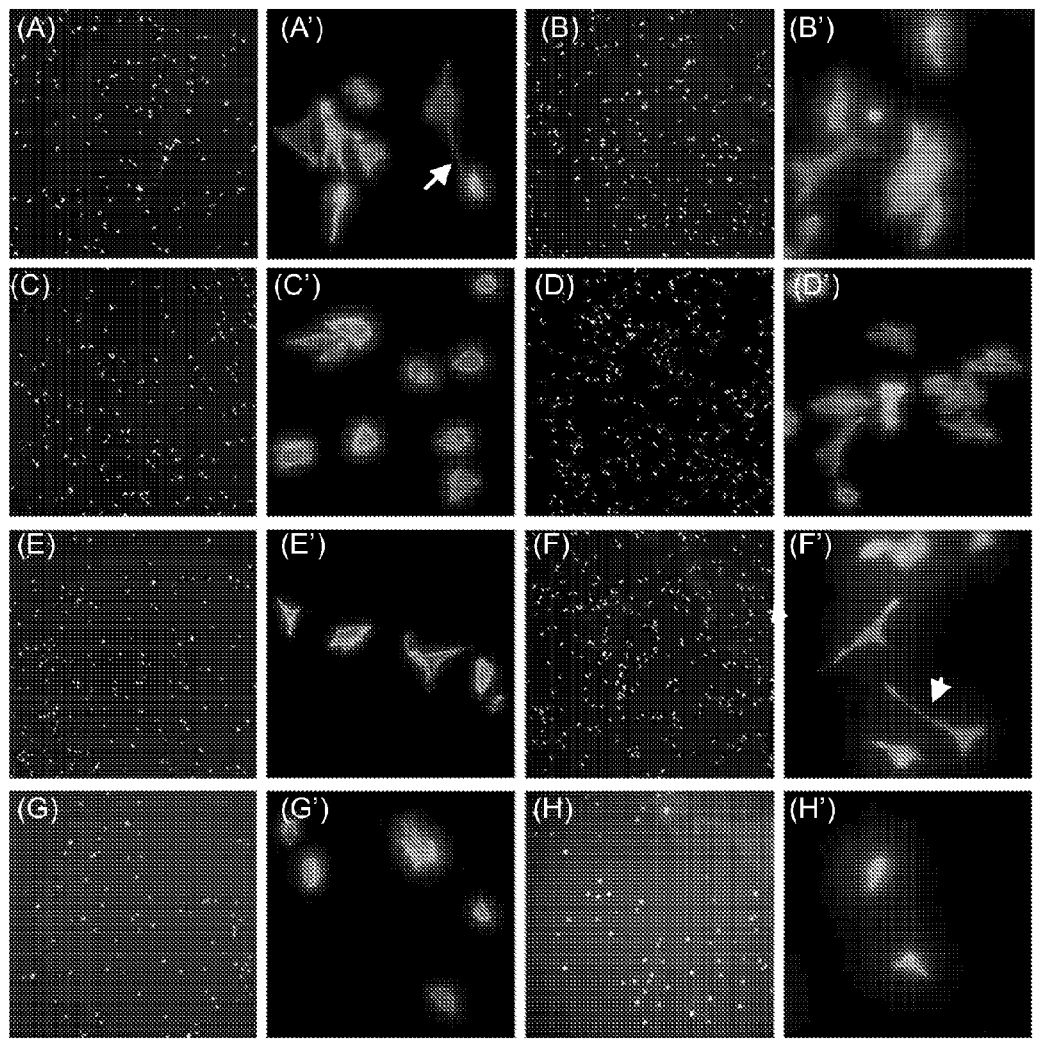
FIG. 6. Fluorescent microscopy images of osteoblast adhesion on RNT coated on titanium at low (original magnification 50×, DAPI stained nuclei) and high magnifications (400×, rhodamine-phalloidin stained F-actin filaments). 0.01 mg/mL of (A) and (A') MB-K RNTs; (B) and (B') TBL RNTs (HCl); (C) and (C') TBL RNTs (TFA); (D) and (D') TB-KRSR RNTs; (E) and (E') 1% MB-RGD-K RNTs; (F) and (F') 5% MB-RGD-K RNTs; and (G) and (G') KRSR coated titanium; and (H) and (H') uncoated titanium. Arrows point to long filopodia.

In addition, more osteoblasts adhered to Ti when the latter was coated with KRSR-RNT$^t$ versus KRSR. Specifically, osteoblast adhesion on Ti coated with KRSR-RNT$^t$ was 84.4% higher than Ti coated with the peptide KRSR alone. Additionally, osteoblasts were better spread with more extended filopodia on RNT-coated Ti than on uncoated Ti (FIG. 6).

Example 8

Coated Substrates Did not Increase Fibroblast Adhesion

Figure 7:
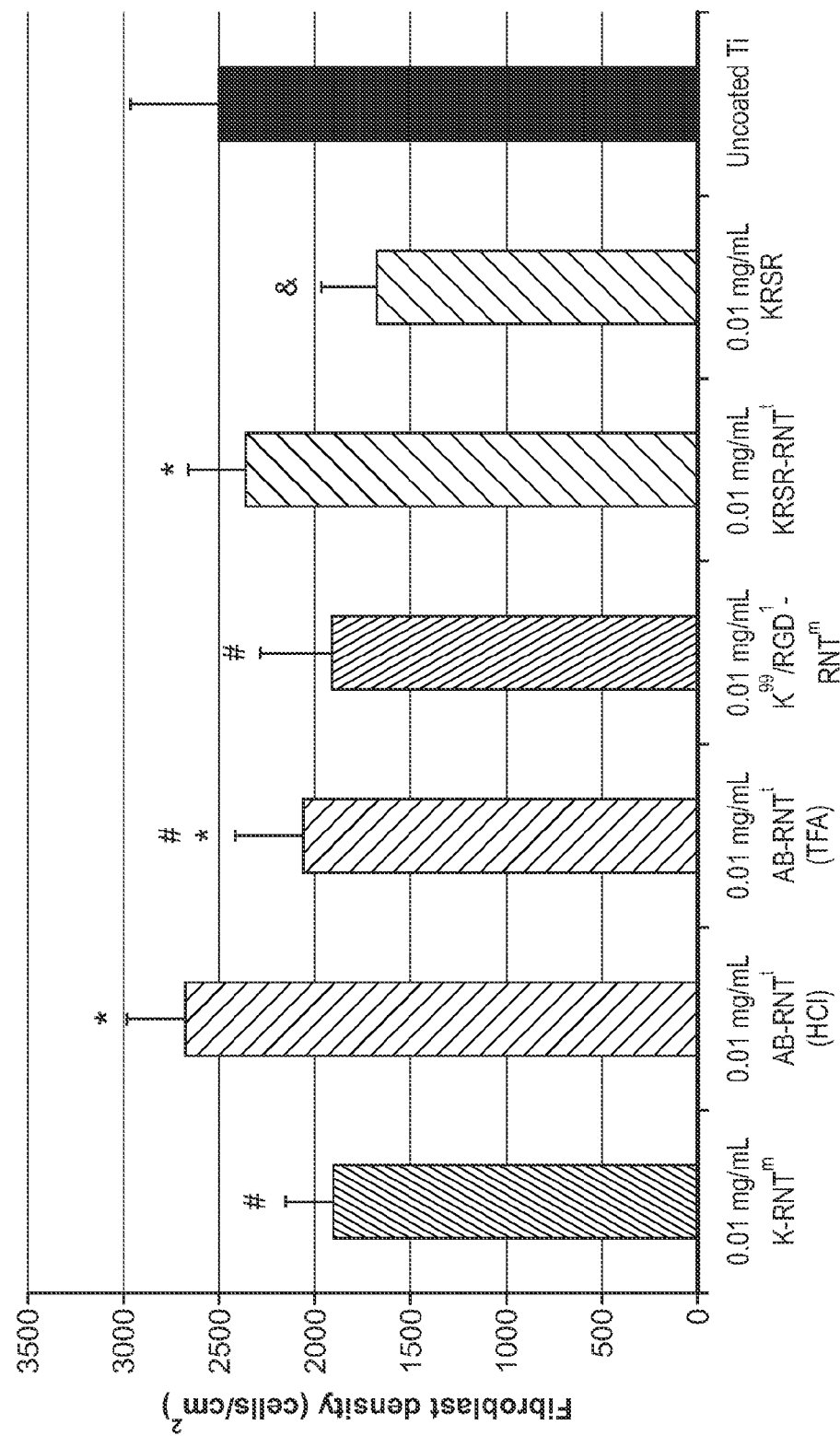
FIG. 7. Fibroblast adhesion on RNTs coated on titanium. Data are mean values±SEM, N=3. *$p<0.05$ compared to 0.01 mg/mL KRSR coated on titanium; #$p<0.05$ compared to 0.01 mg/mL TBL RNTs (HCl) coated on titanium; and &$p<0.05$ compared to uncoated titanium.
Figure 8:
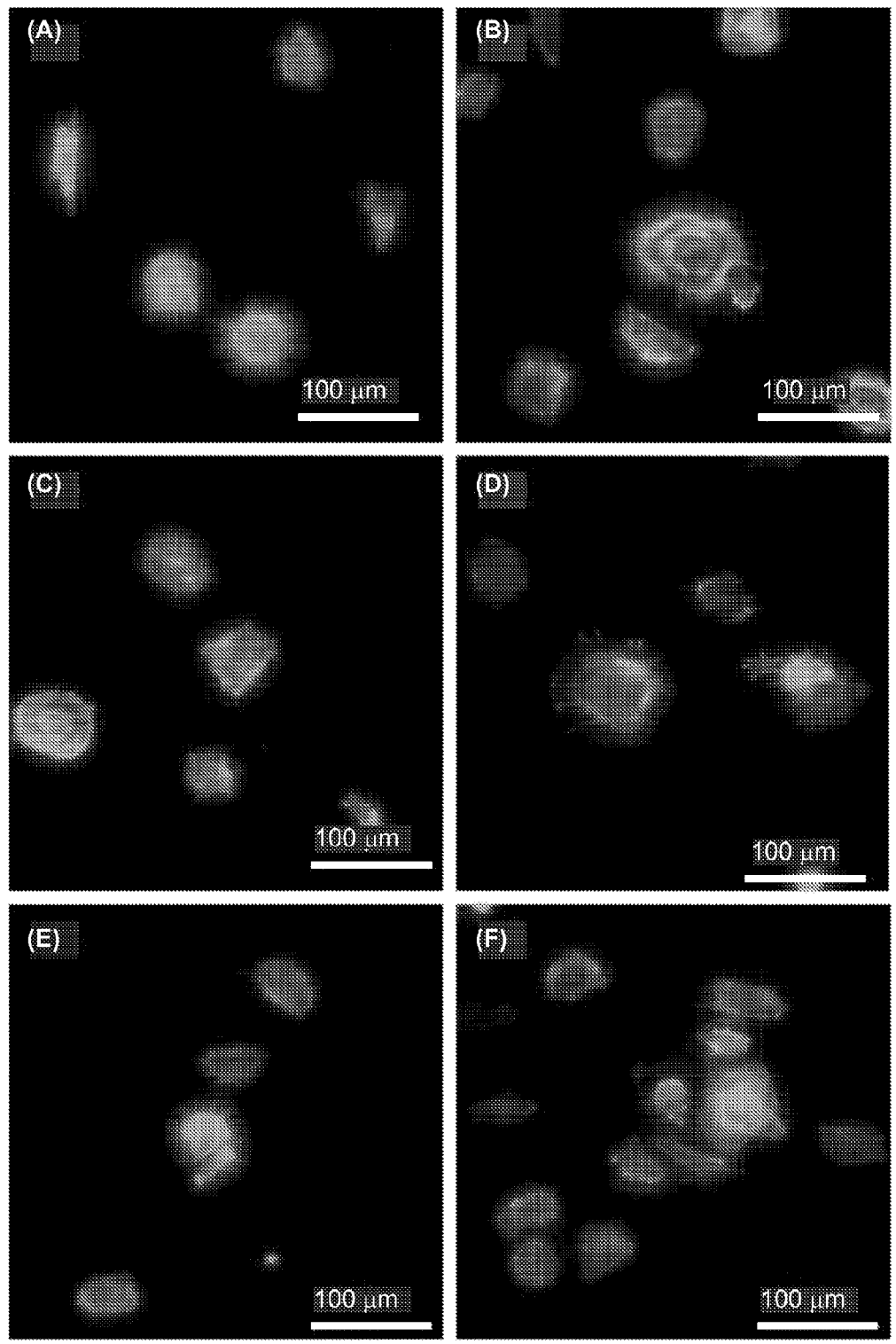
FIG. 8. Fluorescent microscopy images of fibroblast spreading. (A) MB-K RNTs coated on titanium; (B) TBL RNTs (HCl) coated on titanium; (C) 1% MB-RGD-K RNTs coated on titanium; (D) TB-KRSR RNTs coated on titanium; (E) KRSR coated on titanium; and (F) uncoated titanium. F-actin filaments were stained by rhodamine-phalloidin.

Compared to uncoated Ti, KRSR-RNT$^t$, K$^{99}$/RGD$^1$-RNT$^m$, K-RNT$^m$, and AB-RNT$^t$ did not alter fibroblast adhesion after 4 h (FIG. 7). AB-RNT$^t$ was assembled from the HCl and TFA salts of AB-(C∧G)$_2$. The differences in fibroblast attachment with these two types of RNTs may be associated with their different counter ions. In contrast with its effect on osteoblast adhesion, the KRSR peptide did not enhance fibroblast adhesion on Ti. In accordance with one aspect of the present invention, a nanotube incorporating KRSR provides for cell selectivity and utility in orthopedic applications. Finally, many small filopodia extensions from rounded fibroblasts were visible on all substrates, indicating that fibroblasts spread regardless of the Ti coatings (FIG. 8).

Example 9

Certain RNTs Increase Endothelial Cell Adhesion

Figure 9:
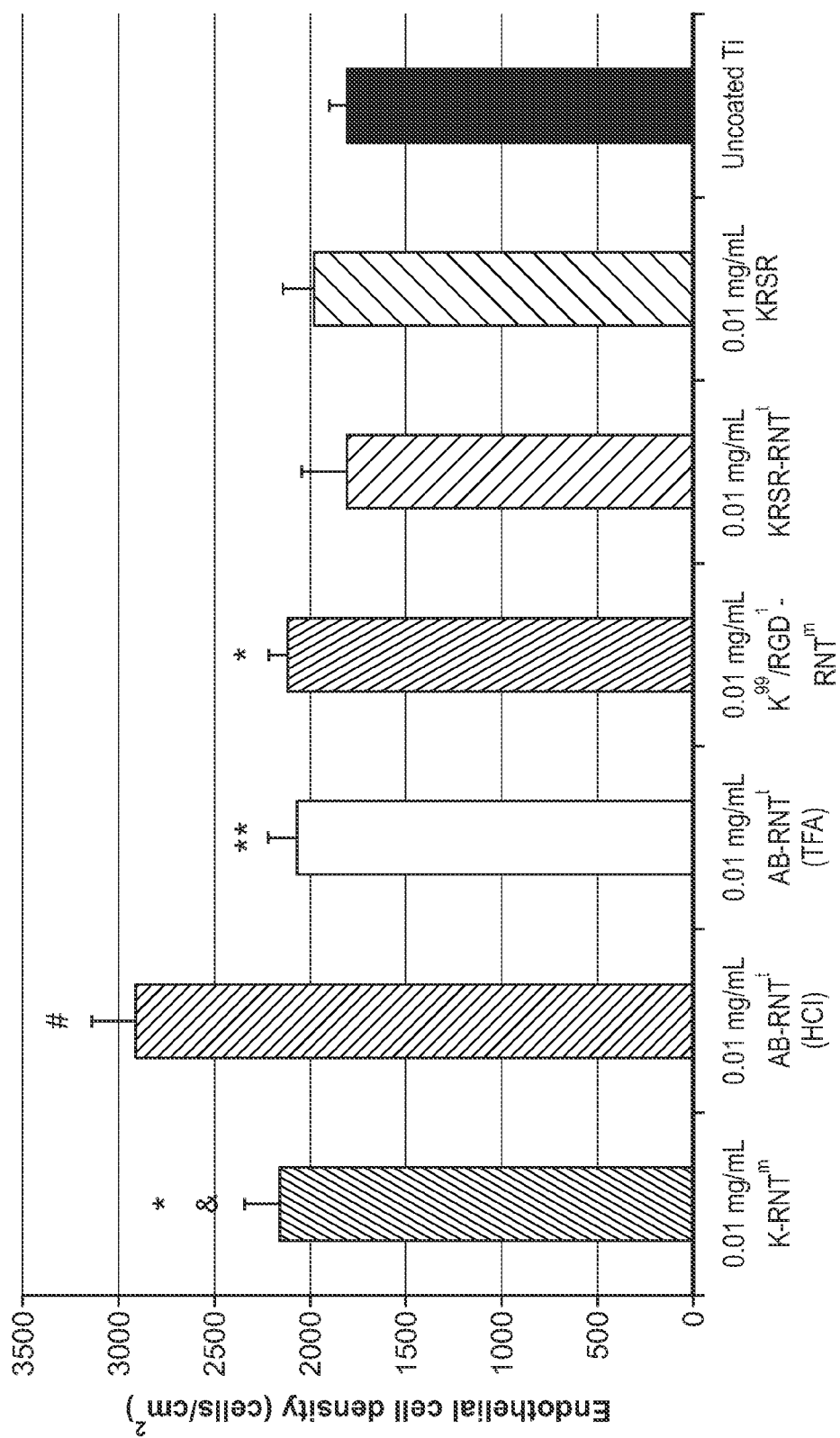
FIG. 9. Endothelial cell adhesion on RNTs coated on titanium. Data are mean values±SEM, N=3. *$p<0.05$ and **$p<0.1$ compared to uncoated titanium. #$p<0.05$ compared to all other substrates. &$p<0.1$ compared to 0.01 mg/mL TB-KRSR RNTs coated on titanium.
Figure 10:
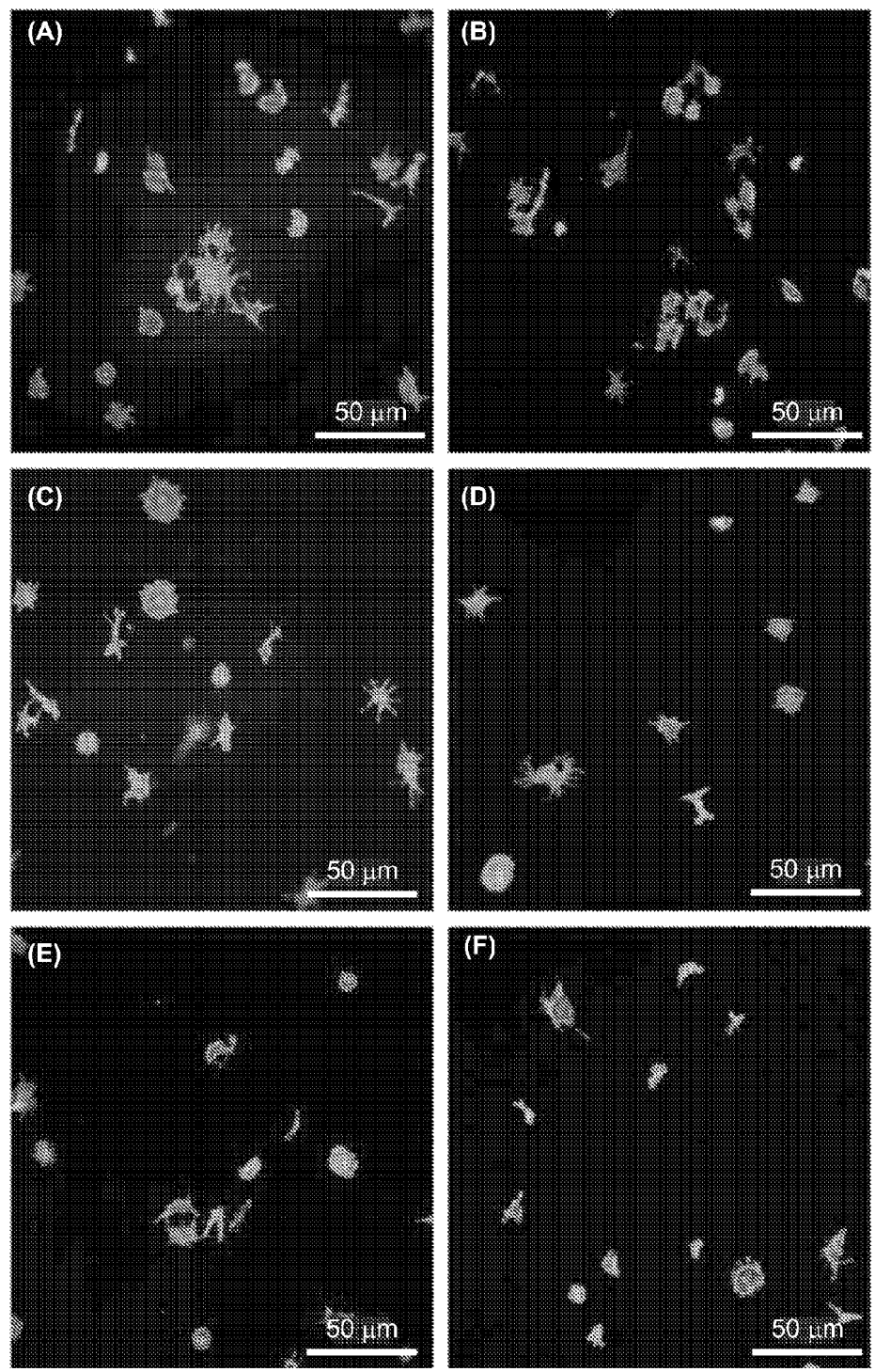
FIG. 10. Fluorescent microscopy images of endothelial cell spreading on various coatings after 4 h. (A) MB-K RNTs coated on titanium; (B) TBL RNTs (HCl) coated on titanium; (C) 1% MB-RGD-K RNTs coated on titanium; (D) TB-KRSR RNTs coated on titanium; (E) KRSR coated on titanium; and (F) uncoated titanium. F-actin filaments were stained by rhodamine-phalloidin (green color) and cell nuclei were stained by DAPI (blue color).

As shown in FIG. 9, a significantly higher endothelial density on the Ti coated with RNTs (except for KRSR-RNT$^t$) was achieved as compared to uncoated Ti after 4 h. In addition, AB-RNT$^t$ (HCl) coated Ti promoted the greatest endothelial cell adhesion compared to all other substrates. Furthermore, more endothelial cells attached on Ti coated with K-RNT$^m$ and AB-RNT$^t$ (HCl) than on Ti coated with KRSR-RNT$^t$. KRSR-RNT$^t$ and KRSR peptide coated Ti did not enhance endothelial cell adhesion. According to one aspect of the present invention, the nanotubes incorporating KRSR selectively promote osteoblast adhesion. Endothelial cell spreading morphologies were shown in FIG. 10. FIG. 10 shows excellent cytocompatibility properties of K-RNT$^m$ and RGD-RNT$^m$ for endothelial cell adhesion and the selectivity of KRSR-RNT$^t$ only for osteoblast adhesion. Accordingly, a thin film of nanostructured RNT coatings with numerous K or RGD side chains alters the surface chemistry and surface roughness of conventional Ti to provide a favorable environment for enhancing endothelial cell adhesion. According to one aspect of the present invention, a nanotube is formed including K or RDG side chains that promote adhesion of endothelial cells and the growth of new blood vessels in bone formed around an orthopedic implant. The nanotube may also include KRSR side chains that promote the adhesion of osteoblasts. A nanotube with a combination of K, RDG and KRSR side chains promotes the selective adhesion of osteoblasts and endothelial cells leading to the formation of new bone tissue useful in orthopedic applications.

Example 10

Synthesis of Hydroxyapatite Nanoparticles

Hydroxyapatite (HA) nanoparticles were synthesized by stirring (NH$_4$)$_2$HPO$_4$ and Ca(NO$_3$)$_2$ in a NH$_4$OH solution (pH>10), following the equation below.

For a narrow size distribution, the reaction was carried at 4° C. First, 30 mL of 0.6 M ammonium phosphate solution was added into 300 ml basic water adjusted by NH$_4$OH (pH>10). Then 30 ml of 0.6 M calcium nitrate was added dropwise at 3 ml/min. Following stirring for 10 min, the precipitate was washed three times by centrifugation at 5000 rpm for 5 min. Then, the HA precipitates were treated hydrothermally in a Teflon liner at 200° C. for 20 h. After the hydrothermal step, the precipitate was washed with deionized water once and placed in an oven at 80° C. overnight.

Example 11

Synthesis of Composites Including Nanotubes

Composites of nanotubes, compounds for providing mechanical strength and/or surface roughness and a polymer matrix were prepared as follows. The polymerization process of the composites with varying HA nanoparticle concentrations (2%, 10%, 20%) was initiated by 2,2'-azobisisobutyronitrile (AIBN) via sonication or oven at 60° C. Specifically, the mixture of 5 ml HEMA, deionized water and HA nanoparticle powders was sonicated for 20 min, followed by the addition of 0.01 mg/ml TBL molecules of formula II where X is nitrogen, $R_1$ is methyl, $R_2$ is absent and Y is absent and 3 mg/ml of the AIBN initiator. Finally, the composites were heated in a sonicator or oven at 60° C. until samples solidified completely.

Polymerization times of TBL/HA/pHEMA composites (100% HEMA, 2% HA, 3 mg/ml AIBN, 0.01 mg/ml TBL molecules of formula II where X is nitrogen, $R_1$ is methyl, $R_2$ is absent and Y is absent) via four heating methods including the oven, water-bath, sonication, or microwave were compared. Then, the temperature profile of the samples (400 µl/tube) using sonication (60° C., strength 5) and microwave (700 W, 50 s, power 5) were tested using a digital thermometer.

As shown in Table 1, compared with the conventional oven and water bath, the sonication and microwave can reduce the solidification time from more than 40 minutes to several minutes due to the rapid heat-transfer process.

|  | Methods | | | |
| --- | --- | --- | --- | --- |
|  | Oven 60° C. | Water bath 60° C. | Sonication 60° C. | Microwave |
| Solidification time | >40 min | ~25-30 min | 8-12 min | <2 min |

Figure 11A:
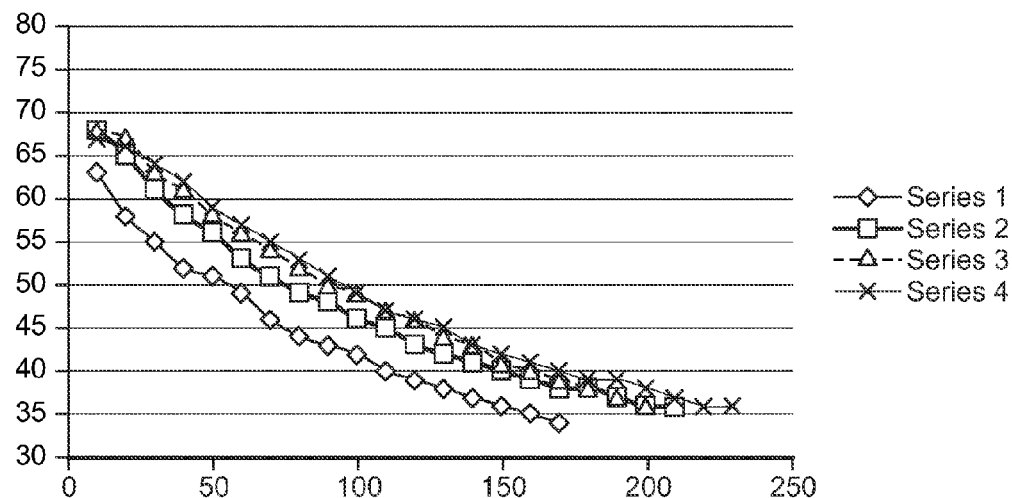
FIG. 11. Graph of temperature curves of TBL/HA/pHEMA composites after (a) sonication and (b) microwave.
Figure 11B:
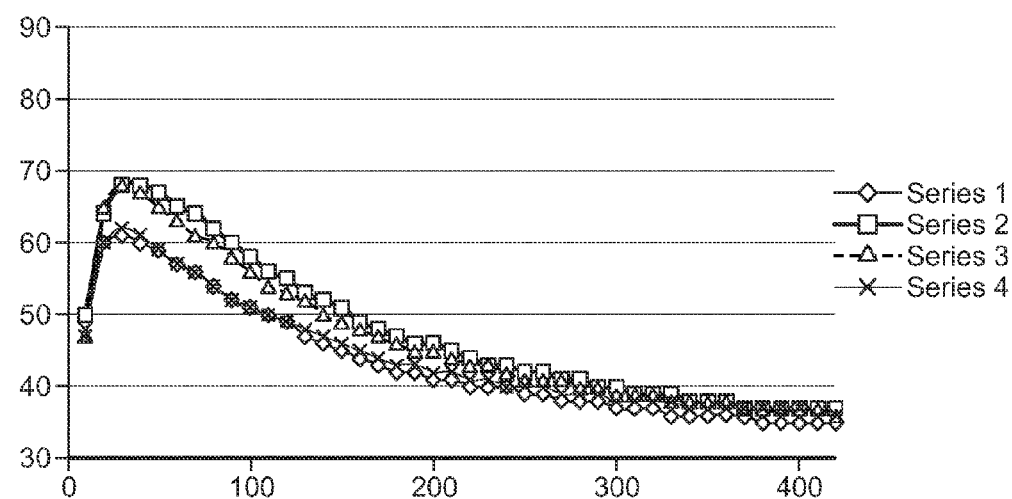

As shown in FIG. 11, the temperature profiles of samples via sonication (FIG. 11a) or microwave heating (FIG. 11b) are in the similar temperature range from 60 to 70° C. For the composites without water, the window time from initiation stage to solidification is very short (~1 min).

The solidification properties involving time and final forms were studied through varying one component (AIBN initiator or water concentration) in the composites. The samples (400 µl) were placed into the BD syringes and heated in a water-bath sonicator at 60° C. Then, the solidification time and injection forms were recorded.

Figure 12A:
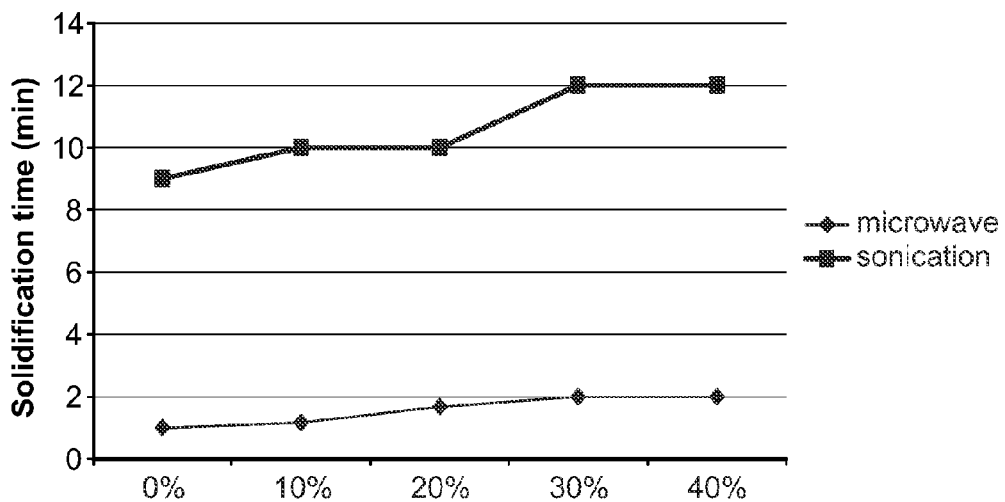
FIG. 12. Graph of solidification time of varying (a) water ratios and (b) AIBN initiator concentrations.
Figure 12B:
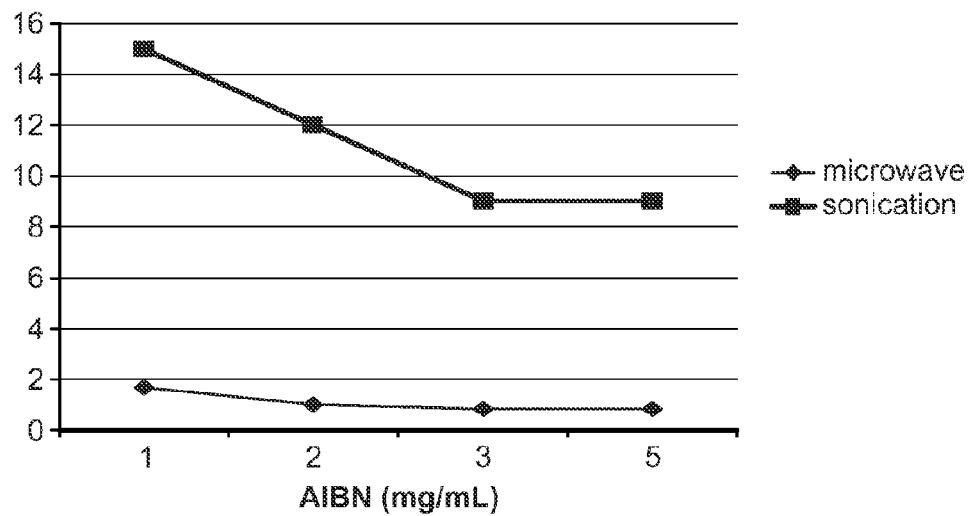

FIG. 12 shows the results of solidification time as a function of the amount of water (FIG. 12a) and AIBN initiator concentration (FIG. 12b). The solidification time was lengthened with increasing water content or decreasing AIBN initiator concentration. Moreover, combining low AIBN concentration with high water content resulted in reduced mechanical strength of the composites and increased window time.

Example 12

AFM Scanning

For AFM experiments, TBLs of Example 11 were diluted to 0.025 mg/mL in methanol. Clean mica substrates were prepared and the samples were deposited by spin-coating a 0.05-0.25 mg/ml solution on it at 2000 rpm for 20 s. Sample surfaces were observed using a Digital Instruments/Veeco Instruments MultiMode Nanoscope IV AFM equipped with an E scanner. For obtaining optimized height profiles in this investigation, silicon cantilevers (MikroMasch USA, Inc.) with low spring constants of 4.5 N/m were used in tapping mode (TM-AFM). To obtain a clear image from the surface, a low scan rate (0.5-1 Hz) and amplitude setpoint (1 V) were chosen during measurements (Moralez et al 2005).

Figure 13:
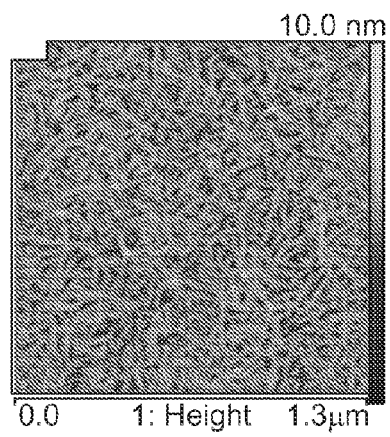
FIG. 13. AFM image of nanotubes formed from twin base linkers.

FIG. 13 is an atomic force microscopic image of nanotubes formed from twin base linkers of Example 11.

Example 13

SEM Imaging

The sample surfaces (100% HEMA, 3 mg/ml AIBN, 0.01 mg/ml TBLs of Example 11, HA (2%, 10%, 20%)) were first coated with a layer of gold. Then, the surface characterization and pore sizes of composites were studied by SEM (LEO 1530-VP) at a scale of 200 nm and 100 µm.

Figure 14:
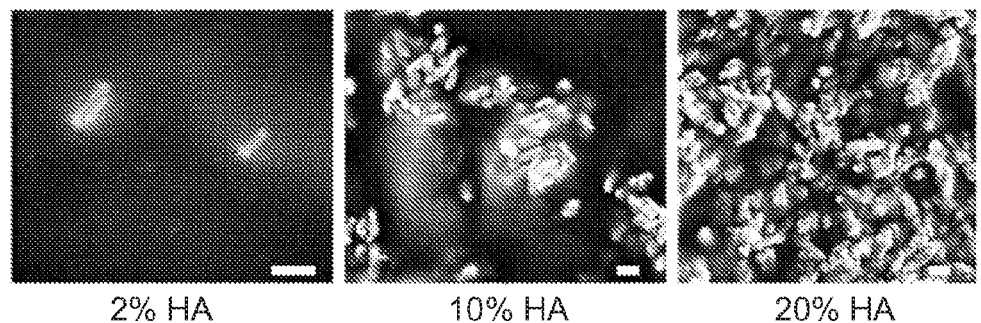
FIG. 14. SEM images of various composites of nanotubes formed from twin base linkers, hydroxyapatite and poly hydroxyethylmethacrylate. Scale bars=200 nm.

As shown in FIG. 14, with increasing HA ratios in the composites, more HA nanoparticles clustered on the surface, therefore generating greater nano-roughness. Since the surface topography is related with protein and cellular adhesion, cell movement, orientation, morphology, and even gene expression, the nanoroughness provided by the HA nanoparticles promotes the osteointegration between the bone and implants.

Figure 15:
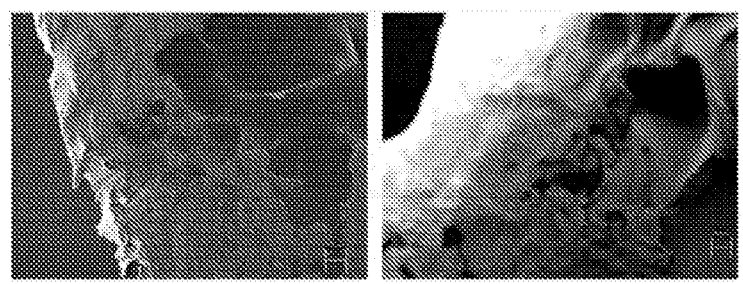
FIG. 15. SEM images of pores of composites of nanotubes formed from twin base linkers, hydroxyapatite and poly hydroxyethylmethacrylate. Scale bars=100

As shown in FIG. 15, the composites exhibit porosity which promote the growth of tissue into and through the implanted composites. Pore sizes can be between about 1 angstrom and about 999 microns in diameter. Pore density can be between about 0.0001% and about 99.9999%.

Example 14

Mechanical Properties

Compressive and tensile properties were tested following the ASTM standards D695-10 Standard Test Method for Compressive Properties of Rigid Plastics and D638-10 Standard Test Method for Tensile Properties of Plastics each of which are incorporated herein by reference in their entireties. Solidified composite samples were prepared following the above method. The Instron 5882 mechanical testing system was used to test the compressive curve of cylinder samples (12.7 mm in diameter and 25.4 in height) at the speed of 1.3 mm/min.

Figure 16:
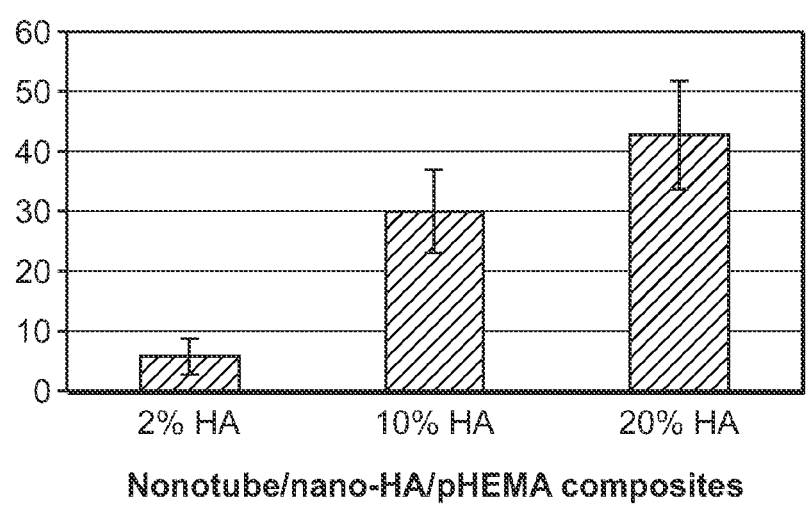
FIG. 16. Graph of compressive test data of composites of nanotubes formed from twin base linkers, hydroxyapatite and poly hydroxyethylmethacrylate. Data=Mean±SEM.

As shown in FIG. 16, the mechanical properties of composites including the nanotubes formed from TBLs of Example 11 were tunable with the HA component, and the compressive strength increased with the weight ratio of HA. The 20% HA composites had the highest strength 42.7 MPa, which is suitable for orthopedic load bearing applications. According to certain aspects, composites have compressive strengths of between about 0.001 MPa to about 1000 GPa. Using TEM imaging, the average pore size of composites is 90.1 µm.

Example 15

Bacterial Study

For bacterial tests, PMMA and pure pHEMA were established as the control groups, and three types of bacterial strains (*Staphylococcus aureus*, *Staphylococcus epidermidis*, and *Pseudomonas aeruginosa*) were incubated on the sample surfaces in a 96-well plate for 1 h at 37° C., 5% $CO_2$ incubator. After the incubation, the samples were rinsed by deionized water, following the bacterial proliferation assay for 3 h.

Figure 17:
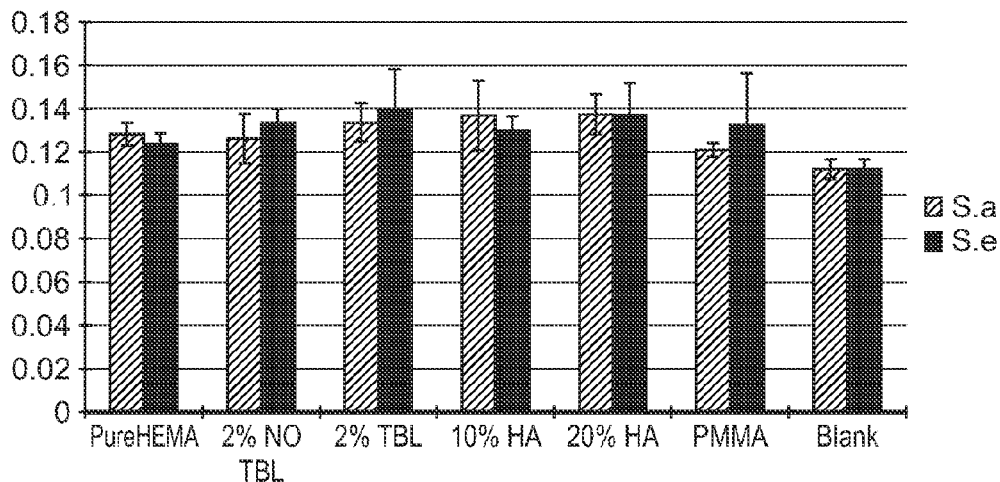
FIG. 17. Graph of bacterial adhesion density on composites of nanotubes formed from twin base linkers, hydroxyapatite and poly hydroxyethylmethacrylate. Data=Mean±SEM.

As shown in FIG. 17, in the bacterial study, compared to PMMA and pure pHEMA samples, the addition of TBL nanotubes formed from the TBLs of Example 11 and HA nanoparticles did not alter bacteria adhesion. Also, there is no discernable difference among pHEMA, TBL, HA or PMMA groups.

Example 16

Degradation

100% of the HEMA solution with 3 mg/mL AIBN, TBLs from Example 11 (none, 0.01 mg/mL) and HA nanoparticles (2%, 20%) were prepared as above. The weights of dry solidified samples were recorded first. Then, 4 samples in each group were placed in 50 ml centrifuge tubes with deionized water in a 37° C. incubator for 7, 30 and 60 days. After the prescribed time period, samples were dried and measured again, and the weight loss was calculated.

Figure 18:
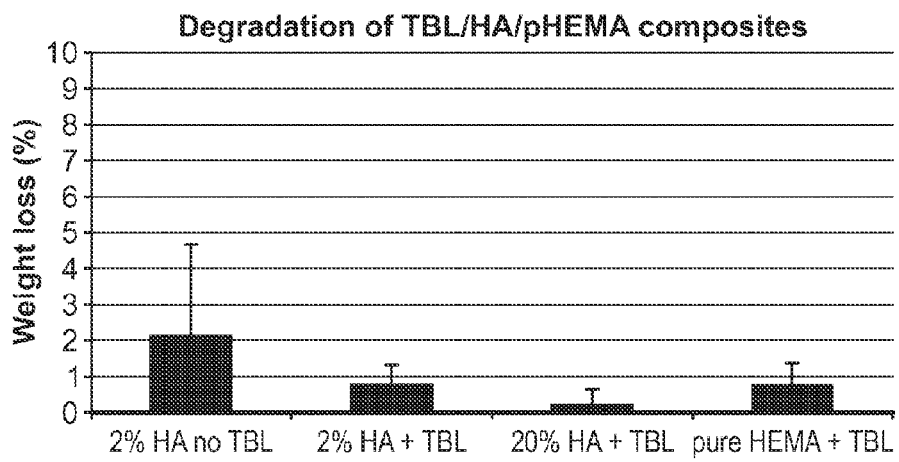
FIG. 18. Graph of degradation of composites of nanotubes formed from twin base linkers, hydroxyapatite and poly hydroxyethylmethacrylate after 7 days.
Figure 19:
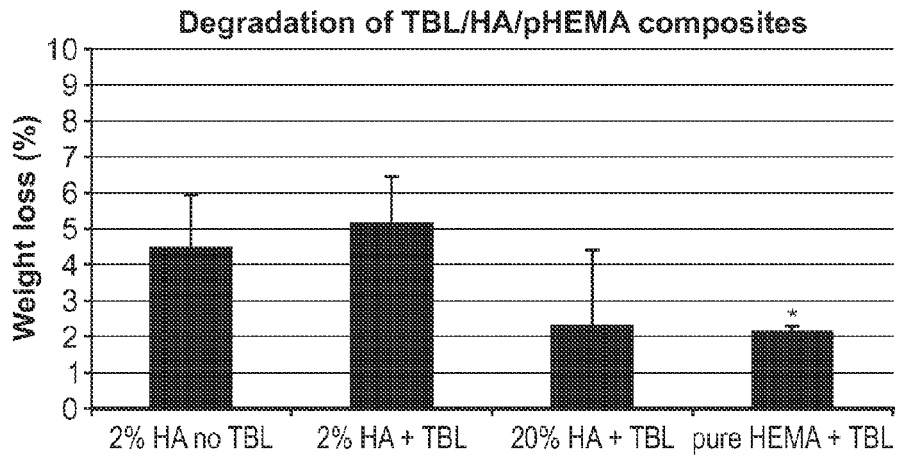
FIG. 19. Graph of degradation of composites of nanotubes formed from twin base linkers, hydroxyapatite and poly hydroxyethylmethacrylate after 1 month. $*p<0.05$ compared with the 2% HA no TBL group.

As shown in FIGS. 18 and 19, degradation tests of 7 and 30 days indicated small percentages of weight loss for all samples. After 30 days, the samples containing 2% HA with nanotubes of TBL molecules of Example 11 had the largest weight loss.

Example 17

Cell Cultures

A human fetal osteoblast cell line (ATCC, CRL-11372, VA) was cultured in Dulbecco's modified eagle's medium (DMEM, Invitrogen Corporation) supplemented with 10% fetal bovine serum (FBS, Hyclone, UT) and 1% penicillin/streptomycin (P/S, Hyclone, UT) under standard cell culture conditions (37° C., humidified, 5% $CO_2$/95% air). Cells were used up to population numbers of 3 in experiments without further characterization.

For standard toxicity studies, a rat skin fibroblast cell line (FR, ATCC, CRL-1213) was cultured in Eagle's Minimum Essential Medium (EMEM, ATCC, 30-2003) supplemented with 10% FBS under standard cell culture conditions. Rat aortic endothelial cells (RAEC, VEC Technologies) were cultured in MCDB-131 complete medium (VEC Technologies) under standard cell culture conditions. The fibroblasts were used at population numbers 6-9. Fibroblast and endothelial cell toxicity was not affected at the concentrations used which demonstrated that the compositions were not toxic at various concentrations.

Example 18

OsteoBlast and Fibroblast Adhesion Density

Osteoblasts and fibroblasts were separately seeded onto the substrates at a density of 3500 cells/$cm^2$ and were incubated in the cell culture medium (specifically, DMEM supplemented with FBS and P/S for osteoblasts and EMEM supplemented with FBS for fibroblasts) for 4 h. Then, the substrates formulated above were rinsed three times with a phosphate buffered saline (PBS) to remove non-adherent cells. The remaining cells were fixed using 10% normal buffered formaldehyde (Fisher Scientific) for 10 min and 0.1% Triton X-100 (Sigma-Aldrich, MO) for 5 min. Cells were then stained with rhodamine-phalloidin (staining F-actin filaments, Molecular Probes) to examine cell spreading and further stained with DAPI (Invitrogen). The cells were observed using a fluorescence microscope (Axiovert 200M, Zeiss) and five different areas of each sample were imaged. The cell density was determined by counting cells using Image Pro Analyzer. All cellular experiments were run in triplicate and repeated three times for each substrate.

Figure 20:
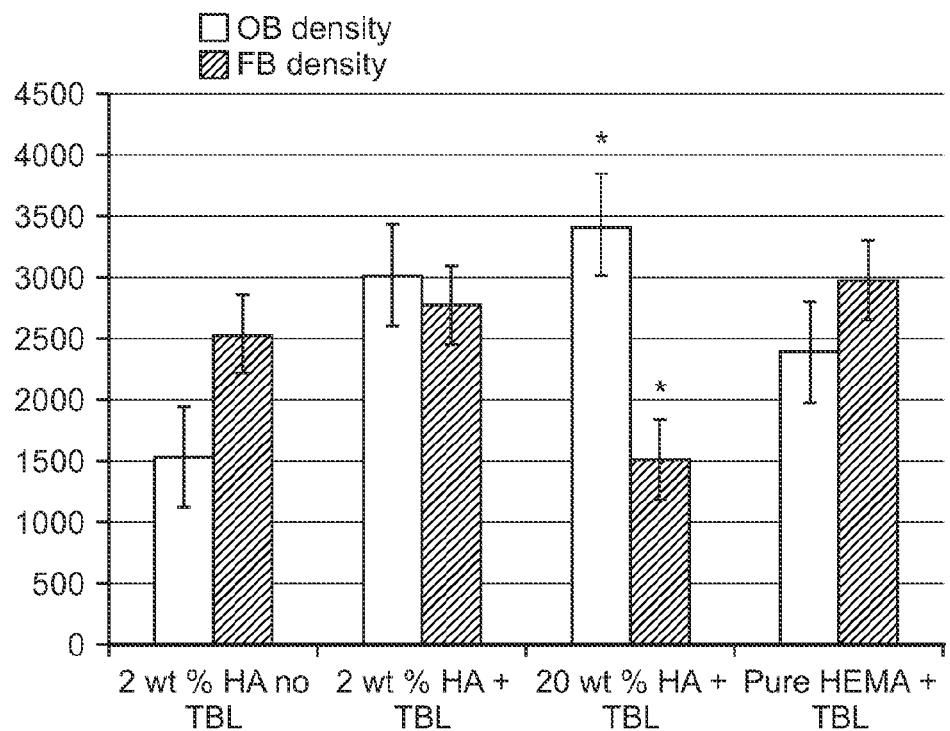
FIG. 20. Graph of increased osteoblast and decreased fibroblast density with increasing HA content in composites of nanotubes formed from twin base linkers, hydroxyapatite and poly hydroxyethylmethacrylate. Data=mean+/−SEM; N=3; $*p<0.01$ compared to all others with respective cell type. Time=4 hours. Y axis is cells/cm$^2$.

FIG. 20 demonstrates increased osteoblast density and decreased fibroblast density with increasing hydroxyapatite in combination with nanotubes formed from twin base linker modules of Example 11.

Example 19

Osteoblast Proliferation

Osteoblasts were prepared as described above, seeded randomly onto the substrate surface, and cultured under standard cell culture conditions for longer (1, 3, and 5 days) time periods. Osteoblast proliferation was assessed by measuring the amount of DNA in papin-digests using Hoeschst 33258 dye (Sigma) and a fluorospectrophotometer (Milton Roy Company, Fluorospectronic). The number of cells in the experimental samples was determined from a standard curve correlating the amount of DNA per known number of cells (assay sensitive to approximately 1,000). Proliferation at these long-time periods was reported as cell density (cells per unit surface area).

Figure 21:
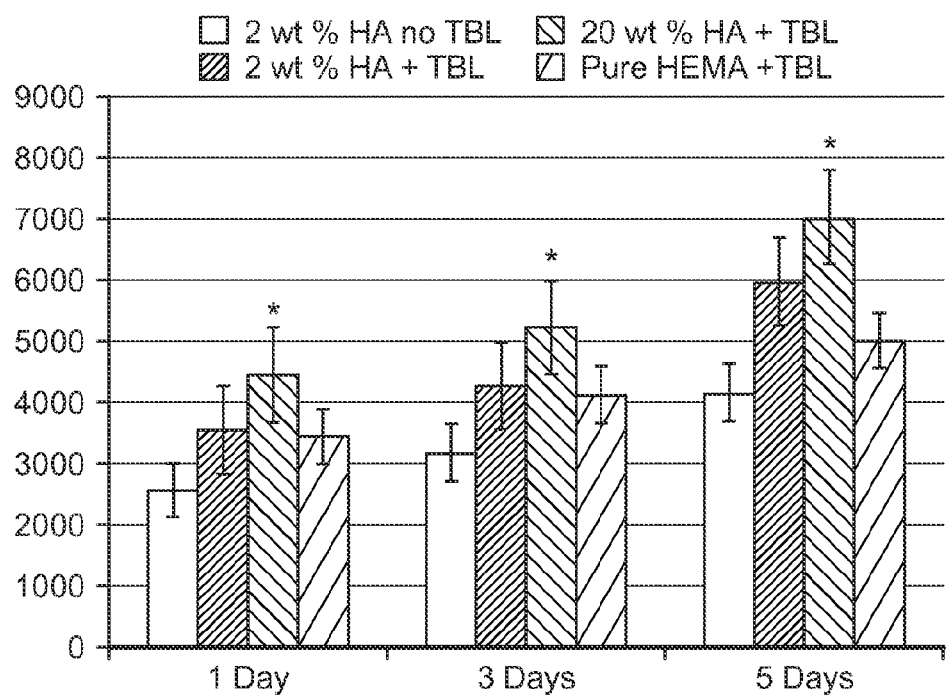
FIG. 21. Graph of increased osteoblast proliferation with increasing hydroxyapatite content in composites of nanotubes formed from twin base linkers, hydroxyapatite and poly hydroxyethylmethacrylate. Data=mean+/−SEM; N=3; $*p<0.01$ compared to all others with respect to all other samples. All substrates significantly greater with time. Y axis is cells/cm$^2$.

FIG. 21 demonstrates increased osteoblast proliferation with increasing hydroxyapatite content in combination with nanotubes formed from twin base linker modules of Example 11.

Example 20

Osteoblast Differentiation

Osteoblasts were prepared as described above, seeded randomly onto the substrate surface, and cultured under standard cell culture conditions for longer (1, 3, and 5 days) time periods. Osteoblast proliferation was assessed by measuring the amount of DNA in papin-digests using Hoeschst 33258 dye (Sigma) and a fluorospectrophotometer (Milton Roy Company, Fluorospectronic). The number of cells in the experimental samples was determined from a standard curve correlating the amount of DNA per known number of cells (assay sensitive to approximately 1,000). Proliferation at these long-time periods was reported as cell density (cells per unit surface area).

Total Intracellular Protein Content:

Osteoblasts (100,000 cell/$cm^2$) were seeded onto the substrates and were cultured in complete DMEM (that is, DMEM supplemented with 10% FBS, 1% P/S, 50 µg/ml ascorbate (Sigma) and 10 mM β-glycerophosphate (Sigma)) under standard cell culture conditions for 7, 14, and 21 days. The media was replaced every other day. At the end of the prescribed time periods, the substrates were first rinsed with Tris-buffered saline (TBS; a solution consisting of 42 mM Tris-HCl, 8 mM Tris Base and 0.15 M NaCl adjusted to a pH of 7.4; all chemicals from Sigma) three times and then the osteoblasts were lysed using distilled water and three freeze-thaw cycles. Total protein content in the cell lysates was determined spectrophotometrically using a BCA Protein Assay Reagent Kit (Pierce Chemical Co.) following manufacturer's instructions. Specifically, 25 µl of each sample lysate was incubated with 200 µl of the working reagent (containing cupric sulfate and bicinchoninic acid) at 37° C. for 30 min. Then, the light absorbance of these samples was measured by a spectrophotometer (SpectroMAX; Molecular Devices) at 562 nm. Total intracellular protein synthesized by osteoblasts cultured on the substrates was determined from a standard curve of absorbance versus known concentrations of albumin run in parallel with experimental samples. The total intracellular protein synthesis was normalized by substrate surface area.

Total Intracellular Collagen Content:

Collagen is a well-known protein contained in the extracellular matrix of bone. To determine these amounts, cell lysates were prepared as described above. 50 µl of osteoblast lysates were added per well of a 96-well plate (Corning). The collagen was allowed to dry on the plate through incubation at 37° C. for 16 hours and was then incubated at 37° C. for 24 hours in the presence of a desiccant (W.A. Hamond Drierite Company LTD.). Thereafter, the 96-well plate was rinsed three times with distilled water (1 min per wash and 200 µl per well). 100 μl of a 0.1% Sirius Red stain (Sirius Red powder in picric acid; Sigma) was dispensed into each well and was allowed to sit for one hour at room temperature. After that, each well was washed 5 times with 200 μl of 0.01 M HCl (Sigma) for 10 seconds per wash. 200 μl of 0.1 M NaOH (Sigma) was added into each well and was allowed to sit for 5 min. Finally, the solution in each well was mixed, transferred to a second plate, and absorbance read at 540 nm in a spectrophotometer (SpectroMAX; Molecular Devices). The total intracellular collagen synthesized by osteoblasts cultured on the substrates was determined from a standard curve of absorbance versus known concentrations of collagen run in parallel with experimental samples. The total intracellular collagen was normalized by substrate surface area.

Figure 22:
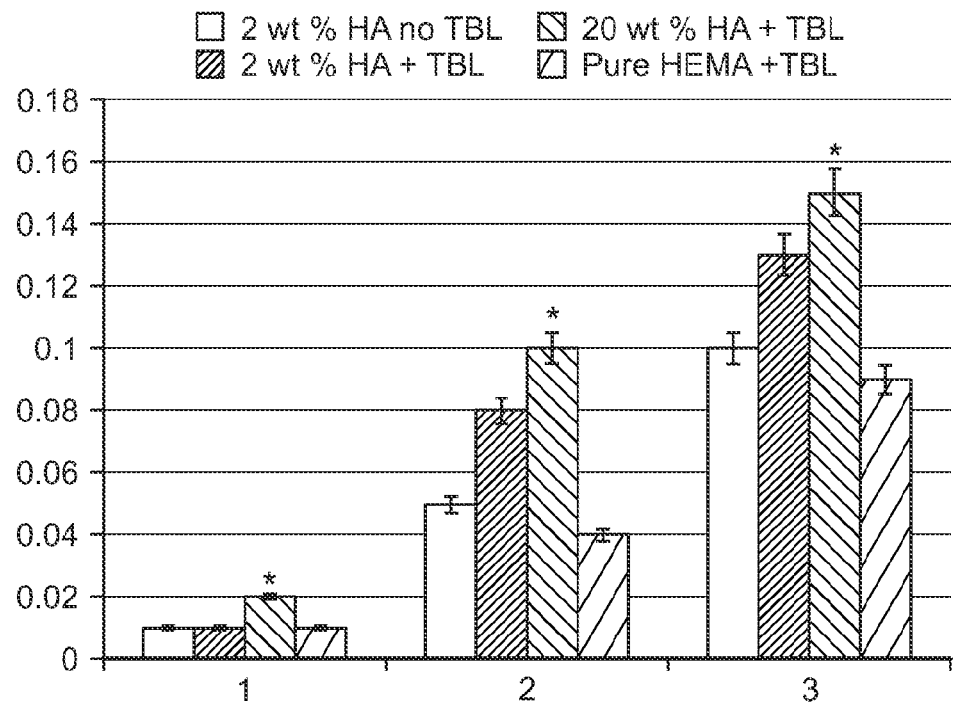
FIG. 22. Graph of increased osteoblast collagen synthesis by osteoblasts with increasing hydroxyapatite content in composites of nanotubes formed from twin base linkers, hydroxyapatite and poly hydroxyethylmethacrylate. Data=mean+/−SEM; N=3; $*p<0.01$ compared to all others with respect to all other samples. All substrates significantly greater with time. Y axis is microgram collagen/microgram protein.

FIG. 22 demonstrates increased osteoblast collagen synthesis by osteoblasts with increasing hydroxyapatite content in combination with nanotubes formed from twin base linker modules of Example 11.

Alkaline Phosphatase Activity:

Alkaline phosphatase is an enzyme whose synthesis indicates the differentiation of osteoblasts from non-calcium depositing to calcium depositing cells. To test this, cell lysates were prepared as previously described and a commercial Alkaline/Acid Phosphatase Assay Kit (Upstate) was used to determine the concentration of alkaline phosphatase in these cell lysates following manufacturer's instructions. Aliquots of the distilled water supernatants were first mixed and incubated with 40 mM $NiCl_2$, 5 mg/ml BSA, 1 mM phosphopeptide solution, and Pnpp Ser/Thr Assay Buffer at 37° C. for 10-15 min. Then, they were incubated with Malachite Green solution for 15-20 min at room temperature. The optical absorbance values were measured by a spectrophotometer (SpectroMAX; Molecular Devices) at 650 nm. Alkaline phosphatase synthesized by osteoblasts cultured on the substrates was determined from a standard curve of absorbance versus known concentrations of potassium phosphate monobasic run in parallel with experimental samples. The alkaline phosphatase activity was normalized by substrate surface area.

Figure 23:
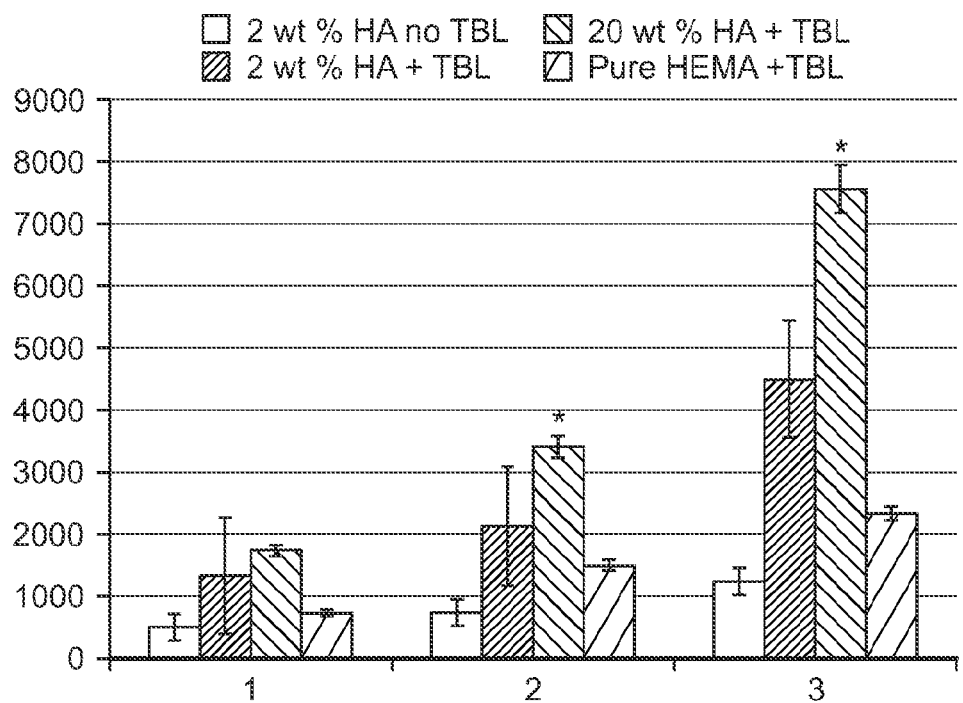
FIG. 23. Graph of increased osteoblast alkaline phosphatase synthesis by osteoblasts with increasing hydroxyapatite content in composites of nanotubes formed from twin base linkers, hydroxyapatite and poly hydroxyethylmethacrylate. Data=mean+/−SEM; N=3; $*p<0.01$ compared to all others with respect to all other samples. All substrates significantly greater with time. Y axis is alkaline phosphatase activity measured in picomole/min/cm$^2$.
Figure 24:
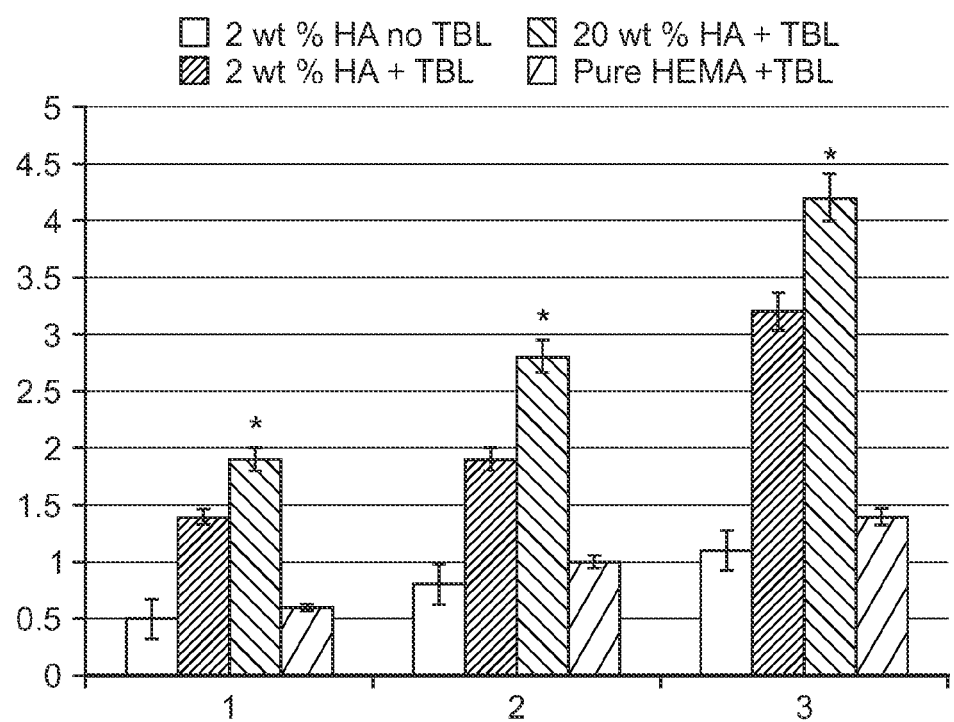
FIG. 24. Graph of increased osteoblast calcium deposition by osteoblasts with increasing hydroxyapatite content in composites of nanotubes formed from twin base linkers, hydroxyapatite and poly hydroxyethylmethacrylate. Data=mean+/−SEM; N=3; $*p<0.01$ compared to all others with respect to all other samples. All substrates significantly greater with time. Y axis is microgram calcium/cm$^2$.

FIG. 23 demonstrates increased alkaline phosphatase synthesis by osteoblasts with increasing hydroxyapatite content in combination with nanotubes formed from twin base linker modules of Example 11.

Quantification of Extracellular Calcium:

Calcium deposition as a measure of osteoblast differentiation was determined. After the cells were lysed as described above, the substrates (and remaining calcium deposits on them) were incubated with 0.6 N HCl (Sigma) at 37° C. overnight. The amount of calcium present in the acidic supernatant was quantified using a Calcium Quantification Kit (Sigma) following manufacturer's instructions; light absorbance of the samples was measured using a spectrophotometer (SpectroMAX; Molecular Devices) at 575 nm. Total calcium (mg/dl) was calculated from standard curves of absorbance versus known concentrations of calcium measured in parallel with the experimental samples. Calcium concentration values were normalized by substrate surface area.

FIG. 22 demonstrates increased osteoblast calcium deposition by osteoblasts with increasing hydroxyapatite content in combination with nanotubes formed from twin base linker modules of Example 11.

Given the benefit of the above disclosure and description of exemplary embodiments, it will be apparent to those skilled in the art that numerous alternative and different embodiments are possible in keeping with the general principles of the invention disclosed here. Those skilled in this art will recognize that all such various modifications and alternative embodiments are within the true scope and spirit of the invention. While the invention has been illustrated and described in detail in the drawings and foregoing description, such illustration and description is to be considered as exemplary and not restrictive in character, it being understood that, only the preferred embodiments have been shown and described and that all changes and modifications that come within the spirit of the invention are desired to be protected. The appended claims are intended to cover all such modifications and alternative embodiments. It should be understood that the use of a singular indefinite or definite article (e.g., "a," "an," "the," etc.) in this disclosure and in the following claims follows the traditional approach in patents of meaning "at least one" unless in a particular instance it is clear from context that the term is intended in that particular instance to mean specifically one and only one. Likewise, the term "comprising" is open ended, not excluding additional items, features, components, etc. References identified herein are expressly incorporated herein by reference in their entireties unless otherwise indicated.

What is claimed is:

1. A method of promoting osteoblast differentiation and proliferation at a site of a bone injury or defect or bone surgical site comprising providing an implant having a composition including nanotubes formed from modules according to Formula II, nanoparticles, and a matrix material, and optionally nanotubes formed from modules according to Formula I wherein Formula II is

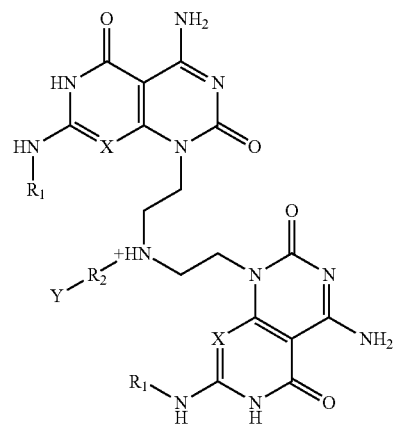

wherein X is CH or nitrogen; Y is lysine-arginine-serine-arginine, isoleucine-lysine-valine-alanine-valine or tyrosine-isoleucine-glycine-serine-arginine; $R_2$ is absent or a linker and $R_1$ is aliphatic, and wherein Formula I is

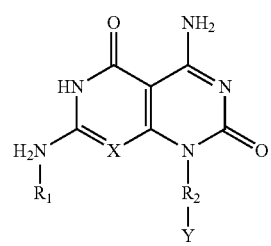

wherein X is CH or nitrogen; Y is lysine-arginine-serine-arginine, isoleucine-lysine-valine-alanine-valine or tyrosine-isoleucine-glycine-serine-arginine; R₂ is absent or a linker and R₁ is aliphatic, and placing the implant at the site of a bone injury or defect or bone surgical site.

2. The method of claim 1 wherein R₂ is NH₃⁺,

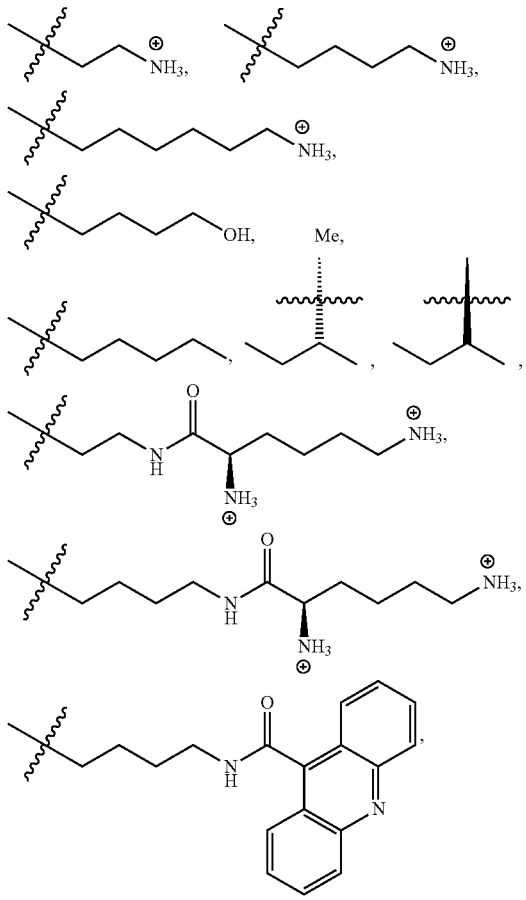

(CH₂)₃CO or (CH₂)n where n is an integer of 1, 2, 3, or 4.

3. The method of claim 1 where R₁ is C₁ to C₁₀ alkyl, straight or branched chain, saturated or unsaturated.

4. The method of claim 1 wherein the nanoparticles are nanoparticles of calcium phosphate, hydroxyapatite, apatite, oxyapatite, octacalcium phosphate, monocalcium phosphate, dicalcium phosphate, tricalcium phosphate, β-tricalcium phosphate, α-tricalcium phosphate, tetracalcium phosphate, calcium hydrogen phosphate or calcium dihydrogen phosphate.

5. The method of claim 1 wherein the matrix material is one or more of polylactic acid, polylactide-coglycolide, polyglycolic acid, polymethylmethacrylate, polyurethane, polycaprolactone, polyethylene, polystyrene, polypropylene, polypyrrole, or poly(2-hydroxyethyl methacrylate).

6. The method of claim 1 wherein Formula I is absent, X is N, R₁ is methyl, R₂ is (CH₂)₃CO, Y is lysine-arginine-serine-arginine, the nanoparticles are nanoparticles of hydroxyapatite, and the matrix material is poly(2-hydroxyethylmethacrylate).

7. A compound having the formula

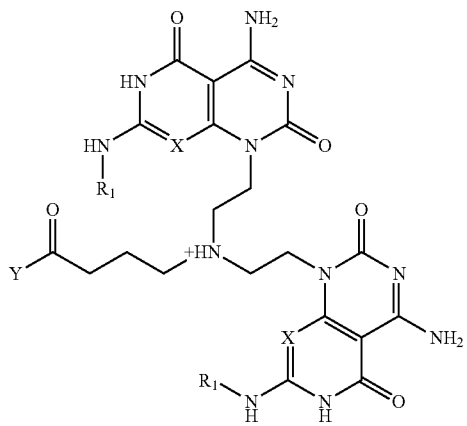

wherein X is CH or nitrogen; Y is lysine-arginine-serine-arginine, isoleucine-lysine-valine-alanine-valine or tyrosine-isoleucine-glycine-serine-arginine; and R₁ is C1 to C10 alkyl, straight or branched chain, saturated or unsaturated; and salts thereof.

8. A compound having the formula

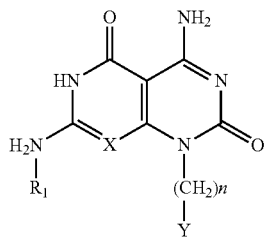

wherein X is CH or nitrogen; n is an integer of, 1, 2, 3, or 4; Y is lysine-arginine-serine-arginine, isoleucine-lysine-valine-alanine-valine or tyrosine-isoleucine-glycine-serine-arginine; and R₁ is C1 to C10 alkyl, straight or branched chain, saturated or unsaturated; and salts thereof.

9. A structure formed from the self-assembly in aqueous media of compounds having the formula

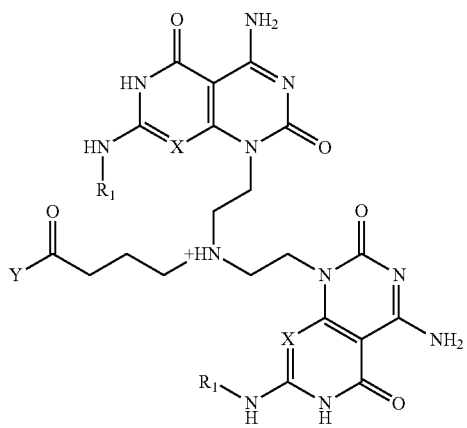

wherein X is CH or nitrogen; Y is lysine-arginine-serine-arginine, isoleucine-lysine-valine-alanine-valine or tyrosine-isoleucine-glycine-serine-arginine; and $R_1$ is C1 to C10 alkyl, straight or branched chain, saturated or unsaturated; and salts thereof.

10. A structure formed from the self-assembly in aqueous media of compounds having the formula

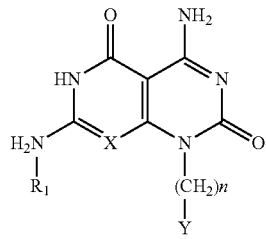

wherein X is CH or nitrogen; n is an integer of, 1, 2, 3, or 4; Y is lysine-arginine-serine-arginine, isoleucine-lysine-valine-alanine-valine or tyrosine-isoleucine-glycine-serine-arginine; and $R_1$ is C1 to C10 alkyl, straight or branched chain, saturated or unsaturated; and salts thereof.

11. A structure formed from the self-assembly in aqueous media of one or more compounds having the formula

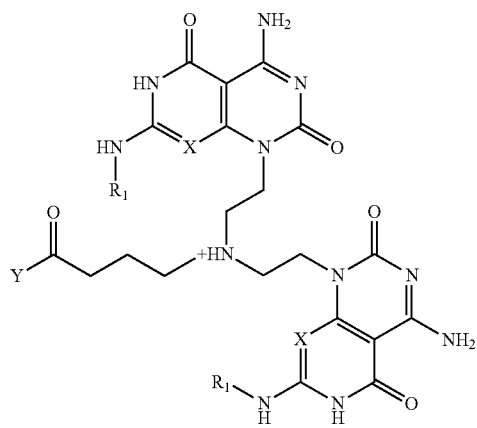

wherein X is CH or nitrogen; Y is lysine-arginine-serine-arginine, isoleucine-lysine-valine-alanine-valine or tyrosine-isoleucine-glycine-serine-arginine; and $R_1$ is C1 to C10 alkyl, straight or branched chain, saturated or unsaturated; and salts thereof, and one or more compounds having the formula

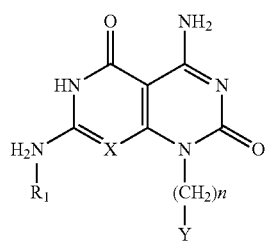

wherein X is CH or nitrogen; n is an integer of, 1, 2, 3, or 4; Y is lysine-arginine-serine-arginine, isoleucine-lysine-valine-alanine-valine or tyrosine-isoleucine-glycine-serine-arginine; and $R_1$ is C1 to C10 alkyl, straight or branched chain, saturated or unsaturated; and salts thereof.

12. A method of forming a nanotube comprising placing in an aqueous media compounds having the formula

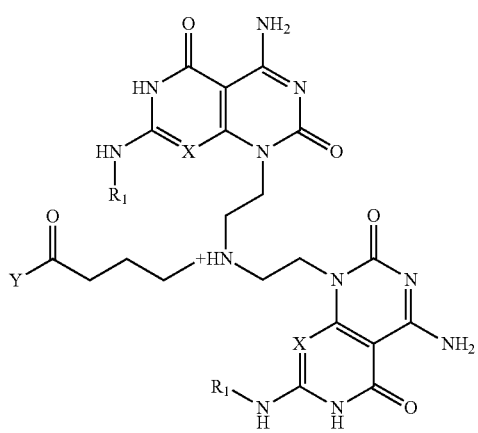

wherein X is CH or nitrogen; Y is lysine-arginine-serine-arginine, isoleucine-lysine-valine-alanine-valine or tyrosine-isoleucine-glycine-serine-arginine; and $R_1$ is C1 to C10 alkyl, straight or branched chain, saturated or unsaturated; and salts thereof, and at a sufficient concentration that a nanotube is formed.

13. A method of forming a nanotube comprising placing in an aqueous media compounds having the formula

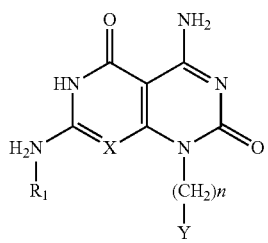

wherein X is CH or nitrogen; n is an integer of, 1, 2, 3, or 4; Y is lysine-arginine-serine-arginine, isoleucine-lysine-valine-alanine-valine or tyrosine-isoleucine-glycine-serine-arginine; and $R_1$ is C1 to C10 alkyl, straight or branched chain, saturated or unsaturated; and salts thereof.

14. A method of making an implant comprising coating an implant with a nanotube formed from compounds having the formula

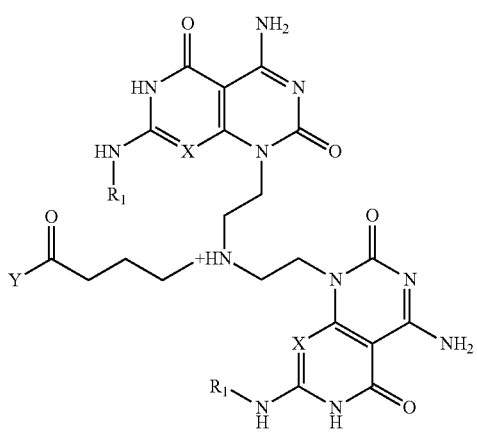

wherein X is CH or nitrogen; Y is lysine-arginine-serine-arginine, isoleucine-lysine-valine-alanine-valine or tyrosine-isoleucine-glycine-serine-arginine; and $R_1$ is C1 to C10 alkyl, straight or branched chain, saturated or unsaturated; and salts thereof.

15. A method of making an implant comprising coating an implant with a nanotube formed from compounds having the formula

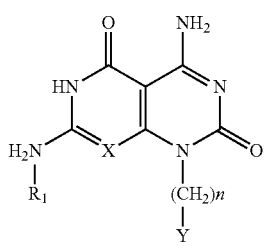

wherein X is CH or nitrogen; n is an integer of, 1, 2, 3, or 4; Y is lysine-arginine-serine-arginine, isoleucine-lysine-valine-alanine-valine or tyrosine-isoleucine-glycine-serine-arginine; and $R_1$ is C1 to C10 alkyl, straight or branched chain, saturated or unsaturated; and salts thereof.

16. A method of making an implant comprising coating an implant with a nanotube formed from one or more compounds having the formula

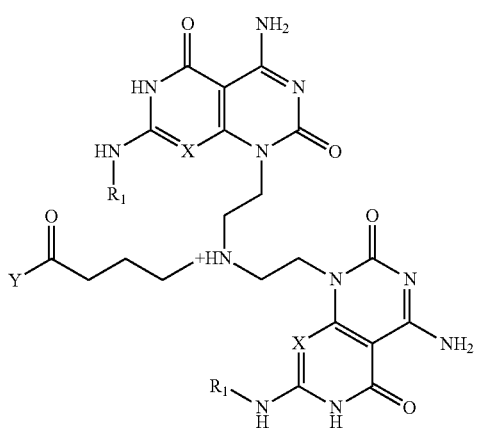

wherein X is CH or nitrogen; Y is lysine-arginine-serine-arginine, isoleucine-lysine-valine-alanine-valine or tyrosine-isoleucine-glycine-serine-arginine; and $R_1$ is C1 to C10 alkyl, straight or branched chain, saturated or unsaturated; and salts thereof, and one or more compounds having the formula

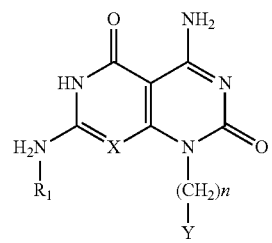

wherein X is CH or nitrogen; n is an integer of, 1, 2, 3, or 4; Y is lysine-arginine-serine-arginine, isoleucine-lysine-valine-alanine-valine or tyrosine-isoleucine-glycine-serine-arginine; and $R_1$ is C1 to C10 alkyl, straight or branched chain, saturated or unsaturated; and salts thereof.

17. A method of promoting growth of tissue at the site of an implant comprising implanting an implant having a coating of nanotubes formed from compounds having the formula

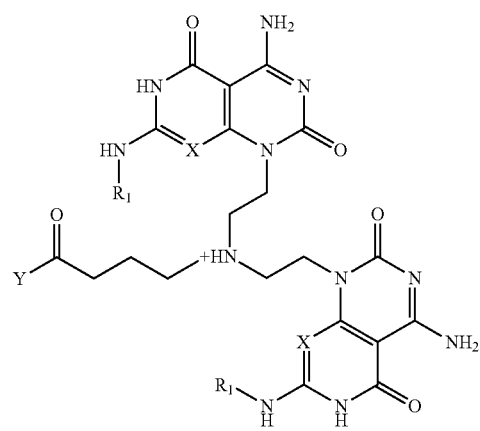

wherein X is CH or nitrogen; Y is lysine-arginine-serine-arginine, isoleucine-lysine-valine-alanine-valine or tyrosine-isoleucine-glycine-serine-arginine; and $R_1$ is C1 to C10 alkyl, straight or branched chain, saturated or unsaturated; and salts thereof.

18. A method of promoting growth of tissue at the site of an implant comprising implanting an implant having a coating of nanotubes formed from compounds having the formula

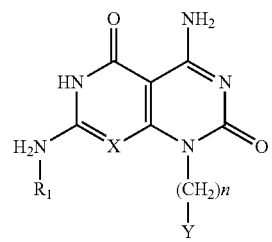

wherein X is CH or nitrogen; n is an integer of, 1, 2, 3, or 4; Y is lysine-arginine-serine-arginine, isoleucine-lysine-valine-alanine-valine or tyrosine-isoleucine-glycine-serine-arginine; and $R_1$ is C1 to C10 alkyl, straight or branched chain, saturated or unsaturated; and salts thereof.

19. A method of promoting growth of tissue at the site of an implant comprising implanting an implant having a coating of nanotubes formed from one or more compounds having the formula

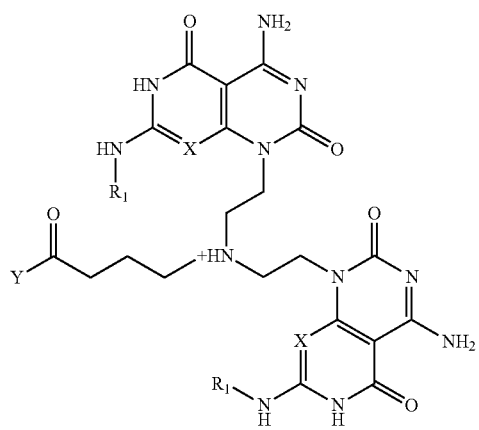

wherein X is CH or nitrogen; Y is lysine-arginine-serine-arginine, isoleucine-lysine-valine-alanine-valine or tyrosine-isoleucine-glycine-serine-arginine; and $R_1$ is C1 to C10 alkyl, straight or branched chain, saturated or unsaturated; and salts thereof, and one or more compounds having the formula

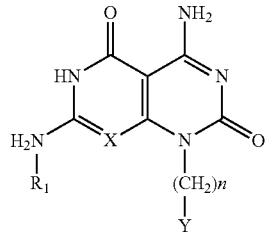

wherein X is CH or nitrogen; n is an integer of, 1, 2, 3, or 4; Y is lysine-arginine-serine-arginine, isoleucine-lysine-valine-alanine-valine or tyrosine-isoleucine-glycine-serine-arginine; and $R_1$ is C1 to C10 alkyl, straight or branched chain, saturated or unsaturated; and salts thereof.

20. A composition comprising nanotubes, a compound for providing mechanical strength and a matrix material, wherein the nanotubes are formed from one or more compounds having Formula II

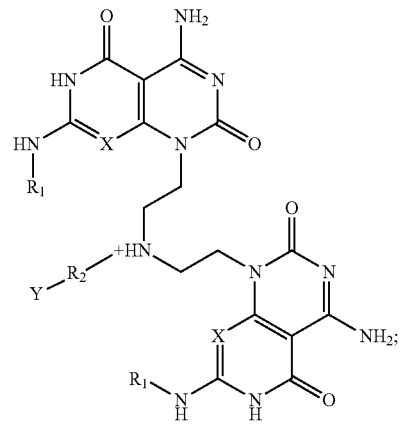

wherein X is CH or nitrogen; Y is lysine-arginine-serine-arginine, isoleucine-lysine-valine-alanine-valine or tyrosine-isoleucine-glycine-serine-arginine; $R_2$ is absent or a linker and $R_1$ is aliphatic, or one or more compounds having Formula I

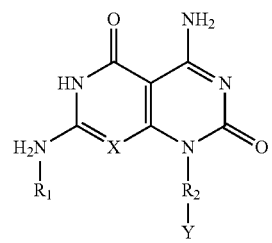

wherein X is CH or nitrogen; Y is lysine-arginine-serine-arginine, isoleucine-lysine-valine-alanine-valine or tyrosine-isoleucine-glycine-serine-arginine; $R_2$ is absent or a linker and $R_1$ is aliphatic.

21. The composition of claim 20 wherein $R_2$ is $NH_3^+$,

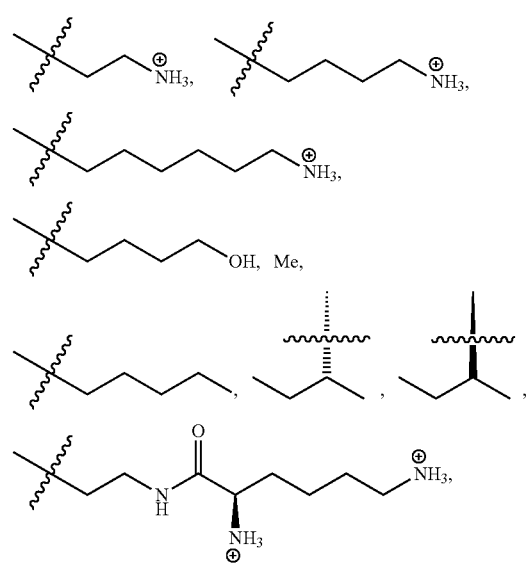

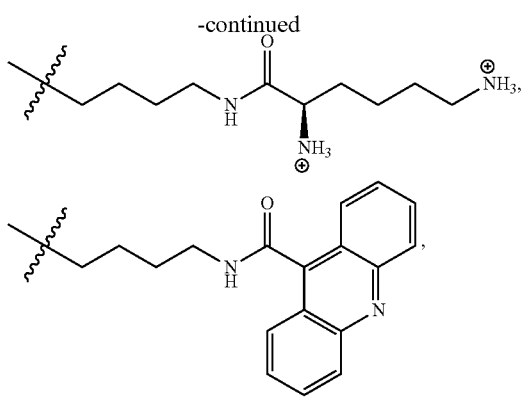

$(CH_2)_3CO$ or $(CH_2)n$ where n is an integer of 1, 2, 3, or 4.

22. The composition of claim 20 where $R_1$ is $C_1$ to $C_{10}$ alkyl, straight or branched chain, saturated or unsaturated.

23. The composition of claim 20 wherein the compound for providing mechanical strength is a nanoparticle of calcium phosphate, hydroxyapatite, apatite, oxyapatite, octacalcium phosphate, monocalcium phosphate, dicalcium phosphate, tricalcium phosphate, β-tricalcium phosphate, α-tricalcium phosphate, tetracalcium phosphate, calcium hydrogen phosphate or calcium dihydrogen phosphate.

24. The composition of claim 20 wherein the matrix material is one or more of polylactic acid, polylactide-coglycolide, polyglycolic acid, polymethylmethacrylate, polyurethane, polycaprolactone, polyethylene, polystyrene polypropylene, polypyrrole, or poly(2-hydroxyethyl methacrylate).

25. The composition of claim 20 wherein Formula I is absent, X is N, $R_1$ is methyl, $R_2$ is $(CH_2)_3CO$, Y is lysine-arginine-serine-arginine, the compound for providing mechanical strength is a nanoparticle of hydroxyapatite, and the matrix material is poly(2-hydroxyethylmethacrylate).

26. The method of claim 1 wherein the implant is an injectable liquid, moldable putty or hardened structure.

27. The composition of claim 20 wherein the composition is an injectable liquid, moldable putty or hardened structure.

28. The method of claim 1 wherein the implant is a porous hardened structure.

29. The method of claim 1 wherein the implant is a nonporous hardened structure.

30. The composition of claim 20 the composition is in the form of a porous hardened structure.

31. The composition of claim 20 the composition is in the form of a nonporous hardened structure.

32. The method of claim 1 wherein the implant is a plate, rod, screw, cage, scaffold or film.

33. The composition of claim 20 wherein the composition is in the form of a plate, rod, screw, cage, scaffold, film or coating.

34. The method of claim 17 wherein the site of the implant is bone, cartilage, vascular tissue, heart tissue, cardiovascular tissue, bladder tissue, nervous system tissue, skin tissue, spine, a periodontal defect, a dental extraction socket, a cystic defect, a sinus, an alveolar ridge, an oral site, a maxillofacial site or an orthopedic site.

35. The method of claim 18 wherein the site of the implant is bone, cartilage, vascular tissue, heart tissue, cardiovascular tissue, bladder tissue, nervous system tissue, skin tissue, spine, a periodontal defect, a dental extraction socket, a cystic defect, a sinus, an alveolar ridge, an oral site, a maxillofacial site or an orthopedic site.

36. The method of claim 19 wherein the site of the implant is bone, cartilage, vascular tissue, heart tissue, cardiovascular tissue, bladder tissue, nervous system tissue, skin tissue, spine, a periodontal defect, a dental extraction socket, a cystic defect, a sinus, an alveolar ridge, an oral site, a maxillofacial site or an orthopedic site.

37. The method of claim 1 wherein the matrix material is a curable matrix material.

38. The composition of claim 20 wherein the matrix material is a curable matrix material.

39. The method of claim 17 wherein the growth of tissue comprises expansion and growth of cells into tissue wherein the cells are osteoblasts, fibroblasts, endothelial cells, keratinocytes, cardiac myocytes, chondrocytes, synoviocytes, mesenchymel stem cells, neural stem cells, islet cells, hepatocytes, smooth muscle cells, urothelial cells, neurons or Schwann cells.

40. The method of claim 18 wherein the growth of tissue comprises expansion and growth of cells into tissue wherein the cells are osteoblasts, fibroblasts, endothelial cells, keratinocytes, cardiac myocytes, chondrocytes, synoviocytes, mesenchymel stem cells, neural stem cells, islet cells, hepatocytes, smooth muscle cells, urothelial cells, neurons or Schwann cells.

41. The method of claim 19 wherein the growth of tissue comprises expansion and growth of cells into tissue wherein the cells are osteoblasts, fibroblasts, endothelial cells, keratinocytes, cardiac myocytes, chondrocytes, synoviocytes, mesenchymel stem cells, neural stem cells, islet cells, hepatocytes, smooth muscle cells, urothelial cells, neurons or Schwann cells.

* * * * *